US011098381B2

(12) United States Patent
Foster et al.

(10) Patent No.: US 11,098,381 B2
(45) Date of Patent: Aug. 24, 2021

(54) MATERIALS AND METHODS FOR CONTROLLING REGULATION IN BIOSYNTHESIS IN SPECIES OF THE GENERA *RALSTONIA* OR *CUPRIAVIDUS* AND ORGANISMS RELATED THERETO

(71) Applicant: INV Nylon Chemicals Americas, LLC, Wilmington, DE (US)

(72) Inventors: Alexander Brett Foster, Redcar (GB); Jonathan Kennedy, Redcar (GB)

(73) Assignee: INV Nylon Chemicals Americas, LLC, Wilmington, DE (US)

(*) Notice: Subject to any disclaimer, the term of this patent is extended or adjusted under 35 U.S.C. 154(b) by 0 days.

(21) Appl. No.: 16/398,384

(22) Filed: Apr. 30, 2019

(65) Prior Publication Data
US 2019/0338376 A1 Nov. 7, 2019

Related U.S. Application Data

(60) Provisional application No. 62/665,790, filed on May 2, 2018.

(51) Int. Cl.
*C12P 7/62* (2006.01)
*C12P 7/16* (2006.01)
*C12R 1/38* (2006.01)
*C12N 15/52* (2006.01)
*C12N 15/78* (2006.01)
*C12P 7/04* (2006.01)
*C12N 1/20* (2006.01)
*C12N 15/70* (2006.01)

(52) U.S. Cl.
CPC ............... *C12R 1/38* (2013.01); *C12N 15/52* (2013.01); *C12N 15/78* (2013.01); *C12P 7/04* (2013.01); *C12Y 104/01002* (2013.01); *C12Y 104/01003* (2013.01); *C12Y 104/01004* (2013.01); *C12Y 104/01013* (2013.01); *C12Y 207/07042* (2013.01)

(58) Field of Classification Search
CPC .... C12P 7/18; C12P 7/42; C12P 7/625; C12P 7/6436; C12N 15/70; C12N 9/16; C12N 9/1217; C12N 9/18; C12Y 301/0202
USPC ...... 435/167, 146, 155, 252, 3, 257.2, 320.1
See application file for complete search history.

(56) References Cited

U.S. PATENT DOCUMENTS

| | | | |
|---|---|---|---|
| 1,007,215 A | 9/1918 | Conradie et al. | ....... C08L 77/12 |
| 1,019,665 A | 2/1919 | Pearlman et al. | .... C12P 13/001 |
| 7,384,783 B2 | 6/2008 | Kunas et al. | |
| 8,809,027 B1 | 8/2014 | Lynch et al. | |
| 8,986,960 B2 | 3/2015 | Sichwart | |
| 9,580,733 B2 | 2/2017 | Botes et al. | ............ C12P 13/02 |
| 9,637,764 B2 | 5/2017 | Botes et al. | .......... C12P 13/001 |
| 9,862,973 B2 | 1/2018 | Botes et al. | ............ C12P 5/007 |
| 9,920,339 B2 | 3/2018 | Kadi et al. | ................ C12P 7/62 |
| 2012/0003706 A1 | 1/2012 | Hickey | |
| 2012/0015413 A1 | 1/2012 | Sichwart et al. | |
| 2012/0064622 A1 | 3/2012 | Fischer et al. | |
| 2013/0034884 A1 | 2/2013 | Burgard et al. | |
| 2013/0065285 A1 | 3/2013 | Sefton | |
| 2013/0323714 A1 | 12/2013 | Cheng et al. | |
| 2015/0315599 A1 | 11/2015 | Shetty et al. | |
| 2016/0222420 A1 | 8/2016 | Botes | |
| 2017/0218406 A1 | 8/2017 | Conradie et al. | |
| 2018/0023103 A1 | 1/2018 | Foster et al. | |
| 2018/0023104 A1 | 1/2018 | Cartman et al. | |
| 2018/0100160 A1 | 4/2018 | Bawdon et al. | ....... C12N 15/74 |
| 2019/0124947 A1 | 5/2019 | Pearlman et al. | |
| 2019/0300838 A1 | 10/2019 | Smith et al. | |
| 2019/0300839 A1 | 10/2019 | Smith et al. | |
| 2019/0316072 A1 | 10/2019 | Smith et al. | |
| 2019/0338320 A1 | 11/2019 | Foster et al. | |

FOREIGN PATENT DOCUMENTS

| | | |
|---|---|---|
| EP | 0995490 A2 | 4/2000 |
| EP | 1728853 A1 | 12/2006 |
| EP | 1938892 A1 | 7/2008 |
| EP | 3399015 A1 | 11/2018 |
| JP | 2009225662 A | 10/2009 |
| JP | 2013179909 A | 9/2013 |
| WO | 2008094282 A1 | 8/2008 |
| WO | 2010003007 A2 | 1/2010 |
| WO | 2010069313 A2 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2017115855 A1 | 7/2014 |

(Continued)

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Lu et al. Appl Microbial Biotech 2012, 96, pp. 283-297.*
Lee, J.N., et al., "Metabolic Engineering of Pentose Phosphate Pathway in Ralsonia eutropha for Enhanced Biosynthesis of Poly-hydroxybutyrate", Biotechnology Progress, 2003, vol. 19, Issue 5, pp. 1444-1449.

(Continued)

*Primary Examiner* — Robert B Mondesi
*Assistant Examiner* — Mohammad Y Meah

(57) ABSTRACT

Methods for increasing carbon-based chemical product yield in an organism by genetically modifying one or more genes involved in a stringent response and/or in a regulatory network, nonnaturally occurring organisms having increased carbon-based chemical product yield, and methods for use in production of carbon-based chemical products are provided.

2 Claims, 1 Drawing Sheet
Specification includes a Sequence Listing.

(56) References Cited

FOREIGN PATENT DOCUMENTS

| WO | 2015117019 | | 8/2015 |
|---|---|---|---|
| WO | 2015195654 | A1 | 12/2015 |
| WO | 2017165244 | A1 | 9/2017 |
| WO | 2018005770 | A2 | 1/2018 |
| WO | 2018022595 | A1 | 2/2018 |
| WO | 2018022633 | A1 | 2/2018 |
| WO | 2018106549 | A1 | 6/2018 |
| WO | 2019191761 | A1 | 10/2019 |
| WO | 2019191763 | A1 | 10/2019 |
| WO | 2019191767 | A1 | 10/2019 |
| WO | 2019191770 | A1 | 10/2019 |
| WO | 2019191772 | A1 | 10/2019 |
| WO | 2019213108 | A1 | 11/2019 |
| WO | 2019213118 | A1 | 11/2019 |

OTHER PUBLICATIONS

Lee, et al., "Regulation of poly-hydroxybutyrate biosynthesis by nicotinamide nucleotide in Alcaligene eutrophus" FEMS Microbiological letters, 1995, vol. 131, pp. 35-39.

Lee, et al., "Microbial Production of Ethanol from Acetate by Engineered Ralstonia Eutropha", Biotechnology and Bioprocess Engineering, vol. 21, 2016, pp. 402-407.

Li, Z.J., et al., "Overexpression of NAD kinase in recombinant *Escherichia coli* harboring the phbCAB operon improves poly(3-hydroxybutyrate) production", Appl Microbial Biotechnol., 2009, vol. 83, Issue 5, pp. 939-947.

Marc, J., et al., "Over expression of GroESL in Cupriavidus necator for heterotrophic and autotrophic isopropanol production", Metabolic Engineering,vol. 42, 2017, pp. 74-84.

March, J.C., et al., "Expression of an anaplerotic enzyme, pyruvate carboxylase, improves recombinant protein production in *Escherichia coli*" Applied and Environmental Microbiology, 2002, vol. 68, Issue 11, pp. 5620-5624.

Martin, Koller, et al., "Continuous production mode as a viable process-engineering tool for efficient poly (hydroxyalkanoate) (PHA) bio-production", Chemical and Biochemical Engineering Quarterly, vol. 28, XP002792820 ,2014, pp. 65-77.

Mckinlay, J.B., et al., "Carbon dioxide fixation as a central redox cofactor recycling mechanism in bacteria" PNAS, 2010, vol. 107, Issue 26, pp. 11669-11675.

Meng, J., et al. "High-yield anaerobic succinate production by strategically regulating multiple metabolic pathways based on stoichiometric maximumin *Escherichia coli*" Microbial Cell Factories, vol. 15, 2016, pp. 13.

Montiel-Jarillo, G., et al., "Enrichment of a mixed microbial culture for polyhydroxyalkanoates production: Effect of pH and N and P concentrations", Science of the Total Environment, vol. 583, 2017, pp. 300-307.

Nguyen, C., et al., "Trapping the dynamic acyl carrier protein in fatty acid biosynthesis", Nature, vol. 505, No. 7483 ,Dec. 22, 2013, pp. 427-431.

Orita, L., et al., "Identification of mutation points in Cupriavidus necator NCIMB 11599 and genetic reconstitution of glucose-utilization ability in wild strain H16 for polyhydroxyalkanoate production" Journal of Bioscience and Bioengineering, 2012, vol. 113, Issue 1, pp. 63-69.

Papagiani, M. "Recent advances in engineering the central carbon metabolism of industrially important bacteria", Microbial Cell Factories, 2012, vol. 11, pp. 13.

Park, J-S., et al., "Metabolic Characteristics of Isocitrate Dehydrogenase Leaky Mutant of Alcaligene eutrophus and Its Utilization for Poly-Hydroxybutyrate Production" Journal of Fermentation and Bioengineering, 1996, vol. 81, Issue 3, pp. 197-205.

Park, S., et al., "Oxaloacetate and malate production in engineered *Escherichia coli* by expression of codon-optimized phosphoenolpyruvate carboxylase2 gene from Dunaliella salina", Bioprocess Biosyst Eng., 2013, vol. 36, Issue 1, pp. 127-131.

Pryzbylski, D., et al., "Synthesis of the building block 2-hydroxyisobutyrate from fructose and butyrate by Cupriavidus necator H16", Appl. Microbial. Biotechnol., 2013, vol. 97, 20, pp. 8875-8885.

Qi et al., "Model-driven redox pathway manipulation for improved isobutanol production in Bacillus subtilis complemented with experimental validation and metabolic profiling analysis" PLoS ONE, 2014, vol. 9, Issue 4, : e93815, pp. 1-11.

Raberg, M., "Ralstoni a eutropha H16 in progress: applications beside PHAs and establishment as production platform by advanced genetic tools", Critical Reviews in Biotechnology, vol. 38, Dec. 12, 2017 (Dec. 12, 2017), pp. 494-510.

Raberg, M., et al., "A closer look on the polyhydroxybutyrate-(PHB-) negative phenotype of Ralstonia eutropha PHB-4" PLoS One, 2014, vol. 9, Issue 5, pp. 11.

Rosa, L.T., et al., "Tripartite ATP-Independent Periplasmic (TRAP) Transporters and Tripartite Tricarboxylate Transporters (TTT): From Uptake to Pathogenicity", Frontiers in Microbiology, 2018, vol. 8, pp. 16.

Russell, J.B., "The Energy Spilling Reactions of Bacteria and Other Organisms", Journal of Molecular Microbiology Biotechnology, vol. 13, No. 1, 2007, pp. 1-11.

Sanchez, A.M., et al., "Effect of overexpression of a soluble pyridine nucleotide transhydrogenase (UdhA) on the production of poly(3-hydroxybutyrate) in *Escherichia coli*" Biotechnol Prog., 2006, vol. 22, Issue 2, pp. 420-425.

Saur, U., et al., "The PEP-pyruvate-oxaloacetate node as the switch point for carbon flux distribution in bacteria", FEMS Microbiology Reviews, 2005, vol. 29, Issue 4, pp. 765-794.

Schlegel, H.G., et al., "Formation of the Dehydroganses for Lactate, Ethanol and Butanediol in the Strictly Aerobi Bacterium Alcaligene eutrophus" Microbiology, 1980, vol. 117, pp. 475-481.

Schobert, P., et al., "Unusual C3 and C4 metabolism in the chemo-autotroph Alcaligenes eutrophus" Journal of Bacterialogy, 1984, vol. 159, Issue 1, pp. 167-172.

Schramke, h., et al., "Revisiting Regulation of Potassium Homeostasis in *Escherichia coli*: The Connection toPhosphate Limitation", Wiley Microbiologyopen, vol. 6, No. 3, 2017, pp. 1-16.

Schwartz, E., et al., "A proteomic view of the facultatively chemolithoautotrophic lifestyle of Ralstonia eutropha H16" Proteomics, 2009, vol. 9, Issue 22, pp. 5132-5142.

Segura, D., et al., "Inactivation of pycA, encoding pyruvate carboxylase activity, increases polybeta-hydroxybutyrate accumulation in Azotobacter vinelandii on solid medium" Appl Microbial Biotechnol, 2004, pp. 65, Issue 4, pp. 414-418.

Sekar, B.S., et al., "Co-production of hydrogen and ethanol from glucose in *Escherichia coli* by activation of pentose-phosphate pathway through deletion of phosphoglucose somerase (pgi) and overexpression of glucose-6-phosphate dehydrogenase (zwf) and 6-phosphogluconate dehydrogenase ( gnd)", Biotechnology for Biofuels, 2017, vol. 10, 85, pp. 12.

Shang et al., "Poly(3-Hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-1419.

Shively, J.M., et al., "Something From Almost Nothing: Carbon Dioxide Fixation in Chemoautotrophs", Annu. Rev. Microbiol., vol. 52 ,1998, pp. 191-230.

Silva, F., et al., "Impact of nitrogen feeding regulation on polyhydroxyalkanoates production by mixed microbial cultures", New Biotechnology, vol. 37, 2017, pp. 90-98.

Steinbuchel, A., et al., "A multifunctional fermentative alcohol dehydrogenase from the strict aerobe Alcaligenes eutrophus: purification and properties" Eur J Biochem, 1984, vol. 141, Issue 3, pp. 555-564.

Stokke, R., et al., "Biochemical characterization of isocitrate dehydrogenase from Methylococcus capsulatus reveals a unique NAD+-dependent homotetrameric enzyme" Arch Microbiol., 2007, vol. 187, Issue 5, pp. 361-370.

Tan, Z., et al. "Activating phosphoenolpyruvate carboxylase and phosphoenolpyruvate carboxykinase in combination for improvement of succinate production" Appl. Environ. Microbiol, 2013, vol. 79, Issue 16, pp. 4838-4844.

(56) References Cited

OTHER PUBLICATIONS

Tanaka, K, et al., Production of Poly (D-3-Hydr0xybutyrate) From CO2, H2, and O2 by High Cell Density Autotropic Cultivation of Alcaligenes Eutrophus Biotechnology and Bioengineering, Wiley, vol. 45, No. 3, (Feb. 5, 1995), XP000489583, Feb. 5, 1995, 268-275.

Vemuri, G.N., et al., "Physiological response of central metabolism in *Escherichia coli* to deletion of pyruvate oxidase and introduction of heterologous pyruvate carboxylase" Biotechnology and Bioengineering, 2005, vol. 90, Issue 1 pp. 64-76.

Vollbrecht, D., et al., "Excretion of Metabolites by Hydrogen Bacteria I. Autotrophic and Heterotrophic Fermentations" European Journal of Applied Microbiology and Biotechnology, 1978, vol. 6, Issue 2, pp. 145-155.

Vollbrecht, D., et al., "Excretion of Metabolites by Hydrogen Bacteria II. Influence of Aeration, pH, Temperature, and Age of Cells", European Journal of Applied Microbiology and Biotechnology, 1978, vol. 6, Issue 2, pp. 157-166.

Vollbrecht, D., et al., "Excretion of Metabolites by hydrogen Bacteria III. D(-)-3-hydroxybutanoate", European J. Appl. Microbiol. Biotechnol., 1979, vol. 7, pp. 259-266.

Vollbrecht, D., et al., "Excretion of Metabolites by Hydrogen Bacteria IV. Respiration Rate-Dependent Formation of Primary Metabolites and of Poly-3-hydroxybutanoate", Eropean Journal of Applied Microbiology and Biotechnology, 1979, vol. 7, Issue 3, pp. 267-276.

Volodina, E., et al., "Characterization of propionate CoA-transferase from Ralstonia eutropha HI6", Appl Microbial Biotechnol., 2014, vol. 98, Issue 8, pp. 3579-3589.

Wang, F., et al., "Poly(3-Hydroxybutyrate) Production with High Productivity and High Polymer Content by a Fed-Bath Culture of Alcaligene lat us under Nitrogen Limitation", Applied and Environmental Microbiology, 1997, vol. 63, No. 9, pp. 3703-3706.

Wang, R., et al., "Isocitrate dehydrogenase from *Streptococcus mutans*: biochemical properties and evaluation of a putative phosphorylation site at Ser102" PLoS One, 2013, vol. 8, Issue 3, e58918.

Weiden et al., "Cation Transport in *Escherichia coli* Vii. Potassium Requirement for Phosphate Uptake", The Journal of General Physiology, vol. 50, No. 6, 1967, pp. 1641-1661.

Winnen, B., et al., "The tripartite tricarboxylate transporter (TTT) family" Res. Microbial., 2003, vol. 154, Issue 7, pp. 457-465.

Wu, M-C., et al., "A Novel Type II NAD+-Specific Isocitrate Dehydrogenase from the Marine Bacterium Congregibacter litoralis KT71" PLoS One., 2015, vol. 10, Issue 5, pp. 1-17.

Youngquist et al., "Functional Genomics Analysis of Free Fatty Acid Production under Continuous PhosphateLimiting Conditions", J. Ind. Microbial. Biotechnol., vol. 44, May 2017, pp. 759-772.

Zhu, J., et al., "Factors for promoting polyhydroxyalkanoate (PHA) synthesis in bio-nutrient-removal and recovery system", 4th International Conference on nvironmental Systems Research (ICESR 2017) Conference paper, 2018, pp. 1-4.

Ziesack, M. et al., "Chimeric Fatty Acyl-Acyl Carrier Protein Thioesterases Provide Mechanistic Insight into Enzyme Specificity and Expression", Applied and Environmental Microbiology, vol. 84, No. 10, Mar. 16, 2018, pp. 12.

Anderson and Dawes "Occurrence, metabolism, metabolic role, and industrial uses of bacterial polyhydroxyalkanoates" Microbiol. Rev. 1990 54: 450-72.

Brigham et al. "Whole-genome microarray and gene deletion studies reveal regulation of the polyhydroxyalkanoate production cycle by the stringent response in Ralstonia eutropha H16" Applied and Environmental Microbiology 2012 78(22) :8033-8044.

Brown et al. "Nitrogen stress response and stringent response are coupled in *Escherichia coli*". Nat. Comm. 2014 5:4115.

Byrd et al. "Bacterial Control of Agromyces ramosus in soil" Can J Microbiol 1985 31:1157-1163.

Ding et al. "Glycerol utilization by Rhizobium leguminosarum requires an ABC transporter and affects competition for nodulation" Microbiology 2012 158:1369-1378.

Gao et al. "Lactate utilization is regulated by the FadR-type regulator LldR in Pseudomonas aeruginosa" Journal of Bacteriology 2012 194:2687-269.

Hauryliuk et al. "Recent functional insights into the role of (p)ppGpp in bacterial physiology" Nature Reviews Microbiology 2015 13:298-309.

Juengert et al. "Absence of ppGpp Leads to Increased Mobilization of Intermediately Accumulated Poly(3-Hydroxybutyrate) in Ralstonia eutropha H16" Applied and Environmental Microbiology 2017 83(13) :e00755-17.

Kaddor and Steinbuchel. "Effects of homologous phosphoenolpyruvate-carbohydrate phosphotransferase system proteins on carbohydrate uptake and poly(3-Hydroxybutyrate) accumulation in Ralstonia eutropha H16" Appl. Environ. Microbiol. 2011 77:3582-3590.

Kaddor and Steinbuchel "Implications of various phosphoenolpyruvate-carbohydrate phosphotransferase system mutations on glycerol utilization and poly(3-hydroxybutyrate) accumulation in Ralstonia eutropha H16" AMB Express 2011 1:16.

Karstens et al. "Phosphotransferase protein EIIANtr interacts with SpoT, a key enzyme of the stringent response, in Ralstonia eutropha H16" Microbiology 2014 160:711-722.

Kazakov et al. "Comparative genomics of regulation of fatty acid and branched-chain amino acid utilization in proteobacteria" Journal of Bacteriology 2009 191:52-64.

Krausse et al. "Essential role of the hprK gene in Ralstonia eutropha H16" J Mol Microbiol Biotechnol 2009 17:146-152.

Lardi et al. "σ54-Dependent Response to Nitrogen Limitation and Virulence in Burkholderia cenocepacia Strain H111" Appl. Environ. Microbiol. 2015 81(12) : 4077-4089.

Leyn et al. "Control of proteobacterial central carbon metabolism by the HexR transcriptional regulator: a case study in Shewanella oneidensis" Journal of Biological Chemistry 2011 286(41) : 35782-35794.

Leyn et al. "Comparative genomics and evolution of transcriptional regulons in Proteobacteria" Microbial Genomics 2016 1-15.

Liu et al. "Comparative analysis of genes frequently regulated by drugs based on connectivity map transcriptome data" PLoS One 2017 12(6) : e0179037.

Lu et al. "Studies on the production of branched-chain alcohols in engineered Ralstonia eutropha" Appl Microbiol Biotechnol 2012 96:283-297.

Makkar, N.S. & Casida, L.E. "*Cupriavidus necator* gen. nov., sp. nov.: a Nonobligate Bacterial Predator of Bacteria in Soil" Int. J. of Systematic Bacteriology 1987 37(4) : 323-326.

Obruca et al. "Application of random mutagenesis to enhance the production of polyhydroxyalkanoates by Cupriavidus necator H16 on waste frying oil" World J Microbiol Biotechnol 2013 29:2417-2428.

Olaya-Abril et al. "Poly(3-hydroxybutyrate) hyperproduction by a global nitrogen regulator NtrB mutant strain of Paracoccus denitrificans PD1222" FEMS Microbiology Letters 2008 365:fnx251.

Persuhn et al. "The transcriptional activator NtrC controls the expression and activity of glutamine synthetase in Herbaspirillum seropedicae" FEMS Microbiology Letters 2000 192 217-221.

Pohlmann et al. "Genome sequence of the bioplastic-producing "Knallgas" bacterium Ralsonia eutropha H16" Nature Biotechnology 2007 1-6.

Sacamboio et al. "The transcriptional regulator NtrC controls glucose-6-phosphate dehydrogenase expression and polyhydroxybutyrate synthesis through NADPH availability in Herbaspirillum seropedicae" Scientific Reports 2017 7:13546.

Sillman, C. E. & Casida, L. E. "Isolation of nonobligate bacterial predators of bacteria from soil" Can J Microbiol 1986 32:760-762.

Sun et al. "The ntrB and ntrC genes are involved in the regulation of poly-3-hydroxybutyrate biosynthesis by ammonia in *Azospirillum brasilense* Sp7" Appl. Environ. Microbiol. 2000 66(1):113-117.

Sun et al. "Involvement of glnB, glnZ, and glnD genes in the regulation of poly-3-hydroxybutyrate biosynthesis by ammonia in *Azospirillum brasilense* Sp7" Appl. Environ. Microbiol. 2002 68(2):985-988.

(56) References Cited

OTHER PUBLICATIONS

Valderrama et al. "AccR is a master regulator involved in carbon catabolite repression of the anaerobic catabolism of aromatic compounds in *Azoarcus* sp. CIB" Journal of Biological Chemistry 2014 289(4):1892-1904.
Weinberg et al. "Identification of 22 candidate structured RNAs in bacteria using the CMfinder comparative genomics pipeline" Nucleic Acids Research 2007 35:4809-4819.
Zeph, L.E. & Casida, L.E. "Gram-negative versus gram-positive (actinomycete) nonobligate bacterial predators of bacteria in soil" Applied and Environmental Microbiology 1986 52(4) :819-823.
Invitation to Pay Additional Fees and, Where Applicable, Protest Fee in PCT/US2019/029817 dated Aug. 1, 2019.
Non-final office action received for U.S. Appl. No. 16/399,145, dated Aug. 12, 2020, 16 pages.
Alagesan, S., et al., "13C-assisted metabolic flux analysis to investigate heterotrophic and mixotrophic metabolism in Cupriavidus necator H16", Metabolomics, 2018, vol. 14, Issue 9, pp. 9.
Alagesan, S., et al., "Functional genetic elements for controlling gene expression in Cupriavidus necator H16", Applied and Environmental Microbiology,vol. 84, Oct. 2018 (Oct. 2018), pp. 1-17.
Atlic et al., "Continuous Production of Poly([R]-3-Hydroxybutyrate) by Cupriavidus Necator in a Multistage Bioreactor Cascade", Appl Microbial Biotechnology, vol. 91, 2011, pp. 295-304.
Bramer, C.O., "The malate dehydrogenase of Ralstonia eutropha and functionality of the C(3)/C(4) metabolism in a Tn5-induced mdh mutant", FEMS Microbiol Letters, Jul. 2, 2002, vol. 212, Issue 2, pp. 159-164.
Brandt, U., et al., "Elevated poly(3-hydroxybutyrate) synthesis in mutants of Ralstonia eutropha HI6 defective in lipopolysaccharide biosynthesis" Applied Microbiology and Biotechnology, 2012, vol. 95, pp. 471-483.
Brigham, C.J., et al., "Correction for Whole-genome microarray and gene deletion studies reveal regulation of the polyhydroxyalkanoate production cycle by the stringent response in Ralstonia eutropha H16", Appl Environ Microbiol., 2017, vol. 83, Issue 15, pp. 1-2.
Bruland et al. "Unravelling the C3/C4 carbon metabolism in Ralstonia eutropha H16" Journal of Applied Microbiology 2010 109:79-90.
Byrd, J.J., et al., "Bacterial control of Agromyces ramosus in soil" Canadian Journal of Microbiology, 1985, vol. 31, pp. 1157-1163.
Chae, T.U., et al., "Metabolic engineering of *Escherichia coli*for the production of four-, five- and six-carbon lactarns Metabolic Engineering", Academic Press, Us, vol. 41 ,Apr. 5, 2017, pp. 82-91.
Chakravarty, J., et al., "Solvent production by engineered Ralstonia eutropha: channeling carbon to biofuel", Applied Microbiology and Biotechnology, vol. 102, Apr. 29, 2018 (Apr. 29, 2018), pp. 5021-5031.
Chen, R., et al., "A highly active decarboxylating dehydrogenase with rationally inverted coenzyme specificity", PNAS, 1996, vol. 92, Issue 25, pp. 11666-11670.
Chen, R., et al. "Redesigning secondary structure to invert coenzyme specificity in isopropylmalate dehyrogenase" PNAS, 1996, vol. 93, pp. 12171-12176.
Choi, J.C., et al. "Modulation of 3-hydroxyvalerate molar fraction in poly(3-hydroxybutyrate-3-hydroxyvalerate) using Ralstonia eutropha transformant co-amplifying phbC and NADPH generation-related zwf genes", Enzyme and Microbial Technology, 2003, vol. 32, Issue 1, pp. 178-185.
Cramm, R. J. "Genomic view of energy metabolism in Ralstonia eutropha H16", Journal of Molecular Microbiology and Biotechnology, 2009, vol. 16, pp. 38-52.
Darani, K.K., et al., "Simulation of bioreactors for poly(3-hydroxybutyrate) production from natural gas", Iranian Journal of Chemistry and Chemical Engineering, vol. 39, 2018, pp. 1-24.
Doberstein, C., et al., "Polythioester synthesis in Ralstonia eutropha H16: novel insights into 3,3'- thiodipropionic acid and 3,3'-dithiodipropionic acid catabolism" Journal of Biotechnology, 2014, vol. 184, pp. 187-198.

Du et al., "Effects of Environmental Conditions on Cell Growth and Poly-B-Hydroxybutyrate Accumulation in Alcaligenes Eutrophus", World Journal of Microbiology & Biotechnology, vol. 16, 2000, pp. 9-13.
Eggers et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, No. 24,Dec. 2014, pp. 7702-7709.
Frng, Y., et al., "Tuning of acyl-ACP thioesterase activity directed for tailored fatty acid synthesis", Applied Microbiology and Biotechnology, Springer, De, vol. 102, No. 7 ,Feb. 22, 2018, pp. 3173-3182.
Girdhar, A., et al., "Process Parameters for Influencing Polyhyroxyalkanoate Producing Bacterial Factories: An Overview", Petroleum & Environmental Biotechnology, 2013, vol. 4, Issue 5, pp. 9.
Grousseau, E., et al., "Isopropanol production with engineered Cupriavidus necator as bioproduction platform" Appl Microbiol Biotechnol, 2014, vol. 98, pp. 4277-4290.
Gyaneshwar et al., "Sulfur and Nitrogen Limitation in *Escherichia coli* K-12: Specific Homeostatic Responses", Journal of Bacteriology, vol. 187, No. 3, Feb. 2005, pp. 1074-1090.
Hanko, E.K.R., et al., "Characterisation of a 3-hydroxypropionic acid-inducible system from Pseudomonas putida for orthogonal gene expression control in *Escherichia coli* and Cupriavidus necator", Scientific Reports, vol. 7, 2017, pp. 1-12.
Haushalter, R.W., et al., "Production of Odd-Carbon Dicarboxylic Acids in *Escherichia coli* Using an Engineered Biotin-Fatty Acid Biosynthetic Pathway" Journal of the American Chemical Society, vol. 139, No. 13 ,Mar. 21, 2017, pp. 4615-4618.
Horvat et al., "Mathematical Modelling and Process Optimization of a Continuous 5-Stage Bioreactor Cascade for11 Production of Poly[-(R)-3-Hydroxybutyrate] by Cupriavidus Necator", Bioprocess Biosyst Eng, vol. 36, 2013, pp. 1235-1250.
Hun-Suk Song et al: Enhanced isobutanolproduction from acetate by combinatorialoverexpression of acetyl-CoA synthetaseand anaplerotic enzymes in engineered*Escherichia coil*, Biotechnology and Bioengineering,vol. 115, May 2, 2018 (May 2, 2018), pp. 1971-1978.
Lenczak, J.L., et al., "High cell density strategy for poly(3-hydroxybutyrate) production by Cupriavidus necator", Brazilian Journal of Chemical Engineering, 2011, vol. 28, Issue 4, pp. 585-596.
Inoue, H., et al., "Biochemical and molecular characterization of the NAD(+)-dependent isocitrate dehydrogenase from the chemolithotrophAcidithiobacillus thiooxidans", FEMS Microbial Letters, 2002, vol. 214, Issue 1, pp. 127-132.
International Search Report and Written Opinion for International Application Serial No. PCT/US2019/025189, dated Jul. 2, 2019, pp. 12.
International Search Report and Written Opinion for International Application Serial No. PCT/US2019/025194, dated Aug. 22, 2019, pp. 24.
International Search Report and Written Opinion for International Application Serial No. PCT/US2019/025202, dated Jul. 30, 2019, pp. 15.
International Search Report and Written Opinion for International Application Serial No. PCT/US2019/025211, dated Jul. 29, 2019, pp. 16.
International Search Report and Written Opinion for International Application Serial No. PCT/US2019/025218, dated Sep. 5, 2019, pp. 17.
International Search Report and Written Opinion for International Application Serial No. PCT/US2019/029973 dated Jul. 23, 2019, dated Jul. 23, 2019, 5 pgs.
International Search Report and Written Opinion in PCT/US2019/029795 dated Jul. 11, 2019, pp. 10.
International Search Report and Written Opinion in PCT/US2019/029817 dated Sep. 23, 2019.
International Search Repot and Written Opinion in PCT/US2019/029827 dated Sep. 23, 2019.
International Search Report and Written Opinion in PCT/US2019/029956 dated Aug. 13, 2019.

(56) References Cited

OTHER PUBLICATIONS

Invitation to Pay Additional Fees and, Where Applicable, Protest Fee in PCT/082019/029798 dated Jul. 22, 2019.
Invitation to Pay Additional Fees and, WhereApplicable, Protest Fee in PCT/US2019/029827 datedJul. 23, 2019.
Jhonson, A., et al., "An engineered constitutive promoter set with broad activity range for Cupriavidus necator H16", ACS Synthetic Biology, vol. 7, Jun. 27, 2018 (Jun. 27, 2018), pp. 1918-1928.
Joris, Beld, et al. "Evolution of acyl-ACP thioesterases and [beta]-ketoacyl-ACP synthases revealed by protein-protein Interactions", Journal of Applied Phycology, vol. 26, No. 4 ,Nov. 22, 2013, pp. 1619-1629.
Justyna Mozejko-Ciesielska et al: "Bacterial polyhydroxyalkanoates: Still fabulous ?", Microbiological Research, vol. 192, 2016, pp. 271-282.
Katalin Kovacs et al: Metabolic engineering of Cupriavidus necator H16 for the sustainable production of C3 and C5 monomers and polymers,Clnet Conference 4, Jan. 20-23, 2019 Conference paper (Abstract), 2019, p. 26.
Kim et al. "Effect of overexpression of Actinobacillus succinogenes phosphoenolpyruvate carboxykinase on succinate production in *Escherichia coli*" Applied and Environmental Microbiology, 2004, vol. 70, Issue 2, pp. 1238-1241.
Kluge, J., et al., "Inducible promoters and functional genomic approaches for the genetic engineering of filamentous fungi", Applied Microbiology and Iotechnology, vol. 102, Jun. 2, 2018 (Jun. 2, 2018), pp. 6357-6372.
Koller et al., "Potential and Prospects of Continuous Polyhydroxyalkanoate (PHA) Production", Bioengineering,May 29, 2015, pp. 94-121.
Koller, M., "A review on established and emerging fermentation schemes for microbial production of polyhydroxyalkanoate (PHA) biopolyesters", Fermentation,vol. 4, Apr. 23, 2018 (Apr. 23, 2018), pp. 1-30.
Koller, M., et al., "Continuous production mode as a viable process-engineering tool for efficient poly (hydroxyalkanoate) (PHA) bioproduction", Chemical and Biochemical Product Engineering, vol. 28, Issue 1, 2014, pp. 65-77.
Kunasundari et al., "Revisiting the Single Cell Protein Application of Cupriavidus Necator H16 and Recovering Bioplastic Granules Simultaneously", Plos One, vol. 8, No. 10, Oct. 2013, 15 pages.
International Preliminary Report on Patentability in PCT/US2019/029817 dated Nov. 3, 2020.
Kizer L et al. Application of Functional Genomics to Pathway Optimization for Increased Isoprenoid Production. Applied andEnvironmental Microbiology. 2008. vol. 74, No. 10. p. 3229-3241. (Year: 2008).
Prather KLJ et al. De nova biosynthetic pathways: Rational design of microbial chemical factories. Current Opinion in Biotechnology. 2008. 19:468-47 4 (Year: 2008).
Singh RK et al. Protein Engineering Approaches in the Post-Genomic Era. 2017. Current Protein and Peptide Science. 18, 1-11. (Year: 2017).
Uniprot database, entry AOAOU2WHGO, Mar. 2016, 4 pages.
Zhang M et al. Propagated Perturbations from a Peripheral Mutation Show Interactions Supporting WW Domain Thermostablity.2018. Structure. 26, 1474-1485. (Year: 2018).
Cavalheiro, J., et al., "Poly(3-hydroxybutyrate) production by Cupriavidus necator using waste glycerol", Process Biochemistry, vol. 44, 2009, pp. 509-515.

\* cited by examiner

US 11,098,381 B2

MATERIALS AND METHODS FOR CONTROLLING REGULATION IN BIOSYNTHESIS IN SPECIES OF THE GENERA *RALSTONIA* OR *CUPRIAVIDUS* AND ORGANISMS RELATED THERETO

This patent application claims the benefit of priority from U.S. Provisional Patent Application Ser. No. 62/665,790 filed May 2, 2018, teachings of which are herein incorporated by reference in their entirety.

FIELD

The present invention relates to methods for increasing carbon-based chemical product yield in an organism by modifying one or more genes involved in a stringent response and/or in a regulatory network, nonnaturally occurring organisms having increased carbon-based chemical product yield, and methods for use in production of carbon-based chemical products.

BACKGROUND

Organisms have a limited ability to control their environment and therefore, may respond to environmental conditions with biochemical and/or metabolic changes. Such changes have been reported to include phenotypic changes, wherein a microorganism responds to environmental changes by expressing certain sets of genes, resulting in functional and structural adjustments within the microorganism to adapt to the changing environmental conditions. Microorganisms have a wide range of regulatory mechanisms to sense and respond to changing environmental conditions, and this confers on them a high level of versatility.

Replacement of traditional chemical production processes relying on, for example fossil fuels and/or potentially toxic chemicals, with environmentally friendly and/or sustainable solutions is being considered, including work to identify suitable building blocks for such use in the manufacturing of such chemicals. In *Cupriavidus necator*, polyhydroxybutyrate (PHB) is a key intracellular carbon and energy storage compound enabling cells to survive periods of starvation, and other stressful conditions. In response to such environmental variables, regulators alter global gene expression and metabolism and under appropriate conditions this can result in the storage of carbon and energy as PHB (Anderson and Dawes, Microbiol. Rev. 1990 54: 450-72).

SUMMARY

Methods for increasing product yield of organisms and organisms capable of increased product yield are provided.

An aspect of the present invention relates to methods for increasing carbon-based chemical product yield in an organism. The methods comprise modulating activity of one or more polypeptides or functional fragments thereof involved in a stringent response and/or in a regulatory network of an organism selected from a species of *Cupriavidus* or *Ralstonia* with diminished polyhydroxybutyrate synthesis or an organism with properties similar thereto.

In one nonlimiting embodiment, one or more modified genes limiting intracellular glutamine are modified.

In one nonlimiting embodiment, one or more genes selected from glutamate dehydrogenase (gdhA; H16_A0471, H16_B1945, or H16_A1356), glutamine synthetase (glnA; H16_A2335, H16_B0618 or H16_B2191) or glutamate synthase (gltAB; H16_A3430 or H16_A3431) are modified.

In one nonlimiting embodiment, one or more genes selected from GlnB (H16_A0320 and H16_0750), NtrB (H16_A2333), NtrC (H16_A2332), PtsN (H16_A0384), GlnD (H16_A2057), spoT1 (H16_A0955) and/or spoT2 (H16_A1337) are modified.

In one nonlimiting embodiment, one or more genes selected from NtrC (H16_A2332), RpoN/sigma 54 (H16_A0387), sigma 54 modulation protein S30EA (H16_A0386), or homologs thereof are modified.

In one nonlimiting embodiment, one or more genes affecting a signaling pathway leading to increased (p)ppGpp levels and induction of the stringent response in non-limiting culture conditions are modified.

In one nonlimiting embodiment, one or more modified genes involved in the regulatory network selected from FadP (H16_A0459), PsrA (H16_A3736), LldR (H16_B0094), GlpR (H16_A2504), AccR/BphQ (H16_A1372 or H16_A1373) and/or HexR (H16_A1177 or H16_B1210) and/or are involved in a regulatory network involving glycerol, the Ntr system and/or a sucA riboswitch are modified.

Another aspect of the present invention relates to a nonnaturally occurring organism capable of yielding a carbon-based chemical product. These nonnaturally occurring organisms comprise a species of *Cupriavidus* or *Ralstonia* with diminished polyhydroxybutyrate synthesis or an organism with properties similar thereto and a modification to one or more polypeptides or functional fragments thereof encoded by one or more genes involved in a stringent response and/or in a regulatory network of the organism.

In one nonlimiting embodiment, one or more genes limiting intracellular glutamine are modified in the nonnaturally occurring organism.

In one nonlimiting embodiment, one or more genes selected from glutamate dehydrogenase (gdhA; H16_A0471, H16_B1945, or H16_A1356), glutamine synthetase (glnA; H16_A2335, H16_B0618 or H16_B2191) or glutamate synthase (gltAB; H16_A3430 or H16_A3431) are modified.

In one nonlimiting embodiment, one or more genes selected from GlnB (H16_A0320 and H16_0750) NtrB (H16_A2333), NtrC (H16_A2332), PtsN (H16_A0384), GlnD (H16_A2057), spoT1 (H16_A0955) and/or spoT2 (H16_A1337) are modified.

In one nonlimiting embodiment, one or more genes selected from NtrC (H16_A2332), RpoN/sigma 54 (H16_A0387), sigma 54 modulation protein S30EA (H16_A0386), or homologs thereof are modified.

In one nonlimiting embodiment, one or more genes affecting a signaling pathway leading to increased (p)ppGpp levels and induction of the stringent response in non-limiting culture conditions are modified.

In one nonlimiting embodiment, one or more modified genes involved in the regulatory network selected from FadP (H16_A0459), PsrA (H16_A3736), LldR (H16_B0094), GlpR (H16_A2504), AccR/BphQ (H16_A1372 or H16_A1373) and/or HexR (H16_A1177 or H16_B1210) and/or are involved in a regulatory network involving glycerol, the Ntr system and/or a sucA riboswitch are modified.

Yet another aspect of the present invention relates to methods for producing a carbon-based chemical product. In these methods, a nonnaturally occurring organism of the present invention is fermented with a carbon source.

BRIEF DESCRIPTION OF THE FIGURES

FIG. 1A) and normalised isopropanol (IPA; FIG. 1B) after 48 hours of feeding regime. "Control" is a recombinant mutant of *C. necator* H16 where the PHBs pathway was replaced by the IPA pathway. ΔFadP is a recombinant mutant of *C. necator* H16 where the PHBs pathway was replaced by the IPA pathway and a fatty acid degradation regulator, FadP, was deleted. Both strains have consumed almost all fructose introduced in the system (FIG. 1C) and have exhausted all the nitrogen available (FIG. 1D). Data represent average of 3 biological replicates and error bars represent twice the standard deviation of the datasets.

DETAILED DESCRIPTION

Figure 1A:
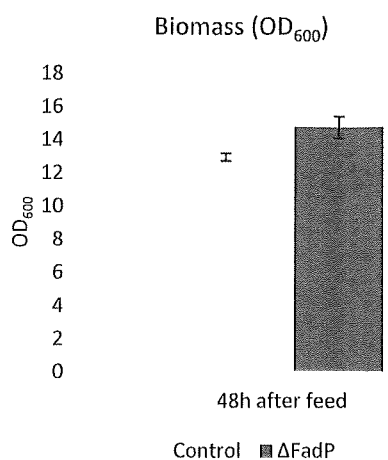
FIGS. 1A through 1D are bargraphs showing accumulation of biomass (OD at 600 nm.

This disclosure provides methods for increasing carbon-based chemical product yield in an organism via modification to one or more genes involved in a stringent response or in regulatory networks.

By "modification", "modifying" or "modify" for purposes of the present invention, it is meant that the gene is deleted, mutated, overexpressed or attenuated.

In certain aspects, the organism is modified by altering, engineering, or introducing one or more nucleic acid sequences within the organism. The altering of modifying of the nucleic acid sequences can be, for example and without limitation, via genetic engineering, by adaptive mutation, or by selective isolation of naturally occurring mutant strains.

In some nonlimiting embodiments, one or more enzymes or nucleic acids of the organism are modified via non-direct or rational enzyme design approaches with aims of improving activity, improving specificity, reducing feedback inhibition, reducing repression, improving enzyme solubility, changing stereo-specificity, or changing co-factor specificity. In some embodiments, the enzymes in the pathways outlined herein can be gene dosed (i.e., overexpressed by having a plurality of copies of the gene in the host organism), into the resulting genetically modified organism via episomal or chromosomal integration approaches. In some nonlimiting embodiments, genome-scale system biology techniques such as Flux Balance Analysis can be utilized to devise genome scale attenuation or knockout strategies for directing carbon flux. Attenuation strategies include, but are not limited to, the use of transposons, homologous recombination (double cross-over approach), mutagenesis, enzyme inhibitors, and RNA interference (RNAi). In some embodiments, fluxomic, metabolomic and transcriptomal data can be utilized to inform or support genome-scale system biology techniques, thereby devising genome-scale attenuation or knockout strategies in directing carbon flux. In some embodiments, the tolerance of the host microorganism to high concentrations of the extracellular product can be improved through continuous cultivation in a selective environment.

The modified nucleic acid sequences of the organism can include, for example, one or more enzymes, one or more promoters, one or more transcription factors, or combinations thereof. The modifications can be to nucleic acids encoding polypeptides functioning as a transhydrogenase, reductase, dehydrogenase, or hydrogenase enzyme or functional fragments thereof. The modifications can be to nucleic acids not directly involved in encoding polypeptides functioning as a transhydrogenase, reductase, dehydrogenase, or hydrogenase enzyme or functional fragments thereof, but indirectly affecting the polypeptides through the interconnected metabolic network and metabolic control strategy of the organism. The modification of the nucleic acid sequences can include one or more deletions, one or more substitutions, one or more insertions, or combinations thereof.

Enzymes with substitutions will generally have not more than 50 (e.g., not more than 1, not more than 2, not more than 3, not more than 4, not more than 5, not more than 6, not more than 7, not more than 8, not more than 9, not more than 10, not more than 12, not more than 15, not more than 20, not more than 25, not more than 30, not more than 35, not more than 40, or not more than 50) amino acid substitutions (e.g., conservative or non-conservative substitutions). This applies to any of the enzymes described herein and functional fragments thereof. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic, or acidic groups by another member of the same group can be deemed a conservative substitution. In contrast, a non-conservative substitution is a substitution of one amino acid for another with dissimilar characteristics. Deletion variants can, for example, lack 1, 2, 3, 4, 5, 6, 7, 8, 9, 10, 11, 12, 13, 14, 15, 16, 17, 18, 19, or 20 amino acid segments (of two or more amino acids) or non-contiguous single amino acids.

In one nonlimiting embodiment, modification of the organism is carried out by allele exchange. In this embodiment, genome edits are made in a *Cupriavidus* or *Ralstonia* organism with perturbed PHB synthesis or an organism with properties similar thereto by allele exchange (also referred to as allelic exchange). In one non-limiting embodiment, the organism is a AphaCAB H16 *C. necator* strain generated using allele exchange.

The term 'allele' is often used interchangeably with the term 'gene' more generally, and refers to a defined genomic locus. In allele exchange, a specific run of DNA sequence (i.e., the native allele) in a genome of an organism is literally exchanged for a recombinant, mutant, or synthetic run of DNA sequence (i.e., the recombinant allele). Depending on the nature of the recombinant allele, this allele exchange can result in a gene deletion, a gene substitution, or a gene insertion.

In one nonlimiting embodiment, recombinant/synthetic alleles can be constructed via gene synthesis and/or standard molecular biology techniques. These alleles are then cloned into a plasmid vector for transfer into the organism and execution of the allele exchange procedure.

In some nonlimiting embodiments, the organism is modified to include one or more exogenous nucleic acid sequences.

The term "exogenous" as used herein with reference to a nucleic acid (or a protein) and an organism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that nonnaturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In certain aspects, the organism is modified to include one or more functional fragments of enzymes, other polypeptides, or nucleic acids. The phrase "functional fragment" as used herein refers to a peptide fragment of a polypeptide or a nucleic acid sequence fragment encoding a peptide fragment of a polypeptide that has at least 25%, e.g., at least 30%, at least 40%, at least 50%, at least 60%, at least 70%, at least 75%, at least 80%, at least 85%, at least 90%, at least 95%, at least 98%, at least 99%, or at least 100% of the activity of the corresponding mature, full-length, polypeptide. The functional fragment can generally, but not always, be comprised of a continuous region of the polypeptide, wherein the region has functional activity.

The stringent response is triggered under stressful conditions, for example, nutrient starvation, and allows the cell to survive under different extreme environmental conditions. In one nonlimiting embodiment of the present invention, one or more genes involved in a stringent response of the organism are modified.

A nonlimiting example of altering genome regulators for stringent responses is limited nitrogen.

For example, in conditions of nitrogen deficiency levels of glutamine are low resulting in the uridylation of GlnB (H16_A0750, H16_A0320) by GlnD (H16_A2057). Unmodified GlnB stimulates the phosphatase activity of the kinase/phosphatase NtrB (H16_A2333), thus a consequence of GlnB uridylation is the phosphorylation of NtrC (H16_A2332), an enhancer binding protein, to its transcriptionally active form by the kinase NtrB. Activated NtrC binds to promoter regions and together with sigma 54 (RpoN H16_A0387) activates transcription from sigma 54 dependent promoters such as the promoter for glnA (H16_A2335), and in turn various effector response genes (Sacamboio et al. Scientific Reports 2017 7:13546; Lardi et al. Appl. Environ. Microbiol. 2015 81(12): 4077-4089; Persuhn et al. FEMS Microbiology Letters 2000 192 217-221; Liu et al. PLoS One 2017 12(6):e0179037). In *E. coli* this set of genes includes relA, providing a direct link between nitrogen limitation and the (p)ppGpp levels (Brown et al. Nat. Comm. 2014 5:4115). In one nonlimiting embodiment of the present invention, altered glutamine levels (nitrogen signal molecule) can be achieved by modifying glutamate dehydrogenase (gdhA1, gdhA2-H16_A0471; H16_B1945), glutamine synthetase (ginA1, glnA2, glnA3-H16_A2335; H16_B0618; H16_B2191), and/or glutamate synthase (gltD, gltB1-H16_A3430; H16_A3431). In one nonlimiting embodiment, the gene H16_A2335 is mutated or deleted.

In addition, the nitrogen regulatory system is encoded by uridyltransferase (glnD H16_A2057), trimeric signaling protein PII (glnB H16_A0750, H16_A0320), as well as the kinase NtrB (H16_A2333) and enhancer binding protein NtrC (H16_A2332). Deletion of the ntrC gene resulted in excess PHB production and an increase in the NADPH/NADP+ ratio in *Herbaspirillum seropedicae* (Sacamboio et al. Scientific Reports 2017 7:13546), while in *Azospirillum brasilense* deletion of ntrC or glnD results in higher PHB production (Sun et al. Appl. Environ. Microbiol. 2002 68(2):985-988; Sun et al. Appl. Environ. Microbiol. 2000 66(1):113-117). In *Paracoccus denitrificans*, mutation of the NtrB sensor kinase resulted in a strain with elevated PHB and acetyl-CoA levels (Olaya-Abril et al. FEMS Microbiology Letters 2008 365:fnx251).

In one nonlimiting embodiment of the present invention, one or more genes selected from glnB (H16_A0320 and/or H16_A0750), ntrB (H16_A2333), ntrC (H16_A2332), and glnD (H16_A2057) are modified.

Nitrogen sigma factor RpoN (sigma 54) has also been implicated in the response to nitrogen limitation and PHB production (Lardi et al. Appl. Environ. Microbiol. 2015 81(12)4077-4089). In one nonlimiting embodiment of the present invention, expression of sigma 54 (H16_A0387) or another form, sigma 54 modulation protein S30EA (H16_A0386) is attenuated.

The alarmone (p)ppGpp is another important signal molecule that induces stringent response in many bacterial species. It has been shown to alter transcription and is associated with stresses such as nitrogen limitation (Juengert et al. Applied and Environmental Microbiology 2017 83(13):e00755-17; Karstens et al. Microbiology 2014 160: 711-722; Hauryliuk et al. Nature Reviews Microbiology 2015 13:298-309). The alarmone ppGpp is a key signaling molecule in bacteria and is involved in regulating growth and stress responses. (p)ppGpp is synthesized from GTP by the action of RelA/Rel/SpoT enzymes which can catalyze the phosphorylation of GTP. Hydrolysis of (p)ppGpp back to GTP is catalyzed by Rel and SpoT (but not RelA). *C. necator* has SpoT-like and RelA-like genes. (p)ppGpp can exert its regulatory effect by several mechanisms including, but not limited to, alteration of GTP pool (changes promoter preference of RNAP), binding to RNAP; inhibition of protein biosynthesis, inhibition of DNA replication, inhibition of polyphosphate metabolism and inhibition of acid stress response. In *C. necator* (p)ppGpp levels are regulated by the activities of SpoT1 (p)ppGpp synthase/hydrolase (H16_A0955) and SpoT2 (p)ppGpp synthase (H16_A1337). *C. necator* strains lacking SpoT1 have increased levels of (p)ppGpp and increased PHB accumulation, while strains lacking both SpoT1 and SpoT2 have no detectable (p)ppGpp and low PHB levels (Juengert et al. Applied and Environmental Microbiology 2017 83(13):e00755-17).

The phosphotransferase system in *C. necator* is part of the system that regulates PHB production. In *C. necator* this system consists of EI (PtsI H16_A0326), HPr (PtsH H16_A0325), EIIA$^{Ntr}$(PtsN H16_A0384), EIIA$^{Man}$(PtsM H16_A0324) and HprK (H16_A0383) (Krausse et al. J Mol Microbiol Biotechnol 2009 17:146-152; Kaddor and Steinbuchel. Appl. Environ. Microbiol. 2011 77:3582-3590). Knockout of ptsN in *C. necator* results in increased accumulation of PHB, while knockouts of ptsI and ptsH result in a decrease in PHB. Unphosphorylated PtsN has also been shown to interact with the ppGpp synthase/hydrolase SpoT1 thus influencing (p)ppGpp levels and the stringent response (Karstens et al. Microbiology 2014 160:711-722).

In one nonlimiting embodiment of the present invention, the organism is modified to express either or both of the natural and/or non-native spoT genes (H16_A0955 and H16_A1337). In another nonlimiting embodiment of the present invention, spoT1 (H16_A0955) and/or spoT2 (H16_A1337) are mutated or deleted.

In one nonlimiting embodiment of the present invention, the organism is modified to attenuate expression of ptsN (H16_A0384).

In one nonlimiting embodiment of the present invention, one or more genes involved in a regulatory network of the organism are modified.

In one nonlimiting embodiment, FadP (H16_A0459) is modified. FadP is a TetR-like regulator located in the fatty acid degradation operon in *C. necator* H16 (H16_A0459-465) and is a potential repressor of fatty acid degradation pathways (Kazakov et al. Journal of Bacteriology 2009 191:52-64). Deletion of H16_A0459 is expected to upregulate β-oxidation pathways which is desired for improved growth and/or utilization of organic acids and mixtures thereof. Overexpression of H16_A0459 is expected to downregulate β-oxidation pathways, which is desired for production of fatty acid derived products. The predicted promoter motif of FadP is AATNGWACGAYCGTKCKNWT (SEQ ID NO:1). FadP is expected to regulate for example, but not limited to, H16_A0217 (thioesterase), H16_A0459-H160464 (beta-oxidation operon), H16_A0814-16 (electron transfer flavoprotein beta, electron transfer flavoprotein alpha, acyl-CoA dehydrogenase), H16_A1066-1068 (2×acyl-CoA dehydrogenase), H16_A1102-3 (3-HO-acyl-CoA dehydrogenase, enoyl-CoA hydratase), H16_A1445 (BktB), H16_A1519 (acyl-CoA ligase), H16_A1526-31 (beta-oxidation operon), H16_A2794 (acyl-CoA ligase) and H16_A3288 (acyl-CoA ligase).

Organisms with a mutation in the fadP gene are expected to exhibit improved utilization of fatty acids/mixtures containing fatty acids/mixotrophic growth. Further, removal of a FadP binding site in promoter regions of genes/operons will deregulate specific pathways or groups of genes thereby improving utilization of fatty acids/mixtures containing fatty acids/mixotrophic growth. Organisms with increased FadP expression and decreased beta-oxidation are expected to exhibit reduced degradation of fatty acids thus improving production of fatty acids/fatty acid derived products. Organisms with increased FadP expression and decreased beta-oxidation are also expected to reduce degradation of fatty acids for cleanup of mixed waste stream (e.g. removal of non-diacids from NVR to leave just adipic and/or glutaric acids). Organisms with increased FadP expression with mutated FadP binding sites to simultaneously reduce expression of specific beta-oxidation pathway genes and increase expression of others are useful in, for example, but not limited to, clean up of mixed waste stream (as above) or for production of fatty acid derived molecules while using, for example, but not limited to, oils or NVR as growth substrate.

In one nonlimiting embodiment, PsrA (H16_A3736) is modified. PsrA is a TetR family regulator and also regulates fatty acid pathways. PsrA is expected to regulate the fatty acid biosynthesis (FAB) operon (H16_A2569-2565) and its deletion is expected to upregulate FAB pathways resulting in more fatty acid production. Alternatively, when acting as a repressor, overexpression could reduce the FAB pathway.

Organisms with mutation in PsrA may exhibit increased production of fatty acids and fatty acid derived molecules or decreased production of fatty acids with increased production of other desired products via redirection of flux and/or increased availability of acetyl-CoA for other pathways.

In one nonlimiting embodiment, LldR is modified. LldR (H16_B0094) is a GntR family regulator and is a potential repressor of lactate dehydrogenase expression (H16_B0460, H16_B1817). H16_B0094 is adjacent to an operon which includes L-lactate permease (H16_B0090). Deletion of LldR is expected to upregulate lactate catabolism (Gao et al. Journal of Bacteriology 2012 194:2687-269; Leyn et al. Microbial Genomics 2016 1-15).

Organisms with mutated LldR or LldR binding sites are expected to exhibit increased utilization of lactate and production of products comprising organic acid mixtures that include lactate. Organisms with increased expression of LldR are expected to exhibit decreased utilization of lactate for improved production of lactate and lactate derived products.

In one nonlimiting embodiment, one or more genes involved in the regulatory network involving glycerol are modified. In one embodiment, the gene is GlpR (H16_A2504), which is co-localized with genes for glycerol kinase (glpK H16_A2507), glycerol-3-phosphate dehydrogenase (glpD H16_A2508), and an ABC transporter system (H16_A2498-2503) that is predicted to transport glycerol. The ABC transporter system encoded by H16_A2498-2503 has high identity (49%-73%) to a characterized glycerol transport system from *Rhizobium leguminosarum* (Ding et al. Microbiology 2012 158:1369-1378). In one nonlimiting embodiment, GlpR is deleted or expression is reduced thereby increasing glycerol utilization and/or improving utilization of mixtures containing glycerol. In one nonlimiting embodiment, GlpR is overexpressed thereby decreasing glycerol utilization. Modification of one or more genes involved in the regulatory network involving glycerol is expected to improve production of glycerol derived products such as 3-hydroxypropionate and 1,3,-propanediol. Further, organisms with glycerol uptake but no glycerol metabolism can be produced.

In one nonlimiting embodiment, one or more genes involved in the regulatory network involving catabolism of aromatic compounds are modified. In one nonlimiting embodiment, AccR and/or its corresponding sensor kinase is modified (Valderrama et al. Journal of Biological Chemistry 2014 289(4):1892-1904). In one nonlimiting embodiment, H16_A1372, the AccR response regulator and/or H16_A1373, its corresponding sensor kinase, are modified. Phosphorylation of AccR causes repression of genes involved in aromatic hydrocarbon catabolism and its modification is predicted to affect aromatic hydrocarbon degradation pathways. Further, AccR is predicted to regulate promoters for, for example, but not limited to, succinate dehydrogenase (H16_A2629-32), benzoate regulatory genes (H16_A1411; H16_B1915) and benzoyl-coA ligase (H16_A1412).

Organisms with mutated AccR and mutations in AccR binding sites are expected to exhibit improved biomass formation and improved utilization and formation of products of aromatic hydrocarbons and mixtures containing aromatic hydrocarbons. A nonlimiting example is terephthalic acid. Organisms with increased AccR, increased kinase and/or AccR with a super repressor mutation are expected to exhibit decreased utilization of aromatics and improved production of aromatic derived molecules.

Mutation of $Asp^{60}$ to the phosphomimetic Glu in the *Azoarcus* AccR results in a constitutively active AccR that is a super repressor of target genes (Valderrama et al. Journal of Biological Chemistry 2014 289(4):1892-1904). Organisms of the present invention modified to reduce or delete AccR are expected to exhibit increased aromatic utilization and mixtures containing aromatics. Organisms of the present invention with increased AccR expression or with a super repressor AccR (e.g. $Asp^{63}$ to Glu in H16_A1372) are expected to exhibit decreased aromatic utilization.

In one nonlimiting embodiment, HexR (Leyn et al. Microbial Genomics 2016 1-15; Leyn et al. Journal of Biological Chemistry 2011 286(41): 35782-35794) is modified. In one nonlimiting embodiment, HexR genes from *C. necator* H16, H16_A1177 and/or H16_B1210 are modified. H16_A1177 is divergently transcribed from genes encoding the ED pathway enzymes phosphogluconate dehydratase (edd H16_A1178) and gluconate kinase (H16_A1179). H16_B1210 is divergently transcribed from genes encoding the ED pathway enzymes 2-keto-3-deoxygluconate kinase (H16_B1212) and 2-keto-3-deoxy-6-phosphogluconate aldolase (eda H16_B1213). HexR is an Entner-Doudoroff (ED) pathway regulator, the major sugar degradation route in *C. necator*. Overexpression of HexR is expected to alter carbon preferences (gluconate/glucose) in organisms improving or reducing flux through the ED pathway.

In one nonlimiting embodiment, one or more genes involved in the regulatory network involving riboswitches are modified. Riboswitches are described, for example, by Weinberg et al. (Nucleic Acids Research 2007 35:4809-4819). In one nonlimiting embodiment, a sucA riboswitch is modified. In one nonlimiting embodiment, a riboswitch comprising the nucleic acid sequence of TTGTTTGC-GATCCGCTAACCGGTCAAGCCGTGTCGCG-GAAGGTTGAATAACCCGCTGAACTC CGGCAT-TCCCGGAGAATAGTGAGCGTCCCATGATG (SEQ ID NO:2) is modified. In one nonlimiting embodiment, a riboswitch upstream of H16_A2325, 2-oxoglutarate dehydrogenase, is modified.

Organism with mutations of a sucA riboswitch and deregulation of 2-oxo-glutarate dehydrogenase are expected to exhibit increased production of products derived from TCA cycle intermediates.

Nonlimiting examples of nucleic acid and amino acid sequences for the above-described genes are set forth in the Sequence Appendix. However, as will be understood by the skilled artisan upon reading this disclosure, the present invention is not limited to these particular gene sequences and is also inclusive of nucleic acid and amino acid sequences for polypeptides with similar enzymatic activities exhibiting at least 50%, 60%, 70%, 75%, 80%, 85%, 90%, 91%, 92%, 93%, 94%, 95%, 96%, 97%, 98%, 99% or 99.5% sequence identity to sequences set forth in the Sequence Appendix and functional fragments thereof.

The percent identity (and homology) between two amino acid sequences as disclosed herein can be determined as follows. First, the amino acid sequences are aligned using the BLAST 2 Sequences (Bl2seq) program from the stand-alone version of BLAST containing Blast+2.9.0. This stand-alone version of BLAST can be obtained from the U.S. government's National Center for Biotechnology Information web site (www with the extension ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be followed for nucleic acid sequences except that blastn is used.

Once aligned, the number of matches is determined by counting the number of positions where an identical amino acid residue is presented in both sequences. The percent identity (and homology) is determined by dividing the number of matches by the length of the full-length polypeptide amino acid sequence followed by multiplying the resulting value by 100. It is noted that the percent identity (homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

By "carbon-based chemical product" as used herein, it is meant to include C3 to C12 alkenes, alcohols, diols, monoacids, diacids, hydroxyacids, amino acids and diamines. In one nonlimiting embodiment, the carbon-based chemical product may be any C6-C12 difunctional aliphatic fatty acid or derivative thereof including, but not limited to, C6-C12 amino acids, C6-C12 diamines, C6-C12 hydroxyacids, C6-C12 diols, and C6-C12 diacids. Nonlimiting examples of carbon-based chemical products produced in accordance with this disclosure include 1,3-propanediol, 1,2-propanediol, methionine, threonine, lysine, glutamic acid, tryptophan, aspartic acid, leucine, isoleucine, valine, citric acid, maleic acid, succinic acid, isoprene, linalool, limonene, 3-hydroxypropanoic acid, malonic acid, lactic acid, n-butanol, 2-butanone, butadiene, 2-3 butanediol, 1-3 butanediol, benzoic acid, 1,4-benzenediamine, benzeneamine, pyridine, vanillin, hydroquinone, 1,4-diaminobutane, 2-hydroxyisobutyric acid, itaconic acid, 3-hydroxybutyrate and nylon intermediates.

In some nonlimiting embodiments, the organism has been modified to exhibit an increased synthesis of the extracellular product relative to that of the corresponding wild type organism.

In some nonlimiting embodiments, the carbon-based chemical product includes pimelic acid, 7-aminoheptanoate, 7-hydroxyheptanoate, heptamethylenediamine, 1,7-heptanediol, or a combination thereof. Additional descriptions of the synthesis of these carbon-based chemical products with *Ralstonia, Cupriavidus*, or an organism similar thereto can be found in U.S. Pat. No. 10,196,657, the disclosure of which is incorporated by reference herein in its entirety for all purposes.

In some nonlimiting embodiments, the carbon-based chemical product includes 1,4-butanediol, putrescine, 4-hydroxybutyrate, 4-aminobutyrate, or a combination thereof. Additional descriptions of the synthesis of these carbon-based chemical products with *Ralstonia, Cupriavidus*, or an organism related thereto can be found in U.S. Pat. Nos. 10,072,150 and 9,637,764, the disclosures of which are incorporated by reference herein in their entirety for all purposes.

In some nonlimiting embodiments, the carbon-based chemical product includes glutaric acid, 5-aminopentanoic acid, cadaverine (also known as 1,5 pentanediamine), 5-hydroxypentanoic acid, 1,5-pentanediol, glutarate semialdehyde (also known as 5-oxopentanoate), or a combination thereof. Additional descriptions of the synthesis of these carbon-based chemical products with *Ralstonia, Cupriavidus*, or an organism related thereto can be found in U.S. Pat. No. 9,920,339, the disclosure of which is incorporated by reference herein in its entirety for all purposes.

In some nonlimiting embodiments, the carbon-based chemical product includes isoprene. Additional descriptions of the synthesis of this carbon-based chemical product with *Ralstonia, Cupriavidus*, or an organism related thereto can be found in U.S. Pat. No. 9,862,973, the disclosure of which is incorporated by reference herein in its entirety for all purposes.

In some nonlimiting embodiments, the carbon-based chemical product includes adipic acid, 6-aminohexanoic acid, hexamethylenediamine, caprolactam, 1,6-hexanediol, or a combination thereof. Additional descriptions of the synthesis of these carbon-based chemical products with *Ralstonia, Cupriavidus*, or an organism related thereto can be found in U.S. Pat. No. 9,580,733, the disclosure of which is incorporated by reference herein in its entirety for all purposes.

For products of the present invention containing carboxylic acid groups such as organic monoacids, hydroxyacids, aminoacids and dicarboxylic acids, these products may be formed or converted to their ionic salt form when an acidic proton present in the parent product either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate and/or bicarbonate, sodium hydroxide, ammonia and the like. The salt can be isolated as is from the system as the salt or converted to the free acid by reducing the pH to below the lowest pKa through addition of acid or treatment with an acidic ion exchange resin.

For products of the present invention containing amine groups such as but not limited to organic amines, amino acids and diamine, these products may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. The salt can be isolated as is from the system as a salt or converted to the free amine by raising the pH to above the lowest pKa through addition of base or treatment with a basic ion exchange resin. Acceptable inorganic bases are known in the art and include aluminum hydroxide, calcium hydroxide, potassium hydroxide, sodium carbonate and/or bicarbonate, ammonia, sodium hydroxide, and the like.

For products of the present invention containing both amine groups and carboxylic acid groups such as but not limited to amino acids, these products may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases include aluminum hydroxide, calcium hydroxide, potassium hydroxide, sodium carbonate, sodium hydroxide, and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate and/or bicarbonate, ammonia, sodium hydroxide, and the like. The salt can be isolated as is from the system or converted to the free acid by reducing the pH to below the lowest pKa through addition of acid or treatment with an acidic ion exchange resin.

Nonnaturally occurring organism produced and used in accordance with the present invention are selected from a species of *Cupriavidus* or *Ralstonia* with diminished polyhydroxybutyrate synthesis or an organism with properties similar thereto.

For purposes of the present invention, by "diminishing" or "diminished" polyhydroxybutyrate synthesis, it is meant that the organism is altered to synthesize less polyhydroxybutyrate as compared to an unaltered wild-type organism of the same species. Organisms used in this disclosure can exhibit at least 20%, 25%, 30%, 40%, 50% or even greater decreased polyhydroxybutyrate synthesis as compared to an unperturbed wild-type organism of the same species.

Nonlimiting examples of species of *Cupriavidus* or *Ralstonia* useful in accordance with this disclosure include *Cupriavidus necator*, *Cupriavidus metallidurans*, *Cupriavidus taiwanensis*, *Cupriavidus pinatubonensis*, *Cupriavidus basilensis* and *Ralstonia pickettii*.

*C. necator* (also referred to as *Hydrogenomonas eutrophus*, *Alcaligenes eutropha*, *Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar, N. S. & Casida, L. E. Int. J. of Systematic Bacteriology 1987 37(4): 323-326), bacterial predation (Byrd et al. Can J Microbiol 1985 31:1157-1163; Sillman, C. E. & Casida, L. E. Can J Microbial 1986 32:760-762; Zeph, L. E. & Casida, L. E. Applied and Environmental Microbiology 1986 52(4):819-823) and polyhydroxybutyrate (PHB) synthesis. In addition, the cells have been reported to be capable of either aerobic or nitrate dependent anaerobic growth. A nonlimiting example of a *C. necator* organism useful in the present invention is a *C. necator* of the H16 strain. In one nonlimiting embodiment, a *C. necator* host of the H16 strain with at least a portion of the phaC1AB1 gene locus knocked out (AphaCAB) is used. In one nonlimiting embodiment, the organism is further modified to eliminate phaCAB, involved in PHBs production and/or H16-A0006-9 encoding endonucleases thereby improving transformation efficiency as described in U.S. patent application Ser. No. 15/717,216, teachings of which are incorporated herein by reference. However, other means of eliminating PHB synthesis are included within the scope of the invention.

By "an organism with properties similar thereto" it is meant an organism having one or more of the above-mentioned properties of *C. necator*.

In the process described herein, a fermentation strategy can be used that entails anaerobic, micro-aerobic or aerobic cultivation coupled with nutrient limitation such as iron, sulphate, nitrogen, potassium, oxygen, phosphorus, carbon and/or or NADP limitations, gradients thereof and any combinations thereof.

A cell retention strategy using a ceramic hollow fiber membrane can also be employed to achieve and maintain a high cell density during fermentation.

The principal carbon source fed to the fermentation can derive from a biological or non-biological feedstock. In one nonlimiting embodiment, the feedstock is fed to the fermentation as a gaseous or liquid stream.

Accordingly, feedstocks for fermentation may be gases such as carbon dioxide or hydrogen; sugars such as glucose, xylose or fructose; sugar acids such as gluconate; fatty acids or fats/oils, carboxylic acids such as propionic acid, lactic acid, and formic acid; amino acids, aromatics such as phenol and benzoic acid and/or alcohols such as glycerol.

The feedstocks may be carbon sources derived from by-product or waste streams such as brewing, dairy, plant oil, ethanol, corn, soy, fish, or sugar industries or any other food or agricultural waste such as used cooking oil.

The biological feedstock can be, or can derive from, monosaccharides, disaccharides, lignocellulose, hemicellulose, cellulose, paper-pulp waste, black liquor, lignin, levulinic acid and formic acid, triglycerides, glycerol, fatty acids, agricultural waste, thin stillage, condensed distillers' solubles or waste streams from the food processing or dairy industries municipal waste such as fruit peel/pulp or whey. The non-biological feedstock can be, or can derive from, natural gas, syngas, $CO_2/H_2$, CO, $H_2$, $O_2$, methanol, ethanol, waste streams from processes to produce monomers for the Nylon-66 and Nylon-6 industries such as but not limited to non-volatile residues (NVRs) and caustic wash waste streams from the cyclohexane oxidation process used to manufacture adipic acid or caprolactam or waste stream from other chemical industry processes such as, but not limited to a carbon black industry or a hydrogen-refining industry, or petrochemical industry, a nonlimiting example being a PTA-waste stream.

In one nonlimiting embodiment, at least one of the enzymatic conversions of the production method comprises gas fermentation within the modulated *Ralstonia* or *Cupriavidus* organism or other organism with properties similar thereto. In this embodiment, the gas fermentation may comprise at least one of natural gas, syngas, CO, $H_2$, $O_2$, $CO_2/H_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas fermentation comprises $CO_2/H_2$.

The methods of the present invention may further comprise recovering produced product from the organism. Once produced, any method can be used to isolate these products or derivatives or compounds related thereto. The isolation of at least one product can involve any one or more downstream processes generally known to be suitable for the at least partial separation and/or isolation of material from a reaction or bioprocess. The collection can, for example, involve centrifugations, cell disruptions, concentrations, precipitations, extractions, filtrations, crystallizations, distillations, chemical conversions, or combinations thereof. One or more biosynthetic products can be collected from the liquid or solid phase of the culture, or from the gas phase present in the headspace of a bioreactor or the off-gas.

The present invention also provides nonnaturally occurring organisms and methods for producing the nonnaturally occurring organisms modified to increase carbon-based product yield via modification to one or more genes involved in a stringent response or in regulatory networks. These nonnaturally occurring organisms exhibit increased product yield as compared to product yield in the same organism without modification to one or more genes involved in a stringent response or in regulatory networks. The nonnaturally occurring organisms are selected from a species of *Cupriavidus* or *Ralstonia* with diminished polyhydroxybutyrate synthesis or an organism with properties similar thereto.

Nonlimiting examples of species of *Cupriavidus* or *Ralstonia* useful in accordance with this disclosure include *Cupriavidus* necator, *Cupriavidus metallidurans, Cupriavi-* dus taiwanensis, Cupriavidus pinatubonensis, Cupriavidus basilensis and Ralstonia pickettii.

In one nonlimiting embodiment, the present invention relates to a substantially pure culture of the nonnaturally occurring organism modified to comprise one or more promoters which are inducible under one or more specific limitation conditions.

As used herein, a "substantially pure culture" of an altered organism is a culture of that microorganism in which less than about 40% (i.e., less than about 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the altered microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of nonnaturally occurring microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In addition, the present invention provides bio-derived, bio-based, or fermentation-derived products produced using the methods and/or nonnaturally occurring organisms disclosed herein. Examples of such products include, but are not limited to, compositions comprising at least one bio-derived, bio-based, or fermentation-derived compound or any combination thereof, as well as molded substances, formulations and semi-solid or non-semi-solid streams comprising one or more of the bio-derived, bio-based, or fermentation-derived compounds or compositions, combinations or products thereof.

While the invention has been described in detail, in some instances making reference to a specific aspect thereof, it is apparent to one of skill in the art that various changes and modifications can be made thereto without departing from its spirit and scope. The following section provides further illustration of the methods and materials of the present invention. These Examples are illustrative only and are not intended to limit the scope of the invention in any way.

EXAMPLE

Deletion of FadP Gene Increases Biomass and Isopropanol Production Under Nitrogen Limitation in Modified C. necator H16

C. necator H16 was genetically modified by deleting the polyhydroxybutyrate (PHB) pathway and the fatty acid degradation regulator, FadP (a transcriptional regulator belonging to the TetR family and is a potential repressor of fatty acid degradation pathways such as the β-oxidation), and by introducing the isopropanol (IPA) pathway. The strain was grown on a fructose-based media with ammonium sulphate as a source of nitrogen. A fed batch culture was used to compare the accumulation of biomass and the production of IPA under nitrogen limiting conditions. During batch phase growth was established at 30° C. and pH 6.6 in a fixed volume of 8 mL for 43 hours. During fed batch phase 5 mL of the same media lacking ammonium sulphate was fed into the cultures at a rate of 1.736 µL/min. The system was sampled just before the feeding started and 48 hours later.

Figure 1B:
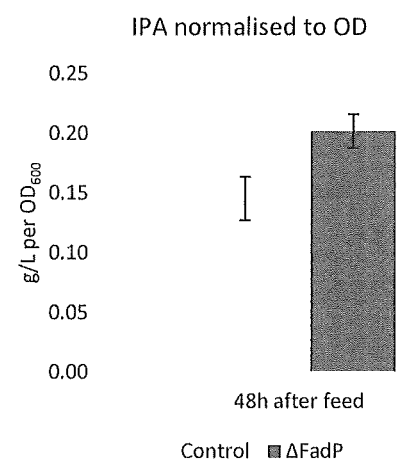
Figure 1C:
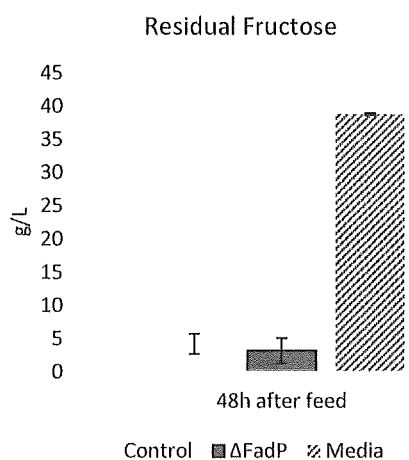
Figure 1D:
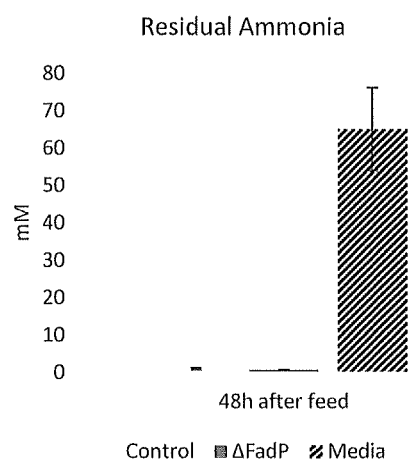

For each sample event, biomass ($OD_{600}$) (FIG. 1A), isopropanol (FIG. 1B), residual nitrogen (FIG. 1D) and carbon FIG. 1C) were determined.

These data show that at the end of the feeding regime there is more biomass present in the ΔFadP strain when compared with a similar strain where the FadP gene is still present. Moreover, ΔFadP strain produces higher levels of isopropanol. Both strains have consumed almost all fructose introduced in the system and have exhausted all the nitrogen available. When taken together these results are indicative of the modified strain funneling at least a portion of the potential additional carbon available towards cell growth and production of isopropanol.

TABLE 1

C. necator sequences

| Sequence Name | Nucleic acid SEQ ID NO: | Amino Acid SEQ ID NO: |
|---|---|---|
| H16_A0320, glnB-1, nitrogen regulatory protein P-II 1 | 3 | 4 |
| H16_A0324, ptsM, PTS fructose transporter subunit IIA | 5 | 6 |
| H16_A0325, ptsH, phosphocarrier protein HPr | 7 | 8 |
| H16_A0326, ptsI, ptsI - phosphoenolpyruvate-protein phosphotransferase | 9 | 10 |
| H16_A0383, Hpr kinase/phosphorylase | 11 | 12 |
| H16_A0384, ptsN, ptsIIA - Ntr - PTS IIA-like nitrogen-regulatory protein PtsN | 13 | 14 |
| H16_A0386, sigma 54 modulation protein S30EA, ribosome hibernation promoting factor | 15 | 16 |
| H16_A0387, rpoN, sigma 54 | 17 | 18 |
| H16_A0459, FadP, TetR - TetR/AcrR family transcriptional regulator | 19 | 20 |
| H16_A0471, gdhA1, Glu/Leu/Phe/Val dehydrogenase | 21 | 22 |
| H16_A0750, glnB-2, P-II family nitrogen regulator | 23 | 24 |
| H16_A0955, SpoT1, bifunctional (p)ppGpp synthetase/guanosine-3',5'-bis(diphosphate) 3'-pyrophosphohydrolase | 25 | 26 |
| H16_A1177, HexR-1, MurR/RpiR family transcriptional regulator | 27 | 28 |
| H16_A1337, SpoT2, bifunctional (p)ppGpp synthetase/guanosine-3',5'-bis(diphosphate) 3'-pyrophosphohydrolase | 29 | 30 |
| H16_A1356, gudB, NAD-glutamate dehydrogenase | 31 | 32 |
| H16_A1372, AccR, DNA-binding response regulator | 33 | 34 |
| H16_A1373, PAS domain-containing sensor histidine kinase | 35 | 36 |
| H16_A2057, glnD, [protein-PII] uridylyltransferase | 37 | 38 |
| H16_A2332, ntrC, Fis - nitrogen regulation protein NR(I) | 39 | 40 |
| H16_A2333, ntrB, PAS domain-containing protein | 41 | 42 |
| H16_A2335, glnA, type I glutamate-ammonia ligase | 43 | 44 |
| H16_A2504, GlpR, DeoR/GlpR transcriptional regulator | 45 | 46 |
| H16_A3430, gltD, glutamate synthase subunit beta | 47 | 48 |
| H16_A3431, gltB1, glutamate synthase subunit alpha | 49 | 50 |
| H16_A3736, PsrA, TetR/AcrR family transcriptional regulator | 51 | 52 |

TABLE 1-continued

C. necator sequences

| Sequence Name | Nucleic acid SEQ ID NO: | Amino Acid SEQ ID NO: |
|---|---|---|
| H16_B0094, LldR, FCD domain-containing protein | 53 | 54 |
| H16_B0618, glnA2, type I glutamate-ammonia ligase | 55 | 56 |
| H16_B1210, hexR-2, MurR/RpiR family transcriptional regulator | 57 | 58 |
| H16_B1945, gdhA2, NADP-specific glutamate dehydrogenase | 59 | 60 |
| H16_B2191, glnA3, type III glutamate-ammonia ligase | 61 | 62 |
| sucA, riboswitch linked to H16_A2325 | 2 | |

What is claimed is:

1. A method for increasing carbon-based chemical product yield in an organism, said method comprising modulating activity of one or more polypeptides or functional fragments thereof involved in a stringent response and/or in a regulatory network of an organism selected from a species of *Cupriavidus* or *Ralstonia* with diminished polyhydroxybutyrate synthesis, thereby increasing carbon-based chemical product yield in the organism as compared to an organism without said modulated polypeptide activity, wherein the one or more polypeptides or functional fragments thereof is encoded by a gene having at least 90% sequence identity to a gene selected from the FadP gene of SEQ ID NO:19 encoding FadP polypeptide having fatty acid synthesis activity, the PsrA gene of SEQ ID NO:51 encoding PsrA polypeptide having fatty acid degradation activity or the LldR gene of SEQ ID NO:53 encoding LldR polypeptide having lactate dehydrogenase activity.

2. The method of claim 1, wherein modulating the activity of one or more polypeptides or functional fragments thereof comprises overexpressing or mutating an endogenous or exogenous nucleic acid sequence in the organism.

* * * * *

SEQUENCE LISTING

<160> NUMBER OF SEQ ID NOS: 62

<210> SEQ ID NO 1
<211> LENGTH: 20
<212> TYPE: DNA
<213> ORGANISM: C. necator
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 1
aatngwacga ycgtkcknwt                                       20

<210> SEQ ID NO 2
<211> LENGTH: 97
<212> TYPE: DNA
<213> ORGANISM: C. necator

<400> SEQUENCE: 2
ttgtttgcga tccgctaacc ggtcaagccg tgtcgcggaa ggttgaataa cccgctgaac    60
tccggcattc ccggagaata gtgagcgtcc catgatg                             97

<210> SEQ ID NO 3
<211> LENGTH: 339
<212> TYPE: DNA
<213> ORGANISM: C. necator

<400> SEQUENCE: 3
atgaaactca tcatcgcagt catcaagccg ttcaagctcg acgaagtgcg cgaagcgctg    60
tcggacgtgg gcgtgtccgg cattaccgtg accgaagtga aaggcttcgg ccgccagaag   120
ggccacaccg agctgtaccg cggcgccgaa tacatcgtcg acttcctgcc caaggtgaag   180
atcgaggtgg cggtgcccga cgacgtggtc gagcgcgcca tcgaggcggt cgagaaatcg   240
gcccgcaccg gcaagatcgg cgacggcaag atcttcgtgg caccgatcga gcaggtcatc   300
cgcatccgca ccggcgagac cggcggcgat gccctgtga                          339

<210> SEQ ID NO 4
<211> LENGTH: 112
<212> TYPE: PRT
<213> ORGANISM: C. necator

<400> SEQUENCE: 4

Met Lys Leu Ile Ile Ala Val Ile Lys Pro Phe Lys Leu Asp Glu Val
1               5                   10                  15

Arg Glu Ala Leu Ser Asp Val Gly Val Ser Gly Ile Thr Val Thr Glu
            20                  25                  30

Val Lys Gly Phe Gly Arg Gln Lys Gly His Thr Glu Leu Tyr Arg Gly
        35                  40                  45

Ala Glu Tyr Ile Val Asp Phe Leu Pro Lys Val Lys Ile Glu Val Ala
    50                  55                  60

Val Pro Asp Asp Val Val Glu Arg Ala Ile Glu Ala Val Glu Lys Ser
65                  70                  75                  80

Ala Arg Thr Gly Lys Ile Gly Asp Gly Lys Ile Phe Val Ala Pro Ile
                85                  90                  95

Glu Gln Val Ile Arg Ile Arg Thr Gly Glu Thr Gly Gly Asp Ala Leu
            100                 105                 110

<210> SEQ ID NO 5
<211> LENGTH: 456
<212> TYPE: DNA
<213> ORGANISM: C. necator

<400> SEQUENCE: 5
atggcaggca ttctgatcat cgcgcacacc ccgctggctt cggcgctgcg cgattgcgcc      60
gcccacgtct actgcggcca gccgcagcgg ctggaatcca tcgacgtcct tcccgatgcc     120
gaccccgccg tcgtgctggc cgaggccagg cgccggctgg cggccatctg cgaggacaac     180
ggcgcgctgg tcctcaccga tatcttcggc gccaccccg ccaatattgc cgcacgcctg      240
gccgagccgg gccgcgtgcg ggtgctggcc ggcgtcaacc ttcccatgct cgtgcgcgcg     300
atctgctacc gcggcgaaaa gctcgaccag cttgccacca aggccctggc cggcggctcg     360
cagggtgtgc tgcaggtcgg caccacgact gtccagaacc aaaccgcaaa ccatcccgac     420
aaatatgctg cagagggaca ccaccatcat caataa                               456

<210> SEQ ID NO 6
<211> LENGTH: 151
<212> TYPE: PRT
<213> ORGANISM: C. necator

<400> SEQUENCE: 6

Met Ala Gly Ile Leu Ile Ile Ala His Thr Pro Leu Ala Ser Ala Leu
1               5                   10                  15

Arg Asp Cys Ala Ala His Val Tyr Cys Gly Gln Pro Gln Arg Leu Glu
            20                  25                  30

Ser Ile Asp Val Leu Pro Asp Ala Asp Pro Ala Val Val Leu Ala Glu
        35                  40                  45

Ala Arg Arg Arg Leu Ala Ala Ile Cys Glu Asp Asn Gly Ala Leu Val
    50                  55                  60

Leu Thr Asp Ile Phe Gly Ala Thr Pro Ala Asn Ile Ala Ala Arg Leu
65                  70                  75                  80

Ala Glu Pro Gly Arg Val Arg Val Leu Ala Gly Val Asn Leu Pro Met
                85                  90                  95

Leu Val Arg Ala Ile Cys Tyr Arg Gly Glu Lys Leu Asp Gln Leu Ala
            100                 105                 110

Thr Lys Ala Leu Ala Gly Gly Ser Gln Gly Val Leu Gln Val Gly Thr
        115                 120                 125

Thr Thr Val Gln Asn Gln Thr Ala Asn His Pro Asp Lys Tyr Ala Ala
    130                 135                 140

Glu Gly His His His His Gln
145                 150

<210> SEQ ID NO 7
<211> LENGTH: 270
<212> TYPE: DNA
<213> ORGANISM: C. necator

<400> SEQUENCE: 7

```
atgctgcaga gggacaccac catcatcaat aaactcggcc tgcatgcgcg cgcgtccgcc      60
aagctgaccc agctcgccgg caactttgtc agccaggtca agatgtcccg caatggtcgc     120
caggtcgacg ccaagagcat catgggcgtc atgatgctgg ccgccgggat cggctcgacg     180
gtgaccctcg agaccgacgg ccccgacgag caggaggcga tggacgcgct gctggcgctg     240
atcgccaacc gctttggtga gggagagtga                                      270
```

<210> SEQ ID NO 8
<211> LENGTH: 89
<212> TYPE: PRT
<213> ORGANISM: C. necator

<400> SEQUENCE: 8

```
Met Leu Gln Arg Asp Thr Thr Ile Ile Asn Lys Leu Gly Leu His Ala
1               5                  10                  15

Arg Ala Ser Ala Lys Leu Thr Gln Leu Ala Gly Asn Phe Val Ser Gln
            20                  25                  30

Val Lys Met Ser Arg Asn Gly Arg Gln Val Asp Ala Lys Ser Ile Met
        35                  40                  45

Gly Val Met Met Leu Ala Ala Gly Ile Gly Ser Thr Val Thr Leu Glu
    50                  55                  60

Thr Asp Gly Pro Asp Glu Gln Glu Ala Met Asp Ala Leu Leu Ala Leu
65                  70                  75                  80

Ile Ala Asn Arg Phe Gly Glu Gly Glu
                85
```

<210> SEQ ID NO 9
<211> LENGTH: 1761
<212> TYPE: DNA
<213> ORGANISM: C. necator

<400> SEQUENCE: 9

```
atgcctttcg ccctgcacgg catcccggtc tcgcgcggcg tcgccatcgg gcgcgcgcac      60
ctgcttgcgc ccgcggcgct ggacgtgtcg cactacctgg tcgatgaaga ccagctcgac     120
gccgaggtcg aacggctgcg cgcagcgcgc gccgcggtgc gggcggagct ggccgcgctc     180
aagcgcgacc tgccgcgcga tgcgcccgag agctgggcg cattcctgga cgtgcacgcg     240
atgatcctcg acgacgaggc gctggcgcgc gagcccgagg ccctgatccg ggccgccgc      300
tacaacgcag agtgggcact taccacgcgc ctcgaagagc tgatgcgcca gttcgacgag     360
atcgaggatg aatacctgcg cgagcgcaag accgatatcc ggcaggtggt cgagcgcatc     420
ctgaaggcgc tcgccggggc tccggtgctg gtgcccgcgc cggtgccggc ctggccgcc      480
gacggcgagg ccgcgaccgg ggtgatcgtg gtggcccacg atatcgcccc ggccgacatg     540
ctgcagttcc gccataccgt cttccacggc ttcgtcaccg acatgggcgg acgcacctcg     600
cataccgcca tgtcgcgcg cagcctggac atcccggccg cggtcggcgt gcagagcgcg     660
agcgagctga tccgccagga cgactggatc atcatcgacg cgatgccgg gctggtgatc     720
gtcgacccga ccgccatcat cctggaagag taccgccacc ggcagagcga gcgcgcgctg     780
```

-continued

```
gaaaagaagc gcctgcagcg gctgcggcat accccggcgg tgacgctgga cgggctggaa    840
atcgacctgc tggccaatat cgagatggcc gaggacgccg gcgcggcgct ggcggccggc    900
gcggtcggcg tgggcctgtt ccgttccgaa ttcctgttca tgaaccggcg cgacgagttg    960
ccgggcgagg acgagcagtt ccaggcctac cgcggcgcgg tcgatgccat gcacgggctg   1020
ccggtgacta tccgcaccat cgacatcggc gccgacaagc cgctcgatgc cgcggcgat    1080
gaattcgaga ccgcgctgaa cccggcgctg ggcctgcgcg cgatccgctg gtcgctgtcc   1140
gagccgggca tgttcctgac ccagctgcgc gcgctgctgc gggcttcggc cttcggcccg   1200
gtgcggctgc tggtgccgat gctggcgcat gccagcgaga tcgaccagac cctggcgctg   1260
atcgccaagg ccaagcgcca gctcgacgag cgcggcgagg cctatgaccc gggcatgaag   1320
gtcggcgcca tgatcgagat cccggcggcg gtgctgctgc tgccgctgtt cctgcgcaag   1380
atggacttcc tgtccatcgg caccaacgac ctgatccagt acacgctggc catcgatcgc   1440
gccgacaacg cggtggcgca cctgttcgac ccgctgcacc cggcggtgct gcagctggtg   1500
gcgcgcacca tccgcgaggc caaccgcgcc ggcgtgccgg tggccgtgtg cggcgaaatg   1560
gcgggcgacc cgtccatgac ccggctgctg ctgggcatgg ggctgcgcga gttctcgatg   1620
cacccggcgc agctgctgcg ggtcaagcag gagatcctgc atgccactg cgaacggctc   1680
gagccgctgg tcgaccaggt cctgcaggcc ttcgatcccg aggagcaggc ggccgccctg   1740
cggcagctgg cacgaccctg a                                              1761
```

<210> SEQ ID NO 10
<211> LENGTH: 586
<212> TYPE: PRT
<213> ORGANISM: C. necator

<400> SEQUENCE: 10

```
Met Pro Phe Ala Leu His Gly Ile Pro Val Ser Arg Gly Val Ala Ile
1               5                   10                  15

Gly Arg Ala His Leu Leu Ala Pro Ala Ala Leu Asp Val Ser His Tyr
            20                  25                  30

Leu Val Asp Glu Asp Gln Leu Asp Ala Glu Val Glu Arg Leu Arg Ala
        35                  40                  45

Ala Arg Ala Ala Val Arg Ala Glu Leu Ala Ala Leu Lys Arg Asp Leu
    50                  55                  60

Pro Arg Asp Ala Pro Glu Glu Leu Gly Ala Phe Leu Asp Val His Ala
65                  70                  75                  80

Met Ile Leu Asp Asp Glu Ala Leu Ala Arg Glu Pro Glu Ala Leu Ile
                85                  90                  95

Arg Gly Arg Arg Tyr Asn Ala Glu Trp Ala Leu Thr Thr Arg Leu Glu
            100                 105                 110

Glu Leu Met Arg Gln Phe Asp Glu Ile Glu Asp Glu Tyr Leu Arg Glu
        115                 120                 125

Arg Lys Thr Asp Ile Arg Gln Val Val Glu Arg Ile Leu Lys Ala Leu
    130                 135                 140

Ala Gly Ala Pro Val Leu Val Pro Ala Pro Val Pro Ala Leu Ala Ala
145                 150                 155                 160

Asp Gly Glu Ala Ala Thr Gly Val Ile Val Ala His Asp Ile Ala
                165                 170                 175

Pro Ala Asp Met Leu Gln Phe Arg His Thr Val Phe His Gly Phe Val
            180                 185                 190

Thr Asp Met Gly Gly Arg Thr Ser His Thr Ala Ile Val Ala Arg Ser
```

```
            195                 200                 205
Leu Asp Ile Pro Ala Ala Val Gly Val Gln Ser Ala Ser Glu Leu Ile
    210                 215                 220

Arg Gln Asp Asp Trp Ile Ile Ile Asp Gly Asp Ala Gly Leu Val Ile
225                 230                 235                 240

Val Asp Pro Thr Ala Ile Ile Leu Glu Glu Tyr Arg His Arg Gln Ser
                245                 250                 255

Glu Arg Ala Leu Glu Lys Lys Arg Leu Gln Arg Leu Arg His Thr Pro
            260                 265                 270

Ala Val Thr Leu Asp Gly Leu Glu Ile Asp Leu Leu Ala Asn Ile Glu
        275                 280                 285

Met Ala Glu Asp Ala Gly Ala Ala Leu Ala Ala Gly Ala Val Gly Val
    290                 295                 300

Gly Leu Phe Arg Ser Glu Phe Leu Phe Met Asn Arg Arg Asp Glu Leu
305                 310                 315                 320

Pro Gly Glu Asp Glu Gln Phe Gln Ala Tyr Arg Gly Ala Val Asp Ala
                325                 330                 335

Met His Gly Leu Pro Val Thr Ile Arg Thr Ile Asp Ile Gly Ala Asp
            340                 345                 350

Lys Pro Leu Asp Ala Arg Gly Asp Glu Phe Glu Thr Ala Leu Asn Pro
        355                 360                 365

Ala Leu Gly Leu Arg Ala Ile Arg Trp Ser Leu Ser Glu Pro Gly Met
370                 375                 380

Phe Leu Thr Gln Leu Arg Ala Leu Leu Arg Ala Ser Ala Phe Gly Pro
385                 390                 395                 400

Val Arg Leu Leu Val Pro Met Leu Ala His Ala Ser Glu Ile Asp Gln
                405                 410                 415

Thr Leu Ala Leu Ile Ala Lys Ala Lys Arg Gln Leu Asp Glu Arg Gly
            420                 425                 430

Glu Ala Tyr Asp Pro Gly Met Lys Val Gly Ala Met Ile Glu Ile Pro
        435                 440                 445

Ala Ala Val Leu Leu Leu Pro Leu Phe Leu Arg Lys Met Asp Phe Leu
    450                 455                 460

Ser Ile Gly Thr Asn Asp Leu Ile Gln Tyr Thr Leu Ala Ile Asp Arg
465                 470                 475                 480

Ala Asp Asn Ala Val Ala His Leu Phe Asp Pro Leu His Pro Ala Val
                485                 490                 495

Leu Gln Leu Val Ala Arg Thr Ile Arg Glu Ala Asn Arg Ala Gly Val
            500                 505                 510

Pro Val Ala Val Cys Gly Glu Met Ala Gly Asp Pro Ser Met Thr Arg
        515                 520                 525

Leu Leu Leu Gly Met Gly Leu Arg Glu Phe Ser Met His Pro Ala Gln
    530                 535                 540

Leu Leu Arg Val Lys Gln Glu Ile Leu His Ala His Cys Glu Arg Leu
545                 550                 555                 560

Glu Pro Leu Val Asp Gln Val Leu Gln Ala Phe Asp Pro Glu Glu Gln
                565                 570                 575

Ala Ala Ala Leu Arg Gln Leu Ala Arg Pro
            580                 585

<210> SEQ ID NO 11
<211> LENGTH: 972
<212> TYPE: DNA
<213> ORGANISM: C. necator
```

<400> SEQUENCE: 11

```
atggaactca ccggcgtcac ctcccagtcc atcttcgacg acaacgcagc cgacatcaaa      60
ctctcgtggg tggccggcct ggaaggtgcg gatcgcgcct tcgatgtgga gttcgcccgc     120
gaagccacct ccgccgccga cctggtgggc cacctgaacc tgatccaccc caaccgcatc     180
caggtgctcg gcaagcccga gatcacttat taccagcgac tggacgacga gacccgcaag     240
cgccagatgg gcgagctgat cctgctggag ccgcccttcc tggtgatcgc cgacggcatg     300
gagccgccgc ccgacctgga actgcgctgc acgcgctcgt ccacgccgct gttcaccacg     360
ccggtgtcgt cggccgcggt gatcgaccac ctgcgcctgt acctgtcgcg tatctccgcg     420
ccgcgcgtga ccatgcacgg ggtattcctc gacatcctgg gcatgggcgt gctgatcatg     480
ggcgaatcgg gcctgggcaa gagcgaactg ggcctggaac tgatctcgcg cggccacggg     540
ctggtggccg atgatgccgt ggacttcgtg cgcctggggc cggatttcat tgaaggccgc     600
tgcccgccgc tgctgcagaa cctgcttgaa gtacgcggtc tgggcctgct cgacatcaag     660
accatcttcg gtgagaccgc ggtgcgccgg aagatgaaga tcaagctggt ggtgcagttg     720
gtgcgtcgca atgacggcga gttcgagcgg ctgccgctcg attcgcaata cctcgacgtg     780
ctgggcctgc cgatccacat ggtcaagatc caggtggcgg ccgggcgcaa cctggccgtg     840
ctggtcgagg ccgcggtgcg caacaccatc ctgcgcctgc gcggcatcga tacgctgcgc     900
gacttcatgg accggcagcg cgccgcgatg caggccgatg cagtatcgcg cggccagggc     960
cgcttgctct ga                                                          972
```

<210> SEQ ID NO 12
<211> LENGTH: 323
<212> TYPE: PRT
<213> ORGANISM: C. necator

<400> SEQUENCE: 12

```
Met Glu Leu Thr Gly Val Thr Ser Gln Ser Ile Phe Asp Asp Asn Ala
1               5                   10                  15

Ala Asp Ile Lys Leu Ser Trp Val Ala Gly Leu Glu Gly Ala Asp Arg
            20                  25                  30

Ala Phe Asp Val Glu Phe Ala Arg Glu Ala Thr Ser Ala Ala Asp Leu
        35                  40                  45

Val Gly His Leu Asn Leu Ile His Pro Asn Arg Ile Gln Val Leu Gly
    50                  55                  60

Lys Pro Glu Ile Thr Tyr Tyr Gln Arg Leu Asp Asp Glu Thr Arg Lys
65                  70                  75                  80

Arg Gln Met Gly Glu Leu Ile Leu Leu Glu Pro Pro Phe Leu Val Ile
                85                  90                  95

Ala Asp Gly Met Glu Pro Pro Asp Leu Glu Leu Arg Cys Thr Arg
            100                 105                 110

Ser Ser Thr Pro Leu Phe Thr Thr Pro Val Ser Ala Ala Val Ile
        115                 120                 125

Asp His Leu Arg Leu Tyr Leu Ser Arg Ile Ser Ala Pro Arg Val Thr
    130                 135                 140

Met His Gly Val Phe Leu Asp Ile Leu Gly Met Gly Val Leu Ile Met
145                 150                 155                 160

Gly Glu Ser Gly Leu Gly Lys Ser Glu Leu Gly Leu Glu Leu Ile Ser
                165                 170                 175

Arg Gly His Gly Leu Val Ala Asp Asp Ala Val Asp Phe Val Arg Leu
```

```
                    180                 185                 190
Gly Pro Asp Phe Ile Glu Gly Arg Cys Pro Leu Leu Gln Asn Leu
            195                 200                 205

Leu Glu Val Arg Gly Leu Gly Leu Leu Asp Ile Lys Thr Ile Phe Gly
        210                 215                 220

Glu Thr Ala Val Arg Arg Lys Met Lys Ile Lys Leu Val Val Gln Leu
225                 230                 235                 240

Val Arg Arg Asn Asp Gly Glu Phe Glu Arg Leu Pro Leu Asp Ser Gln
                245                 250                 255

Tyr Leu Asp Val Leu Gly Leu Pro Ile His Met Val Lys Ile Gln Val
            260                 265                 270

Ala Ala Gly Arg Asn Leu Ala Val Leu Val Glu Ala Ala Val Arg Asn
        275                 280                 285

Thr Ile Leu Arg Leu Arg Gly Ile Asp Thr Leu Arg Asp Phe Met Asp
        290                 295                 300

Arg Gln Arg Ala Ala Met Gln Ala Asp Ala Val Ser Arg Gly Gln Gly
305                 310                 315                 320

Arg Leu Leu
```

<210> SEQ ID NO 13
<211> LENGTH: 456
<212> TYPE: DNA
<213> ORGANISM: C. necator

<400> SEQUENCE: 13

```
atgaatcgtt tggccaaatt gctgccaccc ggcaacatca ccctcgacgt cagcgtcacc      60
agcaagaagc gtgtgttcga gcaggccggg ctcctcttcg agaacaacca tggtgtggcg     120
cgcgccatcg tgacggacaa cctgttcgcg cgcgagtcgc ttggatccac cggcctgggc     180
gccggcgtgg caatcccgca cggccgcatc aagggcctga agcagccgct ggccgcgttc     240
atgcgcctgg ccgaaccaat tccgttcgaa tcgcccgatg gcaagccggt atcgctgctg     300
atcttcctgc tggtgcccga acaggctacg cagcagcacc tggaaatcct gtccgaaatc     360
gcgcaactgc tttccgaccg cgacatgcgt gaaggctgg ccacgctgcc cacgcccgat     420
gccgtccatc agttgctgat cgcatggcat ccctga                               456
```

<210> SEQ ID NO 14
<211> LENGTH: 151
<212> TYPE: PRT
<213> ORGANISM: C. necator

<400> SEQUENCE: 14

```
Met Asn Arg Leu Ala Lys Leu Leu Pro Pro Gly Asn Ile Thr Leu Asp
1               5                   10                  15

Val Ser Val Thr Ser Lys Lys Arg Val Phe Glu Gln Ala Gly Leu Leu
            20                  25                  30

Phe Glu Asn Asn His Gly Val Ala Arg Ala Ile Val Thr Asp Asn Leu
        35                  40                  45

Phe Ala Arg Glu Ser Leu Gly Ser Thr Gly Leu Gly Ala Gly Val Ala
    50                  55                  60

Ile Pro His Gly Arg Ile Lys Gly Leu Lys Gln Pro Leu Ala Ala Phe
65                  70                  75                  80

Met Arg Leu Ala Glu Pro Ile Pro Phe Glu Ser Pro Asp Gly Lys Pro
                85                  90                  95

Val Ser Leu Leu Ile Phe Leu Leu Val Pro Glu Gln Ala Thr Gln Gln
```

```
              100                 105                 110
His Leu Glu Ile Leu Ser Glu Ile Ala Gln Leu Leu Ser Asp Arg Asp
        115                 120                 125

Met Arg Glu Gly Leu Ala Thr Leu Pro Thr Pro Asp Ala Val His Gln
        130                 135                 140

Leu Leu Ile Ala Trp His Pro
145                 150

<210> SEQ ID NO 15
<211> LENGTH: 351
<212> TYPE: DNA
<213> ORGANISM: C. necator

<400> SEQUENCE: 15
atgaacttca agatcagtgg acaccacctg gacatcacgc cccctctgcg tgagtacgtg      60
gaaacgaagc tggagcgaat cgtcaggcat ttcgatcaag tcattggcgt tagtgtgctg     120
ctctctgtcg acaaccacaa ggaaaaggac cggcgtcagt acgcggaaat caatctacat     180
ctcaagggca aggacatctt tgtcgaagcg catcacgaag acctgtatgc agcgatcgac     240
gcactcgtcg acaagctgga ccgtcaggtg atccgctaca aggatcgcgt gcaaggccac     300
gaccgcgaag cggtcaagta ccagatggcc gcagcgcaaa tgcagcaatg a              351

<210> SEQ ID NO 16
<211> LENGTH: 116
<212> TYPE: PRT
<213> ORGANISM: C. necator

<400> SEQUENCE: 16

Met Asn Phe Lys Ile Ser Gly His His Leu Asp Ile Thr Pro Pro Leu
1               5                   10                  15

Arg Glu Tyr Val Glu Thr Lys Leu Glu Arg Ile Val Arg His Phe Asp
            20                  25                  30

Gln Val Ile Gly Val Ser Val Leu Leu Ser Val Asp Asn His Lys Glu
        35                  40                  45

Lys Asp Arg Arg Gln Tyr Ala Glu Ile Asn Leu His Leu Lys Gly Lys
    50                  55                  60

Asp Ile Phe Val Glu Ala His His Glu Asp Leu Tyr Ala Ala Ile Asp
65                  70                  75                  80

Ala Leu Val Asp Lys Leu Asp Arg Gln Val Ile Arg Tyr Lys Asp Arg
                85                  90                  95

Val Gln Gly His Asp Arg Glu Ala Val Lys Tyr Gln Met Ala Ala Ala
            100                 105                 110

Gln Met Gln Gln
        115

<210> SEQ ID NO 17
<211> LENGTH: 1482
<212> TYPE: DNA
<213> ORGANISM: C. necator

<400> SEQUENCE: 17
atgaaaccgt cgctacagct ccgcctttcc cagcatctgg ccctgacccc gcaactgcag      60
cagtcgatcc ggctgctgca gctttccacg ctggaactgc agcaagaggt cgaacaggca     120
ctgacggaaa accctctgct cgaacgcgag aacgactgga tcgaaagccc gctgcgcgtg     180
gcggccgacg gctcggtcaa cctgcagagc gcaccggcgc ccgcgccggc agagccgcag     240
```

```
ggcaatggcg aggcccgcgc cgacggcgcg gctgacgacg acagctatgg cgacagcggc    300
aacggcgacg actatggcag cagcgactgg agcctggacg actttgcccg ccgcccccag    360
ggcgacgagg acgaaaaaac gccgatgcag ctgcgcgaag ccgagcccac gctgcgcgag    420
tacctgatgg aacagctcac gccgctgaag atctcggcgc gcgacaaggg cctggccatc    480
ttcctgatcg aatcgctcga cgacgatggc tacctgagcg catcgcttga ggagatctgc    540
acggagttgc cggaagaact cgagttcgag atcgaggagg tccacgccat cctcacgctg    600
ctgcagagct tcgacccgcc cggcgtgggc gcgcgcaacg ccgccgagtg cctggccctg    660
cagttgcggc gcctgacgca cccgcagcgc gaactggccc tgaacatcgt gaccaaccac    720
ctggagttgc tcgcagtacg cgactacacg cggctgaaga aggcgctgca ggtggatgaa    780
gcggcgctga agtccgcaca cgaactgatc cgctcgctgg cgccctaccc cggccatgca    840
tacagccgcc cggaggcgga cttcgtggtg ccggacgtgt tcgtgcgcaa gggtggcggc    900
ggctggatcg cgcagctcaa tccggatgtg atgccgaggc tgcgcatcaa tgacatgtat    960
gcgcaaatcc tacgtggcgc aaagggtgag tccggcaccg ccgggctgca gcagaagctg    1020
caagaggcgc gctggctgat caagaacatc cagcagaggt tcgacaaaat cctgcgtgtc    1080
tcgcaggcca ttgtcgagcg tcaaaagaac ttttttcagcc acggcgaaat cgccatgcgc    1140
cccttggttt tgcgggagat tgccgataca ctgggtttac acgagtcaac catctcccgg    1200
gtgacgacca ataaatatat ggcaacgccg atgggtactt tcgaactgaa gtacttcttc    1260
ggcagccacg tgtccaccga accggtggc gcggcttcgt caacggccat ccgcgccttg    1320
atcaagcaac tgataggagc cgaagacccg aggaatcccc tttccgacag tcgcattgcc    1380
gaactgctgg gcgaacaagg cttcgttgtc gcacgccgca ccgttgccaa gtatcgcgaa    1440
gccctgaaga tccccgcagt caatctccgc aagtctttgt ag                       1482
```

<210> SEQ ID NO 18
<211> LENGTH: 493
<212> TYPE: PRT
<213> ORGANISM: C. necator

<400> SEQUENCE: 18

```
Met Lys Pro Ser Leu Gln Leu Arg Leu Ser Gln His Leu Ala Leu Thr
1               5                   10                  15

Pro Gln Leu Gln Gln Ser Ile Arg Leu Leu Gln Leu Ser Thr Leu Glu
            20                  25                  30

Leu Gln Gln Glu Val Glu Gln Ala Leu Thr Glu Asn Pro Leu Leu Glu
        35                  40                  45

Arg Glu Asn Asp Trp Ile Glu Ser Pro Leu Arg Val Ala Ala Asp Gly
    50                  55                  60

Ser Val Asn Leu Gln Ser Ala Pro Ala Pro Ala Glu Pro Gln
65                  70                  75                  80

Gly Asn Gly Glu Ala Arg Ala Asp Gly Ala Ala Asp Asp Ser Tyr
                85                  90                  95

Gly Asp Ser Gly Asn Gly Asp Asp Tyr Gly Ser Ser Asp Trp Ser Leu
            100                 105                 110

Asp Asp Phe Ala Arg Arg Pro Gln Gly Asp Glu Asp Lys Thr Pro
        115                 120                 125

Met Gln Leu Arg Glu Ala Glu Pro Thr Leu Arg Glu Tyr Leu Met Glu
    130                 135                 140

Gln Leu Thr Pro Leu Lys Ile Ser Ala Arg Asp Lys Gly Leu Ala Ile
145                 150                 155                 160
```

```
Phe Leu Ile Glu Ser Leu Asp Asp Gly Tyr Leu Ser Ala Ser Leu
            165                 170                 175
Glu Glu Ile Cys Thr Glu Leu Pro Glu Leu Glu Phe Glu Ile Glu
            180                 185                 190
Glu Val His Ala Ile Leu Thr Leu Leu Gln Ser Phe Asp Pro Gly
            195                 200                 205
Val Gly Ala Arg Asn Ala Ala Glu Cys Leu Ala Leu Gln Leu Arg Arg
210                 215                 220
Leu Thr His Pro Gln Arg Glu Leu Ala Leu Asn Ile Val Thr Asn His
225                 230                 235                 240
Leu Glu Leu Leu Ala Val Arg Asp Tyr Thr Arg Leu Lys Lys Ala Leu
            245                 250                 255
Gln Val Asp Glu Ala Ala Leu Lys Ser Ala His Glu Leu Ile Arg Ser
            260                 265                 270
Leu Ala Pro Tyr Pro Gly His Ala Tyr Ser Arg Pro Glu Ala Asp Phe
            275                 280                 285
Val Val Pro Asp Val Phe Val Arg Lys Gly Gly Gly Trp Ile Ala
            290                 295                 300
Gln Leu Asn Pro Asp Val Met Pro Arg Leu Arg Ile Asn Asp Met Tyr
305                 310                 315                 320
Ala Gln Ile Leu Arg Gly Ala Lys Gly Glu Ser Gly Thr Ala Gly Leu
            325                 330                 335
Gln Gln Lys Leu Gln Glu Ala Arg Trp Leu Ile Lys Asn Ile Gln Gln
            340                 345                 350
Arg Phe Asp Lys Ile Leu Arg Val Ser Gln Ala Ile Val Glu Arg Gln
            355                 360                 365
Lys Asn Phe Phe Ser His Gly Glu Ile Ala Met Arg Pro Leu Val Leu
            370                 375                 380
Arg Glu Ile Ala Asp Thr Leu Gly Leu His Glu Ser Thr Ile Ser Arg
385                 390                 395                 400
Val Thr Thr Asn Lys Tyr Met Ala Thr Pro Met Gly Thr Phe Glu Leu
            405                 410                 415
Lys Tyr Phe Phe Gly Ser His Val Ser Thr Glu Thr Gly Gly Ala Ala
            420                 425                 430
Ser Ser Thr Ala Ile Arg Ala Leu Ile Lys Gln Leu Ile Gly Ala Glu
            435                 440                 445
Asp Pro Arg Asn Pro Leu Ser Asp Ser Arg Ile Ala Glu Leu Leu Gly
            450                 455                 460
Glu Gln Gly Phe Val Val Ala Arg Arg Thr Val Ala Lys Tyr Arg Glu
465                 470                 475                 480
Ala Leu Lys Ile Pro Ala Val Asn Leu Arg Lys Ser Leu
            485                 490
```

<210> SEQ ID NO 19
<211> LENGTH: 591
<212> TYPE: DNA
<213> ORGANISM: C. necator

<400> SEQUENCE: 19

| | | | | | |
|---|---|---|---|---|---|
| atgcgcaagg | gtgaaatgac | gcgcgtggcg | attctggatg | ccgcactgga | attgtcgtcc | 60 |
| cgcgacgggc | tcgaaggtct | gaccatcggg | ctgctcgcgg | aacgcatgca | gatgagcaag | 120 |
| agcggtgtct | tcgcgcattt | cggttcgcgc | gaagacctgc | aggtggaggt | ggtgcgggag | 180 |
| tatcaccgcc | ggttcgagca | ggaggtgttc | tatccctcgc | tgcaggagcc | gcgcggcctg | 240 |

```
cccggctat ggtcgatggt gcggcgctgg atggagaagc gcatccagga agtgacgact      300
ggatgcatct acatcagcgg cgccgtggag tacgacgacc gtgccggcag cctggtgcgt      360
gacgagctgg tcaagagcgt caccatctgg cgggcagcgc tcacgcgcgc catcaaccag      420 gcgcggagg aagggcacct cgcgcgcgac tgcgatccgc gcctgatgct gttcgagatg       480
tacagccttg aactaggctt gcatcatgac gcccgtttcc tgcgcctgcc tgacagtgcc      540
gagcttgcca tggtcgcgct caacaagctg attcagtctt accgtacctg a               591
```

<210> SEQ ID NO 20
<211> LENGTH: 196
<212> TYPE: PRT
<213> ORGANISM: C. necator

<400> SEQUENCE: 20

```
Met Arg Lys Gly Glu Met Thr Arg Val Ala Ile Leu Asp Ala Ala Leu
1               5                   10                  15

Glu Leu Ser Ser Arg Asp Gly Leu Glu Gly Leu Thr Ile Gly Leu Leu
            20                  25                  30

Ala Glu Arg Met Gln Met Ser Lys Ser Gly Val Phe Ala His Phe Gly
        35                  40                  45

Ser Arg Glu Asp Leu Gln Val Glu Val Val Arg Glu Tyr His Arg Arg
    50                  55                  60

Phe Glu Gln Glu Val Phe Tyr Pro Ser Leu Gln Pro Arg Gly Leu
65                  70                  75                  80

Pro Arg Leu Trp Ser Met Val Arg Arg Trp Met Glu Lys Arg Ile Gln
                85                  90                  95

Glu Val Thr Thr Gly Cys Ile Tyr Ile Ser Gly Ala Val Glu Tyr Asp
            100                 105                 110

Asp Arg Ala Gly Ser Leu Val Arg Asp Glu Leu Val Lys Ser Val Thr
        115                 120                 125

Ile Trp Arg Ala Ala Leu Thr Arg Ala Ile Asn Gln Ala Arg Glu Glu
    130                 135                 140

Gly His Leu Arg Ala Asp Cys Asp Pro Arg Leu Met Leu Phe Glu Met
145                 150                 155                 160

Tyr Ser Leu Glu Leu Gly Leu His His Asp Ala Arg Phe Leu Arg Leu
                165                 170                 175

Pro Asp Ser Ala Glu Leu Ala Met Val Ala Leu Asn Lys Leu Ile Gln
            180                 185                 190

Ser Tyr Arg Thr
        195
```

<210> SEQ ID NO 21
<211> LENGTH: 1308
<212> TYPE: DNA
<213> ORGANISM: C. necator

<400> SEQUENCE: 21

```
atgtcttccg cagcaccgac caatattgct ggccaaaagc acgcactccc gtcttacctc      60
aatgccgacc atctcggccc ctggggcatc tacctgcagc aggtcgaccg tgtcacgcct      120
tacctgggct cgctggcacg ctgggtcgaa accctcaagc gccccaagcg cgcgatgatc      180
gtcgacgttc ccatcgaact ggataacggc accattgccc atttcgaggg ctatcgggtg      240
cagcacaacc tgtcgcgcgg cccgggcaag ggcggcgtgc gcttccacca ggacgtgacc      300
ctgtccgagg tgatggcgct gtcggcctgg atgtcggtga agaatgccgc ggtcaacgtg      360
```

```
ccctacggcg gtgccaaggg cggcatccgc gtcgatccgc gcacgctctc gcacgccgag    420
ctggaacgcc tgacgcgccg ctacaccagc gaaatcaaca tcatcatcgg gccgagcaag    480
gatattccgg cgccggacgt gaacaccaac gcccaggtca tggcctggat gatggacacg    540
tactcgatga actccggcag cacgccaccg gcgtggtga ccggcaagcc gatctcgctg    600
ggcggctcgc tcggccgcca cgaagccacc ggccgcggcg tgttcgtggt cggctccgag    660
gccgcgcgca atatcggcct ggagatcaag gcgcgcgcg tggcggtgca gggcttcggc    720
aacgtgggcg cggtggcggc caagctgttc catgaggccg cgccaaggt ggtggcggtg    780 caggaccacc gcaccacgct gttcgacccg gccggcctgg acgtgccggc gatgatggaa    840
tacgcctcgc acagcggcac catcgaaggc ttccgcggcg aagtcctgcg caccgagcag    900
ttctgggaag tcgactgcga catcctgatc ccggccgcgc tggaaggcca gatcacggtg    960
cagaacgcgc ccaagatcac ggcaaagctg gtgattgaag cgccaacgg cccgaccacg   1020 ccgcaagccg acgatatcct gcgcgagcgc aatatcctgg tctgtcccga cgtgatcgcc   1080
aacgccggcg gcgtgaccgt gtcctacttc gaatgggtgc aggatttctc cagcttttc   1140 tggaccgagg aagaaatcaa ccagcgcctg gtacggatca tgcaagaagc cttccgggca   1200
atctggcaag tggcacagga caacaaggtg acgctgcgca cggcggcgtt tatcgtggcc   1260
tgtacgcgga tcctgcaggc gcgcgagatg cgcggcctgt atccctga              1308
```

<210> SEQ ID NO 22
<211> LENGTH: 435
<212> TYPE: PRT
<213> ORGANISM: C. necator

<400> SEQUENCE: 22

```
Met Ser Ser Ala Ala Pro Thr Asn Ile Ala Gly Gln Lys His Ala Leu
1               5                   10                  15

Pro Ser Tyr Leu Asn Ala Asp His Leu Gly Pro Trp Gly Ile Tyr Leu
            20                  25                  30

Gln Gln Val Asp Arg Val Thr Pro Tyr Leu Gly Ser Leu Ala Arg Trp
        35                  40                  45

Val Glu Thr Leu Lys Arg Pro Lys Arg Ala Met Ile Val Asp Val Pro
    50                  55                  60

Ile Glu Leu Asp Asn Gly Thr Ile Ala His Phe Glu Gly Tyr Arg Val
65                  70                  75                  80

Gln His Asn Leu Ser Arg Gly Pro Gly Lys Gly Val Arg Phe His
            85                  90                  95

Gln Asp Val Thr Leu Ser Glu Val Met Ala Leu Ser Ala Trp Met Ser
            100                 105                 110

Val Lys Asn Ala Ala Val Asn Val Pro Tyr Gly Ala Lys Gly Gly
        115                 120                 125

Ile Arg Val Asp Pro Arg Thr Leu Ser His Ala Glu Leu Glu Arg Leu
    130                 135                 140

Thr Arg Arg Tyr Thr Ser Glu Ile Asn Ile Ile Ile Gly Pro Ser Lys
145                 150                 155                 160

Asp Ile Pro Ala Pro Asp Val Asn Thr Asn Ala Gln Val Met Ala Trp
            165                 170                 175

Met Met Asp Thr Tyr Ser Met Asn Ser Gly Ser Thr Ala Thr Gly Val
            180                 185                 190

Val Thr Gly Lys Pro Ile Ser Leu Gly Gly Ser Leu Gly Arg His Glu
        195                 200                 205
```

```
Ala Thr Gly Arg Gly Val Phe Val Gly Ser Glu Ala Ala Arg Asn
    210                 215                 220

Ile Gly Leu Glu Ile Lys Gly Ala Arg Val Ala Val Gln Gly Phe Gly
225                 230                 235                 240

Asn Val Gly Ala Val Ala Ala Lys Leu Phe His Glu Ala Gly Ala Lys
                245                 250                 255

Val Val Ala Val Gln Asp His Arg Thr Thr Leu Phe Asp Pro Ala Gly
                260                 265                 270

Leu Asp Val Pro Ala Met Met Glu Tyr Ala Ser His Ser Gly Thr Ile
            275                 280                 285

Glu Gly Phe Arg Gly Glu Val Leu Arg Thr Glu Gln Phe Trp Glu Val
        290                 295                 300

Asp Cys Asp Ile Leu Ile Pro Ala Ala Leu Glu Gly Gln Ile Thr Val
305                 310                 315                 320

Gln Asn Ala Pro Lys Ile Thr Ala Lys Leu Val Ile Glu Gly Ala Asn
                325                 330                 335

Gly Pro Thr Thr Pro Gln Ala Asp Asp Ile Leu Arg Glu Arg Asn Ile
                340                 345                 350

Leu Val Cys Pro Asp Val Ile Ala Asn Ala Gly Gly Val Thr Val Ser
            355                 360                 365

Tyr Phe Glu Trp Val Gln Asp Phe Ser Ser Phe Phe Trp Thr Glu Glu
        370                 375                 380

Glu Ile Asn Gln Arg Leu Val Arg Ile Met Gln Ala Phe Arg Ala
385                 390                 395                 400

Ile Trp Gln Val Ala Gln Asp Asn Lys Val Thr Leu Arg Thr Ala Ala
                405                 410                 415

Phe Ile Val Ala Cys Thr Arg Ile Leu Gln Ala Arg Glu Met Arg Gly
            420                 425                 430

Leu Tyr Pro
        435

<210> SEQ ID NO 23
<211> LENGTH: 339
<212> TYPE: DNA
<213> ORGANISM: C. necator

<400> SEQUENCE: 23
atgaagcaga ttaccgccat catcaaaccg ttcaagctcg acgaggtgcg tgaagccctg      60
gccgacgtcg gcgtgaccgg tctgacggtg accgaagtga agggatttgg ccgccagaaa     120
gggcataccg agctctaccg tggcgccgag tacgtggtcg acttcctgcc caagatcaag     180
atcgaagtgg tggtggccga gaaccagctg gacaccgtgc tggacgccat cgtcaaggcc     240
gcccacaccg gcaagatcgg cgacggcaag atcttcgtca ccgagatcga gcgtgtgatc     300
cgcatccgca ccggcgagca ggacgaagcc gcggtctga                            339

<210> SEQ ID NO 24
<211> LENGTH: 112
<212> TYPE: PRT
<213> ORGANISM: C. necator

<400> SEQUENCE: 24

Met Lys Gln Ile Thr Ala Ile Ile Lys Pro Phe Lys Leu Asp Glu Val
1               5                   10                  15

Arg Glu Ala Leu Ala Asp Val Gly Val Thr Gly Leu Thr Val Thr Glu
            20                  25                  30
```

```
Val Lys Gly Phe Gly Arg Gln Lys Gly His Thr Glu Leu Tyr Arg Gly
         35                  40                  45

Ala Glu Tyr Val Val Asp Phe Leu Pro Lys Ile Lys Ile Glu Val Val
 50                  55                  60

Val Ala Glu Asn Gln Leu Asp Thr Val Leu Asp Ala Ile Val Lys Ala
 65                  70                  75                  80

Ala His Thr Gly Lys Ile Gly Asp Gly Lys Ile Phe Val Thr Glu Ile
                 85                  90                  95

Glu Arg Val Ile Arg Ile Arg Thr Gly Glu Gln Asp Glu Ala Ala Val
                100                 105                 110
```

<210> SEQ ID NO 25
<211> LENGTH: 2412
<212> TYPE: DNA
<213> ORGANISM: C. necator

<400> SEQUENCE: 25

```
gtgaacgcgc gcaccggcgc tcccaatctt cccgatccgc tcggcgacga tgtcgtcggc      60
gagcgtgccg tcgcgcccgc gctggcgccg ggcaagtcca ggggcgcggc gctgcaggac     120
gagctggccg cgatgcagga tgtggcgccg gcggctgaca gcctgtttat cgacgcagtg     180
ctggcgcagt cataccggca cttcttcggc ccgacctcgc agccggcggt gccgccgcgc     240
cagcaggtca tctccatcac ccggctgatg gagaaactcg cgtacctgaa ggcgcccgac     300
ctggcgcgcg tgcgcgaggc cttccagttt ccgacgaagc ccacctgggc cagtaccgc      360
cagagcggtg agccctacat cacccatccg gtggcggtgg ccgagctgtg cgcggactgg     420
aagctggatg tgcagtccat catggcggcg ctgctgcacg acgtgatgga agaccagggc     480
atcaccaaga gcgagctggt cgagaaattc ggccccaagg tcgccgaact ggtcgacggc     540
ctgaccaaat tggacaagct cgaattccag agccgcgagc aggcgcaggc ggagagcttc     600
cgcaagatgc tgctggcgat ggcgcgcgac gtgcgcgtga tcctggtgaa gctggccgac     660
cgtacgcaca acatgcgcac gctcgacttc gtcccgccgg agaagcgccg ccgcatcgcg     720
ctggagacca tggagatcta tgcgccgatc gcgcaccgtc tcggtctcaa cacgatctac     780
cgcgagctgc aggagctgtc cttcaaggtc ggctcgccgt tccgctacgc cacgctggaa     840
aaagccgtca aggccgcgcg cggcaaccgc gcgaggtgg tcaagcgtat cctggaagcc     900
gcgcagaagg gctggccga cgccggcatc gtggccgaac tgtccgggcg cgagaaaacg     960
ctctacagca tctaccgcaa gatgcacgac aagcagctgt cgttctcgca ggtgctggac    1020
gtatatggtt ccgcgtggt ggtggaaacg cagatgcact gctacatggc gatgggcgcg    1080
ctgcatgggc tgtacaagcc catgcccggc aagttcaagg actacatcgc catccccaag    1140
atcaacggct accagtcgct gcacaccacg ctggtgggtc cgttcggcac gccggtggag    1200
ttccagatcc gcacgcgcga catgcaccag atcgccgagg ccggcgtggc cgcgcactgg    1260
atgtacaagc accaggccga tcacgccaac gatatccagc agcaggcgca ccagtggctg    1320
cagtcgctgc tcgatatcca gagccagacc ggcgattcgc aggaattcct cgagcacgtc    1380
aagatcgacc tgttcccgga tgcggtctac gtgttcacgc ccaagggcca tatccgcgcg    1440
ctgccgcgcg gcgccaccgc gctggacttt gcctacgcgg tgcacagcga cctgggcaac    1500
cagtgcgtcg cggtcaagat caacaacgag atgttgccgc tgcgcaccga gctcaagagc    1560
ggcgatatcg tcgaggtggt gacggcgccg tactccaagc ccaatccggc gtggctgtcg    1620
ttcgtgcgca ccggcaaggc gcgcgcggcg atccgccact acctgaagac caccaagctc    1680
```

-continued

```
gacgaagcca tccagcttgg cgagcgcctg ctggaacagt cggcgcgcca gctcggcttc    1740
gagctcaagg cggtgccgca gtcggtgtgg gaccgcatgg tgcagtggac cggcaacaag    1800
cagcgcgaag acatctttgc cgacctggca ctgggccggc gcgtgccggc ggtggtggcc    1860
aagcgcatgg agatcctgct ccaggagctg tccggcgatg tcgacagcgc gctgctggcg    1920
gcggtgcaga ccttcgccgg cgaagaagcg cccgcggtgc cgatcaccgg cgacgaaggc    1980
atgtcgatga tcttctcggc gtgctgccgc ccgatcccgg cgactccat cgttggctac     2040 ctgggcaagg gcgaagggct gcagatccac gtgcaggact gcaagatcgc caagcgcctg    2100
cacagcaagg atccggagca ctggatcgac gtgatgtggg ccaagaagac cacgcgcgcc    2160
ttcgacgtgt cgatcaaggt gatggtgcgc aacgtcaagg gcatcgttgc gcgcgtggct    2220
gccgacctga ccgccgccga cgccaacgtc gcgcacgtgg ccatggagca gcaggacgcc    2280
ggccaccagg aagccaccta tgcagtttt atcatccagg tgcagaaccg cctgcacctg     2340
gccaacgtga tgcgcgggct cgccgcaac ccggacgtca tccggatatt ccgcgaccgc     2400
aacgacggct ag                                                        2412
```

<210> SEQ ID NO 26
<211> LENGTH: 803
<212> TYPE: PRT
<213> ORGANISM: C. necator

<400> SEQUENCE: 26

```
Met Asn Ala Arg Thr Gly Ala Pro Asn Leu Pro Asp Pro Leu Gly Asp
1               5                   10                  15

Asp Val Val Gly Glu Arg Ala Val Ala Pro Ala Leu Ala Pro Gly Lys
                20                  25                  30

Ser Arg Gly Ala Ala Leu Gln Asp Glu Leu Ala Ala Met Gln Asp Val
            35                  40                  45

Ala Pro Ala Ala Asp Ser Leu Phe Ile Asp Ala Val Leu Ala Gln Ser
        50                  55                  60

Tyr Arg His Phe Phe Gly Pro Thr Ser Gln Pro Ala Val Pro Pro Arg
65                  70                  75                  80

Gln Gln Val Ile Ser Ile Thr Arg Leu Met Glu Lys Leu Ala Tyr Leu
                85                  90                  95

Lys Ala Pro Asp Leu Ala Arg Val Arg Glu Ala Phe Gln Phe Ser Asp
            100                 105                 110

Glu Ala His Leu Gly Gln Tyr Arg Gln Ser Gly Glu Pro Tyr Ile Thr
        115                 120                 125

His Pro Val Ala Val Ala Glu Leu Cys Ala Asp Trp Lys Leu Asp Val
    130                 135                 140

Gln Ser Ile Met Ala Ala Leu Leu His Asp Val Met Glu Asp Gln Gly
145                 150                 155                 160

Ile Thr Lys Ser Glu Leu Val Glu Lys Phe Gly Pro Lys Val Ala Glu
                165                 170                 175

Leu Val Asp Gly Leu Thr Lys Leu Asp Lys Leu Glu Phe Gln Ser Arg
            180                 185                 190

Glu Gln Ala Gln Ala Glu Ser Phe Arg Lys Met Leu Leu Ala Met Ala
        195                 200                 205

Arg Asp Val Arg Val Ile Leu Val Lys Leu Ala Asp Arg Thr His Asn
    210                 215                 220

Met Arg Thr Leu Asp Phe Val Pro Pro Glu Lys Arg Arg Arg Ile Ala
225                 230                 235                 240
```

```
Leu Glu Thr Met Glu Ile Tyr Ala Pro Ile Ala His Arg Leu Gly Leu
            245                 250                 255

Asn Thr Ile Tyr Arg Glu Leu Gln Glu Leu Ser Phe Lys Val Gly Ser
            260                 265                 270

Pro Phe Arg Tyr Ala Thr Leu Glu Lys Ala Val Lys Ala Ala Arg Gly
            275                 280                 285

Asn Arg Arg Glu Val Val Lys Arg Ile Leu Glu Ala Ala Gln Lys Gly
            290                 295                 300

Leu Ala Asp Ala Gly Ile Val Ala Glu Leu Ser Gly Arg Glu Lys Thr
305                 310                 315                 320

Leu Tyr Ser Ile Tyr Arg Lys Met His Asp Lys Gln Leu Ser Phe Ser
            325                 330                 335

Gln Val Leu Asp Val Tyr Gly Phe Arg Val Val Glu Thr Gln Met
            340                 345                 350

His Cys Tyr Met Ala Met Gly Ala Leu His Gly Leu Tyr Lys Pro Met
            355                 360                 365

Pro Gly Lys Phe Lys Asp Tyr Ile Ala Ile Pro Lys Ile Asn Gly Tyr
            370                 375                 380

Gln Ser Leu His Thr Thr Leu Val Gly Pro Phe Gly Thr Pro Val Glu
385                 390                 395                 400

Phe Gln Ile Arg Thr Arg Asp Met His Gln Ile Ala Glu Ala Gly Val
            405                 410                 415

Ala Ala His Trp Met Tyr Lys His Gln Ala Asp His Ala Asn Asp Ile
            420                 425                 430

Gln Gln Gln Ala His Gln Trp Leu Gln Ser Leu Leu Asp Ile Gln Ser
            435                 440                 445

Gln Thr Gly Asp Ser Gln Glu Phe Leu Glu His Val Lys Ile Asp Leu
            450                 455                 460

Phe Pro Asp Ala Val Tyr Val Phe Thr Pro Lys Gly His Ile Arg Ala
465                 470                 475                 480

Leu Pro Arg Gly Ala Thr Ala Leu Asp Phe Ala Tyr Ala Val His Ser
            485                 490                 495

Asp Leu Gly Asn Gln Cys Val Ala Val Lys Ile Asn Asn Glu Met Leu
            500                 505                 510

Pro Leu Arg Thr Glu Leu Lys Ser Gly Asp Ile Val Glu Val Val Thr
            515                 520                 525

Ala Pro Tyr Ser Lys Pro Asn Pro Ala Trp Leu Ser Phe Val Arg Thr
            530                 535                 540

Gly Lys Ala Arg Ala Ala Ile Arg His Tyr Leu Lys Thr Thr Lys Leu
545                 550                 555                 560

Asp Glu Ala Ile Gln Leu Gly Glu Arg Leu Leu Glu Gln Ser Ala Arg
            565                 570                 575

Gln Leu Gly Phe Glu Leu Lys Ala Val Pro Gln Ser Val Trp Asp Arg
            580                 585                 590

Met Val Gln Trp Thr Gly Asn Lys Gln Arg Glu Asp Ile Phe Ala Asp
            595                 600                 605

Leu Ala Leu Gly Arg Arg Val Pro Ala Val Ala Lys Arg Met Glu
            610                 615                 620

Ile Leu Leu Gln Glu Leu Ser Gly Asp Val Asp Ser Ala Leu Leu Ala
625                 630                 635                 640

Ala Val Gln Thr Phe Ala Gly Glu Glu Ala Pro Ala Val Pro Ile Thr
            645                 650                 655
```

Gly Asp Glu Gly Met Ser Met Ile Phe Ser Ala Cys Cys Arg Pro Ile
            660                 665                 670

Pro Gly Asp Ser Ile Val Gly Tyr Leu Gly Lys Gly Glu Gly Leu Gln
        675                 680                 685

Ile His Val Gln Asp Cys Lys Ile Ala Lys Arg Leu His Ser Lys Asp
    690                 695                 700

Pro Glu His Trp Ile Asp Val Met Trp Ala Lys Lys Thr Thr Arg Ala
705                 710                 715                 720

Phe Asp Val Ser Ile Lys Val Met Val Arg Asn Val Lys Gly Ile Val
                725                 730                 735

Ala Arg Val Ala Ala Asp Leu Thr Ala Ala Asp Ala Asn Val Ala His
            740                 745                 750

Val Ala Met Glu Gln Gln Asp Ala Gly His Gln Glu Ala Thr Tyr Met
        755                 760                 765

Gln Phe Ile Ile Gln Val Gln Asn Arg Leu His Leu Ala Asn Val Met
    770                 775                 780

Arg Gly Leu Arg Arg Asn Pro Asp Val Ile Arg Ile Phe Arg Asp Arg
785                 790                 795                 800

Asn Asp Gly

<210> SEQ ID NO 27
<211> LENGTH: 948
<212> TYPE: DNA
<213> ORGANISM: C. necator

<400> SEQUENCE: 27
atgcgcgacc gaatcctagc cgtctacgac acgctccgcc cttctgaacg ccgcctggcc      60
gactatgtcg cccggcatgg cgccgccgtg atccggctgt cgatgcccga gctggccgag     120
cgcgccggcg tgtcgcagcc caccatcgcg cgcttctgcg cggcgctggg ctacgacggc     180
ttccgcgaat tcaagctgca gttcgcgcag aacgttggcg gcggcacgcc cttcgtgcac     240
caggacgtcg cggccgacga ccgccccgcg gacatcgccg gcaaggtctt cgaccgcacc     300
attgccacgc tgatgagcgt gcgcaatgcg ctgtcggccg accagatcga gcatggcatc     360
cagctgctcg ccggcgcgcg ccgcatcgag ttctacggct gcggcaactc cggcatcgtc     420
gcgctggata tccagcacaa gttcttccgc ctgggcatgc cgacggttgc gtattccgac     480
ccgcacgtgt tcagcatgtc ggccgcgctg ctcgcccgtg gcgacgtggc cgtgctggtc     540
tccaacagcg gccgcacctg ggacatgctg accgctgcca cgctggcgcg cagcagcggc     600
gccagcgtgc tggcaatcac gcacagcggc tcgccgctgg cgcggctggc tgacgtctgc     660
gtgttttccg acgtcgagga agacagcgag gtctacacgc cgatgacctc gcgcatcagc     720
cacctggtgc tgggcgacgt cctggccgcc ggcgtggcgc ttgcgcgcgc cgacaccgtc     780 gcccccccgcc tgcagcgcgc caaggcgcat ctgcgcgaac gacgcattgc cggtgcggag     840 ccggccggc cagtaccgcc ggcacgaaac cgcgccaggc ccgccgcagc cgagccagcc      900
acgcccgcgc tgcccgccac ccgcacgcgt cgccgcaagg ccagttga                  948

<210> SEQ ID NO 28
<211> LENGTH: 315
<212> TYPE: PRT
<213> ORGANISM: C. necator

<400> SEQUENCE: 28

Met Arg Asp Arg Ile Leu Ala Val Tyr Asp Thr Leu Arg Pro Ser Glu
1               5                   10                  15

Arg Arg Leu Ala Asp Tyr Val Ala Arg His Gly Ala Ala Val Ile Arg
            20                  25                  30

Leu Ser Met Pro Glu Leu Ala Glu Arg Ala Gly Val Ser Gln Pro Thr
        35                  40                  45

Ile Ala Arg Phe Cys Ala Ala Leu Gly Tyr Asp Gly Phe Arg Glu Phe
    50                  55                  60

Lys Leu Gln Phe Ala Gln Asn Val Gly Gly Thr Pro Phe Val His
65                  70                  75                  80

Gln Asp Val Ala Ala Asp Asp Arg Pro Ala Asp Ile Ala Gly Lys Val
                85                  90                  95

Phe Asp Arg Thr Ile Ala Thr Leu Met Ser Val Arg Asn Ala Leu Ser
            100                 105                 110

Ala Asp Gln Ile Glu His Gly Ile Gln Leu Leu Ala Gly Ala Arg Arg
        115                 120                 125

Ile Glu Phe Tyr Gly Cys Gly Asn Ser Gly Ile Val Ala Leu Asp Ile
130                 135                 140

Gln His Lys Phe Phe Arg Leu Gly Met Pro Thr Val Ala Tyr Ser Asp
145                 150                 155                 160

Pro His Val Phe Ser Met Ser Ala Ala Leu Leu Ala Arg Gly Asp Val
                165                 170                 175

Ala Val Leu Val Ser Asn Ser Gly Arg Thr Trp Asp Met Leu Thr Ala
            180                 185                 190

Ala Thr Leu Ala Arg Ser Ser Gly Ala Ser Val Leu Ala Ile Thr His
        195                 200                 205

Ser Gly Ser Pro Leu Ala Arg Leu Ala Asp Val Cys Val Phe Ser Asp
    210                 215                 220

Val Glu Glu Asp Ser Glu Val Tyr Thr Pro Met Thr Ser Arg Ile Ser
225                 230                 235                 240

His Leu Val Leu Gly Asp Val Leu Ala Ala Gly Val Ala Leu Ala Arg
                245                 250                 255

Ala Asp Thr Val Ala Pro Arg Leu Gln Arg Ala Lys Ala His Leu Arg
            260                 265                 270

Glu Arg Arg Ile Ala Gly Ala Glu Pro Ala Arg Pro Val Pro Pro Ala
        275                 280                 285

Arg Asn Arg Ala Arg Pro Ala Ala Ala Glu Pro Ala Thr Pro Ala Leu
    290                 295                 300

Pro Ala Thr Arg Thr Arg Arg Lys Ala Ser
305                 310                 315

<210> SEQ ID NO 29
<211> LENGTH: 2229
<212> TYPE: DNA
<213> ORGANISM: C. necator

<400> SEQUENCE: 29
atggtgacgt ccaccgacct gaccggtcgg gtcgcgggca ttccggatgc cgaactggtc      60
gaacgcgcac tggcctacgt gcgcgagcat ggtgccgagg tagcgctgcc caccggcgag     120
accgtgctgt cgcacgcgca gggcatgctg cgcattctcg acggcctgcg cgtcgacgac     180
gccgcgcgtg ccgccgcctg cctgttcggg ctggtggcct tcgtgcccgg taccgaggcc     240
gagatcgcac cgcgctttgg agacgaggtg gcacggctgg tcgacggtgt gcggcagctg     300
ctgcgcatcg gtgccatcgc cggcagccgc ccgaggccg agccggccgc gccgtccaag     360
aacgaagcgc aggcgcgcca cgaacaggtc gaggcgctgc gcaagatgct gctggcgttt     420

```
gcgcaggaca tccgcgtggt gctggtgcgc ctggcctcgc ggctgcagac cctgcgctgg      480
ctggccgaga ccaagcaggc gccgcagccg ggcgtggcgc gcgaaacgct ggacatctac      540
gcgccgctgg ccaatcgcct tggtatctgg cagatgaagt gggaactgga ggacctggcg      600
ttccgcttcg agcagcccga tacctacaag cgcatcgcca actgctgga cgagaagcgc       660 atcgagcgcg aaggctatat cggcggcgcc atcgaacggc tgcagtccga gctggcgact      720
gccggcatcc gtgccgaggt cagcggcgg cccaagcata tctacagcat ctggaagaag       780
atgcgcggca aggagctgga ttttgccgac ctgtacgatg tgcgcgcctt ccgcgtgatc      840
gtcgacgata tcaaggactg ctacacggtg ctgggtatcg tccaccatat ctggcagccg      900
atcccgcgcg agttcgacga ctatatctcg cggcccaagg ccaatggcta caaatcgctg      960
catacggtgg tgatcggcga tgacgggcgc gccttcgagg tgcagatccg cacgcatgag     1020
atgcaccact ttgccgaata cggcgtggcc gcgcactggc gctacaagga agcgggcagc     1080
cgcggctatg ccgggcagtt ctccgccagc gagcgctatg acgagaagat tgcctggctg     1140
cgccagctgc tggcgtggaa ggacgatgcc gaccacagcg tggcgcacga tgaatcgtgg     1200
gagcagatca agcacgccgc gatcgacgac cacatctacg tgctgacgcc gcaggcgcgc     1260
gtggtggcgc tgccgcaggg cgccaccgcg gtggactttg cctactacct gcacagcgat     1320
ctcggccacc gctgccgcgg cgcgcgcgtg acggcacca tggtgccgct gaacacgccg      1380
ctgaagaacg ccagaccgt ggagatcatc gcggtcaagc agggcggacc gtcgcgcgac      1440
tggctcaacg cggacctggg ctacctggcc agcagccgcg cgcgggccaa ggtgcgggcc     1500
tggttcaatg cgctcgattc gcaggagacc atcgcccagg gccgcgtgct gatcgacaag     1560
accctgcagc gcgaaggcaa gaccgcggtc aagctggaag acctggccac gcggctgggc     1620
ttcaagacgc cggaggacct gttttgcggca gtggccaagg acgagttcag tctgcgccac     1680
gtggagcacg cgctgcgaca cccggaggc gaggtccagg cgccgctgag cgaggaagac      1740
gctgtcacca agaagagccg cgccaccagc gtggcgcgcg cgccaagag cggcgtgctg     1800 gtggtgggg tggattcgct gatgacgcag atgtcgcgct gctgcaagcc ggcgccgccg     1860
gacgacatcg tcggctttgt cacgcgcggg cgcggggtgt cgatccatcg gcgcagctgc     1920
cacaccttcc agcaactggc cgggcgcgcg ccggagcggg tgatccagac cgagtggggc     1980
cagaagagcc acgccgcggt ctatccggtc gatatccatg tcgaggcgat cgatcgccag    2040
gggctgctgc gcgatatctc cgaagtgctg tcgcgcgaga agatcaatgt caccggcgtc     2100
aagacgctct ccagcaaggg cgttgcgcgc atgcagttca ctgccgaagt gtccgaggct     2160
acgcagctgc agcgcgcgct gcagttgatc gaagacgtcc aggggggtgtt gcaggcgaaa   2220 agaaagtga                                                             2229
```

<210> SEQ ID NO 30
<211> LENGTH: 742
<212> TYPE: PRT
<213> ORGANISM: C. necator

<400> SEQUENCE: 30

Met Val Thr Ser Thr Asp Leu Thr Gly Arg Val Ala Gly Ile Pro Asp
1               5                   10                  15

Ala Glu Leu Val Glu Arg Ala Leu Ala Tyr Val Arg Glu His Gly Ala
            20                  25                  30

Glu Val Ala Leu Pro Thr Gly Glu Thr Val Leu Ser His Ala Gln Gly
        35                  40                  45

```
Met Leu Arg Ile Leu Asp Gly Leu Arg Val Asp Asp Ala Ala Arg Ala
 50                  55                  60

Ala Ala Cys Leu Phe Gly Leu Val Ala Phe Val Pro Gly Thr Glu Ala
 65                  70                  75                  80

Glu Ile Ala Pro Arg Phe Gly Asp Glu Val Ala Arg Leu Val Asp Gly
                 85                  90                  95

Val Arg Gln Leu Leu Arg Ile Gly Ala Ile Ala Gly Ser Arg Pro Glu
                100                 105                 110

Ala Glu Pro Ala Ala Pro Ser Lys Asn Glu Ala Gln Ala Arg His Glu
            115                 120                 125

Gln Val Glu Ala Leu Arg Lys Met Leu Leu Ala Phe Ala Gln Asp Ile
130                 135                 140

Arg Val Val Leu Val Arg Leu Ala Ser Arg Leu Gln Thr Leu Arg Trp
145                 150                 155                 160

Leu Ala Glu Thr Lys Gln Ala Pro Gln Pro Gly Val Ala Arg Glu Thr
                165                 170                 175

Leu Asp Ile Tyr Ala Pro Leu Ala Asn Arg Leu Gly Ile Trp Gln Met
                180                 185                 190

Lys Trp Glu Leu Glu Asp Leu Ala Phe Arg Phe Glu Gln Pro Asp Thr
            195                 200                 205

Tyr Lys Arg Ile Ala Lys Leu Leu Asp Glu Lys Arg Ile Glu Arg Glu
210                 215                 220

Gly Tyr Ile Gly Gly Ala Ile Glu Arg Leu Gln Ser Glu Leu Ala Thr
225                 230                 235                 240

Ala Gly Ile Arg Ala Glu Val Ser Gly Arg Pro Lys His Ile Tyr Ser
                245                 250                 255

Ile Trp Lys Lys Met Arg Gly Lys Glu Leu Asp Phe Ala Asp Leu Tyr
                260                 265                 270

Asp Val Arg Ala Phe Arg Val Ile Asp Asp Ile Lys Asp Cys Tyr
            275                 280                 285

Thr Val Leu Gly Ile Val His His Ile Trp Gln Pro Ile Pro Arg Glu
290                 295                 300

Phe Asp Asp Tyr Ile Ser Arg Pro Lys Ala Asn Gly Tyr Lys Ser Leu
305                 310                 315                 320

His Thr Val Val Ile Gly Asp Asp Gly Arg Ala Phe Glu Val Gln Ile
                325                 330                 335

Arg Thr His Glu Met His His Phe Ala Glu Tyr Gly Val Ala Ala His
                340                 345                 350

Trp Arg Tyr Lys Glu Ala Gly Ser Arg Gly Tyr Ala Gly Gln Phe Ser
            355                 360                 365

Ala Ser Glu Arg Tyr Asp Glu Lys Ile Ala Trp Leu Arg Gln Leu Leu
370                 375                 380

Ala Trp Lys Asp Asp Ala Asp His Ser Val Ala His Asp Glu Ser Trp
385                 390                 395                 400

Glu Gln Ile Lys His Ala Ala Ile Asp Asp His Ile Tyr Val Leu Thr
                405                 410                 415

Pro Gln Ala Arg Val Val Ala Leu Pro Gln Gly Ala Thr Ala Val Asp
            420                 425                 430

Phe Ala Tyr Tyr Leu His Ser Asp Leu Gly His Arg Cys Arg Gly Ala
435                 440                 445

Arg Val Asp Gly Thr Met Val Pro Leu Asn Thr Pro Leu Lys Asn Gly
450                 455                 460
```

```
Gln Thr Val Glu Ile Ile Ala Val Lys Gln Gly Gly Pro Ser Arg Asp
465                 470                 475                 480

Trp Leu Asn Ala Asp Leu Gly Tyr Leu Ala Ser Ser Arg Ala Arg Ala
                485                 490                 495

Lys Val Arg Ala Trp Phe Asn Ala Leu Asp Ser Gln Glu Thr Ile Ala
            500                 505                 510

Gln Gly Arg Val Leu Ile Asp Lys Thr Leu Gln Arg Glu Gly Lys Thr
        515                 520                 525

Ala Val Lys Leu Glu Asp Leu Ala Thr Arg Leu Gly Phe Lys Thr Pro
    530                 535                 540

Glu Asp Leu Phe Ala Ala Val Ala Lys Asp Glu Phe Ser Leu Arg His
545                 550                 555                 560

Val Glu His Ala Leu Arg His Pro Glu Gly Glu Val Gln Ala Pro Leu
                565                 570                 575

Ser Glu Glu Asp Ala Val Thr Lys Lys Ser Arg Ala Thr Ser Val Ala
            580                 585                 590

Arg Gly Ala Lys Ser Gly Val Leu Val Gly Val Asp Ser Leu Met
        595                 600                 605

Thr Gln Met Ser Arg Cys Cys Lys Pro Ala Pro Pro Asp Asp Ile Val
610                 615                 620

Gly Phe Val Thr Arg Gly Arg Gly Val Ser Ile His Arg Arg Ser Cys
625                 630                 635                 640

His Thr Phe Gln Gln Leu Ala Gly Arg Ala Pro Glu Arg Val Ile Gln
                645                 650                 655

Thr Glu Trp Gly Gln Lys Ser His Ala Ala Val Tyr Pro Val Asp Ile
            660                 665                 670

His Val Glu Ala Ile Asp Arg Gln Gly Leu Leu Arg Asp Ile Ser Glu
        675                 680                 685

Val Leu Ser Arg Glu Lys Ile Asn Val Thr Gly Val Lys Thr Leu Ser
    690                 695                 700

Ser Lys Gly Val Ala Arg Met Gln Phe Thr Ala Glu Val Ser Glu Ala
705                 710                 715                 720

Thr Gln Leu Gln Arg Ala Leu Gln Leu Ile Glu Asp Val Gln Gly Val
                725                 730                 735

Leu Gln Ala Lys Arg Lys
            740
```

<210> SEQ ID NO 31
<211> LENGTH: 4857
<212> TYPE: DNA
<213> ORGANISM: C. necator

<400> SEQUENCE: 31

```
atgccgcagg agaacgaaga caaggtcgcg cacctgctgg acgaactggc cagcttcgcg      60
cgcgagcggc tgccggcggc gatgttcgcc gtggtcgagc ccttcctgct gcactactac     120
gatcaggccg acgccgagga cttgctccag cgcgacgtcg acgatctcta cggcgccgtg     180
atggcgcact ggcagaccgc acagaaattc accccccggca atgcgcgcat ccgcgtctac     240
aatcccaacc tggaagagca cggctggcac tcggaccaca ccgtggtcga gatcgtcaat     300
gacgacatgc ccttcctggt cgactcggtg acgatggaga tcaaccggca gggactggcg     360
ctgcactcgg ccatccatcc cgtgttccgg gtctggcgcg acgcgcgcgg cggcatcgag     420
cggatcgccc cgggcggcgc cggcgaggcc ggggacagct cgcgcctgga atcctttatc     480
catttcgaga tcgaccgcag cggcgaggcc gcgcggctgg aggcgctgcg cagcggcatt     540
```

```
gcgcaggtgc tggtcgacgt gcgcgcggcg gtggaagact ggtcgaagat gtgcggcatc    600
acccaggcca ccatcgccgc catggcgcag gcgcccgacg cggccgcgcc ggagagcgtc    660
gaggcgcgcg ccttcctgga ctggatgatg gatgaccact tctccttcct cggccagcgt    720
gactaccagc tggtgtcgca ggacggccgc tacttcctgc gcggcgtgcc gggctcgggc    780
gcgggcatcc tgcgcgaaag cctgcgcgag cctgatgccg aagatctcac gctgctgccc    840
gccgcggcca ccgcgatcat cgaaggggcc tcgccgatct tcctgaccaa ggccaattcg    900
cgcgccaccg tgcaccgccc gggctatctc gactatgtcg gcgtcaagct gctcgatgaa    960
aaggggcagc tgttcggcga gcggcgcttt gtcggcctgt acacctcgac tgcctatacg    1020
gcgccgattg cggaaattcc gctggtgcgg ctcaagtgcg ccaatatcct ggcgcgcgcg    1080
ggcttcctgg ccaaggggca cctttacaag tcgctggtga ccatccttga gcaatatccg    1140
cgcgatgaac tgttccaggc caccgaggat gaactgttcg acatcaccac cggcatcctg    1200
cggctgcagg aacaccagcg cacccggctc tttgtacggc gcgaccgctt cgaccgcttt    1260
gtctcgtgcc tggtgttcgt gccgcgcgac aagtacaaca ccgacctgcg ccagaagatc    1320
cagaggctgc tgaccgcggc cttccacgga ccagctgcg agttcacgcc gctgctgtcc    1380
gagtcgccgc tggcgcgcat ccagctgacc gtgcgcggcg agcccggcac catgccgcat    1440
gttgatacgc gtgagctgga ggcgcgcatc gtgcacgcca ccgccgctg caggacgat     1500 ctcgccgaag ccctgcatga aagccacggc gaagagcaag gcaaccggct gctgcagcgc    1560
tacgcgggct cgttccccgc cggctaccgt gaggactacc cggcccgcac cgcggtgcgc    1620
gatatcgagc tgatggagca cgcgctgcgc ggcaacggca tggcgatgaa cctgtaccgg    1680
ccgatcgagg ccgcgccggg ggtgttccgc ttcaaggtgt accgtgccgg cgagccgatc    1740
gcgctgtcgc acagcctgcc catgctggaa cacctgggcg tgcgcgtgga tgaagagcgc    1800
ccctacctga tcgaaccga cagcggcgcg ccggtatggg tgcacgactt cgggctggag    1860
attgccgaca gcggcggcgc ggcggaattc gacatcgcgc gcgtcaaggc cttgttcgag    1920
gatgcgttcg cgcgcgcctg gcacggcgag atcgagaacg acgacttcaa ccgcctggtg    1980
ctgcgcgccg agctggccgc acgcgacgtc accatcctgc gcgcctatgc ccgctacctg    2040
cgccaggtag gctcgacctt cagcgacgcc tatatcgagc gcgcgctgac cggcaacgcg    2100
gccattgccg ccatgctggt cggcctgttc gtggcgcgct tcgacacctt cagcgaggtc    2160
gccaccgaca ccgcccgcca ggcgcgctgc gacaagctgc tggccgatat cggcgcggcg    2220
ctggacaagt gcccaacct ggacgaggac cgcatcctgc ggcttttcct gggcgtgatc    2280
aacgccaccg tgcgcaccaa ctatttccac cgcggcgagg aaggccagcc gcgcccatat    2340
gtgtcgttca agttcaatcc cgcgctggtc cccggcctgc ccgagccgcg cccgatgttc    2400
gagatctggg tctactcgcc gcgcgttgag ggcgtgcacc tgcgcggcgg gcgcgtggcc    2460
cgcggcggac tgcgctggtc agaccggcgc gaggacttcc gcactgaagt gctgggcctg    2520
atgaaggcgc agatggtcaa gaacacggtg atcgtgccgg tgggctccaa gggcggcttc    2580
gtggtcaagc gcccgccccc gcccaccgac cgcgatgcgt tcctgcagga gggcatcgcc    2640
tgctaccaga ccttcctgcg cgggctgctg gacctcaccg acaacctcgt cggcggccag    2700
ctggtgccgc cacccgaggt ggtgcgccac gacgacaacg accctacct ggtggtcgcc     2760 gccgacaagg gcaccgcgac gttctccgac ttcgccaacg cgatctcggc cgaatacggc    2820
ttctggctgg gcgatgcctt tgcgtccggg ggctcggtcg gctatgacca caagaagatg    2880
```

```
ggcattaccg cgcgcggtgc gtgggaatcg gtcaagcggc atttccgcga gatgggtgtc    2940
gatatccaga ccacggactt caccgtggcc ggcatcggcg acatgtcggg cgatgtgttc    3000
ggcaacggca tgctgctgtc gccgcatatc cggctggtgg cggctttcga ccaccggcat    3060
atcttcctcg atcccgaccc ggacacgaca aggagcctgc aggaacgcac gcggctgttc    3120
ggcctgcccc gctcaagctg gccgactac gacgccacgc tgatttccgc cggcggcggc    3180
atctatccgc gcagcgccaa gaccatcgcg ctgtcgccgc aggtgcaggc ggtgctgggg    3240
gtcacggcag ccacgctgtc gccggccgag ctgatccacg ccatcctgat ggcgccggtc    3300
gacctgctct acaacggcgg catcggcact tacgtcaagt ccagccagga aacccacctg    3360
caggccggcg accgcaccaa cgacgcggtg cgtgtcaacg caatgacct gcgctgcaag     3420 gtggtcggcg aaggcggcaa cctcggcttc acccagctgg gccgcatcga gttcgcgcgc    3480
aagggcgggc gcatcaacac cgacgccatc gacaactcgg ccggggtgga ctgctcggac    3540
cacgaggtca atatcaagat cctgctcggg ctggtggttg ccgacggcga aatgaccgag    3600
aagcagcgca acaagctgct ggccgagatg accgacgagg tcggcctgct ggtgctgcag    3660
gacaactact accagaccca ggcactgtcc gtggccgggc gcagcagccc cgcgctgctc    3720
gacggcgagg cgcgcctggt gcgctggctg gagcgcgccg acggctcaa ccggccgctg     3780 gagttcctgc cttcggagga gaaaatcgcc gagcgcaagc tggccgatga aggcctggca    3840
tcgcccgagc gtgccgtgct gcttgcctac agcaagatgt ggctgtacga cgaactgctg    3900
gcctccgacg tgccggaaga cacgctggtc gccggactgc tgtcggacta tttcccggtg    3960
ccgctgcgcc agcgttacgc cgacgcgatg cagcgccacc cgctgcggcg cgagatcctg    4020
tcgacacacc tgaccaatat gctggtcaac cgtatcggcg ccaccttcgt gcaccggatc    4080
atggaagaga ccgacgcacg cccggccgat atcgtgcgcg cctgcctgat cgcacgcgat    4140
gtcttcggcc tgaccaccct gtggcaggag atcgatgcgc tggacaaccg tgtggccgat    4200
gccgagcagg cgcgcatgtt cggggccgtg gcgctgctgc tggagcgcgc gtgcctgtgg    4260
ttcatccgct atctgcgcag cggcagcaag gccgccgagg acctggcgcg ctttgcccag    4320
gccgcgcaat ggctggcccc gcaactgccg cggctgctgc cgccggccga tgcgacggca    4380
ctgtcagagc gcgcccgggc cttgacggat gcaggggtcg acgaagcgct ggctgtgcgc    4440
gtggccggca gcgagatctc cgccgccgcg ctcgatatcg ccgaagtggc cacggcgtgc    4500
aaacgcagcc tggacctggt ggcggggggtt tatttcgcgc tggacagcca cctgagcttc    4560
agctggctgc gcgagcgcgc gctggcgctg ccatcggaca cgcactggga cctgctggca    4620
cgcaccacca cgctggaaga cctggggcgg ctcaagcgcg cactgaccgt cagcgtgctg    4680
tcacaggagg gtgaactgga tacgcccgac gccatgatcg atgcctggcg ctccagccgt    4740
catggcgcgc tggaacgctt tacgcgcatg ctggccgacc agcgcgcctc ggggctgcg     4800 gggctgtcga tgctgtcggt cgcggtgcgc gagatcggca tgctggaacg cgcatag      4857
```

<210> SEQ ID NO 32
<211> LENGTH: 1618
<212> TYPE: PRT
<213> ORGANISM: C. necator

<400> SEQUENCE: 32

Met Pro Gln Glu Asn Glu Asp Lys Val Ala His Leu Leu Asp Glu Leu
1               5                   10                  15

Ala Ser Phe Ala Arg Glu Arg Leu Pro Ala Ala Met Phe Ala Val Val
            20                  25                  30

```
Glu Pro Phe Leu Leu His Tyr Tyr Asp Gln Ala Asp Ala Glu Asp Leu
            35                  40                  45

Leu Gln Arg Asp Val Asp Asp Leu Tyr Gly Ala Val Met Ala His Trp
 50                  55                  60

Gln Thr Ala Gln Lys Phe Thr Pro Gly Asn Ala Arg Ile Arg Val Tyr
 65                  70                  75                  80

Asn Pro Asn Leu Glu Glu His Gly Trp His Ser Asp His Thr Val Val
                 85                  90                  95

Glu Ile Val Asn Asp Asp Met Pro Phe Leu Val Asp Ser Val Thr Met
                100                 105                 110

Glu Ile Asn Arg Gln Gly Leu Ala Leu His Ser Ala Ile His Pro Val
                115                 120                 125

Phe Arg Val Trp Arg Asp Ala Arg Gly Gly Ile Glu Arg Ile Ala Pro
130                 135                 140

Gly Gly Ala Gly Glu Ala Gly Asp Ser Ser Arg Leu Glu Ser Phe Ile
145                 150                 155                 160

His Phe Glu Ile Asp Arg Ser Gly Glu Ala Ala Arg Leu Glu Ala Leu
                165                 170                 175

Arg Ser Gly Ile Ala Gln Val Leu Val Asp Val Arg Ala Ala Val Glu
                180                 185                 190

Asp Trp Ser Lys Met Cys Gly Ile Thr Gln Ala Thr Ile Ala Ala Met
                195                 200                 205

Ala Gln Ala Pro Asp Ala Ala Ala Pro Glu Ser Val Glu Ala Arg Ala
210                 215                 220

Phe Leu Asp Trp Met Met Asp Asp His Phe Ser Phe Leu Gly Gln Arg
225                 230                 235                 240

Asp Tyr Gln Leu Val Ser Gln Asp Gly Arg Tyr Phe Leu Arg Gly Val
                245                 250                 255

Pro Gly Ser Gly Ala Gly Ile Leu Arg Glu Ser Leu Arg Glu Pro Asp
                260                 265                 270

Ala Glu Asp Leu Thr Leu Leu Pro Ala Ala Thr Ala Ile Ile Glu
                275                 280                 285

Gly Ala Ser Pro Ile Phe Leu Thr Lys Ala Asn Ser Arg Ala Thr Val
290                 295                 300

His Arg Pro Gly Tyr Leu Asp Tyr Val Gly Val Lys Leu Leu Asp Glu
305                 310                 315                 320

Lys Gly Gln Leu Phe Gly Glu Arg Arg Phe Val Gly Leu Tyr Thr Ser
                325                 330                 335

Thr Ala Tyr Thr Ala Pro Ile Ala Glu Ile Pro Leu Val Arg Leu Lys
                340                 345                 350

Cys Ala Asn Ile Leu Ala Arg Ala Gly Phe Leu Ala Lys Gly His Leu
                355                 360                 365

Tyr Lys Ser Leu Val Thr Ile Leu Glu Gln Tyr Pro Arg Asp Glu Leu
370                 375                 380

Phe Gln Ala Thr Glu Asp Glu Leu Phe Asp Ile Thr Thr Gly Ile Leu
385                 390                 395                 400

Arg Leu Gln Glu His Gln Arg Thr Arg Leu Phe Val Arg Arg Asp Arg
                405                 410                 415

Phe Asp Arg Phe Val Ser Cys Leu Val Phe Val Pro Arg Asp Lys Tyr
                420                 425                 430

Asn Thr Asp Leu Arg Gln Lys Ile Gln Arg Leu Leu Thr Ala Ala Phe
                435                 440                 445
```

-continued

```
His Gly Thr Ser Cys Glu Phe Thr Pro Leu Leu Ser Glu Ser Pro Leu
    450                 455                 460

Ala Arg Ile Gln Leu Thr Val Arg Gly Glu Pro Gly Thr Met Pro His
465                 470                 475                 480

Val Asp Thr Arg Glu Leu Glu Ala Arg Ile Val His Ala Ser Arg Arg
                485                 490                 495

Trp Gln Asp Asp Leu Ala Glu Ala Leu His Glu Ser His Gly Glu Glu
            500                 505                 510

Gln Gly Asn Arg Leu Leu Gln Arg Tyr Gly Gly Ser Phe Pro Ala Gly
        515                 520                 525

Tyr Arg Glu Asp Tyr Pro Ala Arg Thr Ala Val Arg Asp Ile Glu Leu
530                 535                 540

Met Glu His Ala Leu Arg Gly Asn Gly Met Ala Met Asn Leu Tyr Arg
545                 550                 555                 560

Pro Ile Glu Ala Ala Pro Gly Val Phe Arg Phe Lys Val Tyr Arg Ala
                565                 570                 575

Gly Glu Pro Ile Ala Leu Ser His Ser Leu Pro Met Leu Glu His Leu
            580                 585                 590

Gly Val Arg Val Asp Glu Glu Arg Pro Tyr Leu Ile Glu Pro Asp Ser
        595                 600                 605

Gly Ala Pro Val Trp Val His Asp Phe Gly Leu Glu Ile Ala Asp Ser
        610                 615                 620

Gly Gly Ala Ala Glu Phe Asp Ile Ala Arg Val Lys Ala Leu Phe Glu
625                 630                 635                 640

Asp Ala Phe Ala Arg Ala Trp His Gly Glu Ile Glu Asn Asp Asp Phe
                645                 650                 655

Asn Arg Leu Val Leu Arg Ala Glu Leu Ala Ala Arg Asp Val Thr Ile
            660                 665                 670

Leu Arg Ala Tyr Ala Arg Tyr Leu Arg Gln Val Gly Ser Thr Phe Ser
        675                 680                 685

Asp Ala Tyr Ile Glu Arg Ala Leu Thr Gly Asn Ala Ala Ile Ala Ala
        690                 695                 700

Met Leu Val Gly Leu Phe Val Ala Arg Phe Asp Thr Phe Ser Glu Val
705                 710                 715                 720

Ala Thr Asp Thr Ala Arg Gln Ala Arg Cys Asp Lys Leu Leu Ala Asp
                725                 730                 735

Ile Gly Ala Ala Leu Asp Lys Val Pro Asn Leu Asp Glu Asp Arg Ile
            740                 745                 750

Leu Arg Leu Phe Leu Gly Val Ile Asn Ala Thr Val Arg Thr Asn Tyr
        755                 760                 765

Phe His Arg Gly Glu Glu Gly Gln Pro Arg Pro Tyr Val Ser Phe Lys
    770                 775                 780

Phe Asn Pro Ala Leu Val Pro Gly Leu Pro Glu Pro Arg Pro Met Phe
785                 790                 795                 800

Glu Ile Trp Val Tyr Ser Pro Arg Val Glu Gly Val His Leu Arg Gly
                805                 810                 815

Gly Arg Val Ala Arg Gly Gly Leu Arg Trp Ser Asp Arg Arg Glu Asp
            820                 825                 830

Phe Arg Thr Glu Val Leu Gly Leu Met Lys Ala Gln Met Val Lys Asn
        835                 840                 845

Thr Val Ile Val Pro Val Gly Ser Lys Gly Gly Phe Val Val Lys Arg
    850                 855                 860

Pro Pro Pro Pro Thr Asp Arg Asp Ala Phe Leu Gln Glu Gly Ile Ala
```

-continued

```
865                 870                 875                 880
Cys Tyr Gln Thr Phe Leu Arg Gly Leu Leu Asp Leu Thr Asp Asn Leu
                885                 890                 895

Val Gly Gly Gln Leu Val Pro Pro Glu Val Val Arg His Asp Asp
            900                 905                 910

Asn Asp Pro Tyr Leu Val Val Ala Ala Asp Lys Gly Thr Ala Thr Phe
            915                 920                 925

Ser Asp Phe Ala Asn Ala Ile Ser Ala Glu Tyr Gly Phe Trp Leu Gly
    930                 935                 940

Asp Ala Phe Ala Ser Gly Gly Ser Val Gly Tyr Asp His Lys Lys Met
945                 950                 955                 960

Gly Ile Thr Ala Arg Gly Ala Trp Glu Ser Val Lys Arg His Phe Arg
                965                 970                 975

Glu Met Gly Val Asp Ile Gln Thr Thr Asp Phe Thr Val Ala Gly Ile
            980                 985                 990

Gly Asp Met Ser Gly Asp Val Phe  Gly Asn Gly Met Leu  Leu Ser Pro
            995                 1000                1005

His Ile  Arg Leu Val Ala Ala  Phe Asp His Arg His  Ile Phe Leu
        1010                1015                1020

Asp Pro  Asp Pro Asp Thr Thr  Arg Ser Leu Gln Glu  Arg Thr Arg
        1025                1030                1035

Leu Phe  Gly Leu Pro Arg Ser  Ser Trp Ala Asp Tyr  Asp Ala Thr
        1040                1045                1050

Leu Ile  Ser Ala Gly Gly Gly  Ile Tyr Pro Arg Ser  Ala Lys Thr
        1055                1060                1065

Ile Ala  Leu Ser Pro Gln Val  Gln Ala Val Leu Gly  Val Thr Ala
        1070                1075                1080

Ala Thr  Leu Ser Pro Ala Glu  Leu Ile His Ala Ile  Leu Met Ala
        1085                1090                1095

Pro Val  Asp Leu Leu Tyr Asn  Gly Gly Ile Gly Thr  Tyr Val Lys
        1100                1105                1110

Ser Ser  Gln Glu Thr His Leu  Gln Ala Gly Asp Arg  Thr Asn Asp
        1115                1120                1125

Ala Val  Arg Val Asn Gly Asn  Asp Leu Arg Cys Lys  Val Val Gly
        1130                1135                1140

Glu Gly  Gly Asn Leu Gly Phe  Thr Gln Leu Gly Arg  Ile Glu Phe
        1145                1150                1155

Ala Arg  Lys Gly Gly Arg Ile  Asn Thr Asp Ala Ile  Asp Asn Ser
        1160                1165                1170

Ala Gly  Val Asp Cys Ser Asp  His Glu Val Asn Ile  Lys Ile Leu
        1175                1180                1185

Leu Gly  Leu Val Val Ala Asp  Gly Glu Met Thr Glu  Lys Gln Arg
        1190                1195                1200

Asn Lys  Leu Leu Ala Glu Met  Thr Asp Glu Val Gly  Leu Leu Val
        1205                1210                1215

Leu Gln  Asp Asn Tyr Tyr Gln  Thr Gln Ala Leu Ser  Val Ala Gly
        1220                1225                1230

Arg Ser  Ser Pro Ala Leu Leu  Asp Gly Glu Ala Arg  Leu Val Arg
        1235                1240                1245

Trp Leu  Glu Arg Ala Gly Arg  Leu Asn Arg Pro Leu  Glu Phe Leu
        1250                1255                1260

Pro Ser  Glu Glu Glu Ile Ala  Glu Arg Lys Leu Ala  Asp Glu Gly
        1265                1270                1275
```

```
Leu Ala Ser Pro Glu Arg Ala Val Leu Leu Ala Tyr Ser Lys Met
    1280            1285                1290

Trp Leu Tyr Asp Glu Leu Leu Ala Ser Asp Val Pro Glu Asp Thr
    1295            1300                1305

Leu Val Ala Gly Leu Leu Ser Asp Tyr Phe Pro Val Pro Leu Arg
    1310            1315                1320

Gln Arg Tyr Ala Asp Ala Met Gln Arg His Pro Leu Arg Arg Glu
    1325            1330                1335

Ile Leu Ser Thr His Leu Thr Asn Met Leu Val Asn Arg Ile Gly
    1340            1345                1350

Ala Thr Phe Val His Arg Ile Met Glu Glu Thr Asp Ala Arg Pro
    1355            1360                1365

Ala Asp Ile Val Arg Ala Cys Leu Ile Ala Arg Asp Val Phe Gly
    1370            1375                1380

Leu Thr Thr Leu Trp Gln Glu Ile Asp Ala Leu Asp Asn Arg Val
    1385            1390                1395

Ala Asp Ala Glu Gln Ala Arg Met Phe Gly Ala Val Ala Leu Leu
    1400            1405                1410

Leu Glu Arg Ala Cys Leu Trp Phe Ile Arg Tyr Leu Arg Ser Gly
    1415            1420                1425

Ser Lys Ala Ala Glu Asp Leu Ala Arg Phe Ala Gln Ala Ala Gln
    1430            1435                1440

Trp Leu Ala Pro Gln Leu Pro Arg Leu Pro Pro Ala Asp Ala
    1445            1450                1455

Thr Ala Leu Ser Glu Arg Ala Arg Ala Leu Thr Asp Ala Gly Val
    1460            1465                1470

Asp Glu Ala Leu Ala Val Arg Val Ala Gly Ser Glu Ile Ser Ala
    1475            1480                1485

Ala Ala Leu Asp Ile Ala Glu Val Ala Thr Ala Cys Lys Arg Ser
    1490            1495                1500

Leu Asp Leu Val Ala Gly Val Tyr Phe Ala Leu Asp Ser His Leu
    1505            1510                1515

Ser Phe Ser Trp Leu Arg Glu Arg Ala Leu Ala Leu Pro Ser Asp
    1520            1525                1530

Thr His Trp Asp Leu Leu Ala Arg Thr Thr Thr Leu Glu Asp Leu
    1535            1540                1545

Gly Arg Leu Lys Arg Ala Leu Thr Val Ser Val Leu Ser Gln Glu
    1550            1555                1560

Gly Glu Leu Asp Thr Pro Asp Ala Met Ile Asp Ala Trp Arg Ser
    1565            1570                1575

Ser Arg His Gly Ala Leu Glu Arg Phe Thr Arg Met Leu Ala Asp
    1580            1585                1590

Gln Arg Ala Ser Gly Ala Ala Gly Leu Ser Met Leu Ser Val Ala
    1595            1600                1605

Val Arg Glu Ile Gly Met Leu Glu Arg Ala
    1610            1615
```

<210> SEQ ID NO 33
<211> LENGTH: 633
<212> TYPE: DNA
<213> ORGANISM: C. necator

<400> SEQUENCE: 33
atgaccgcaa cgccaaaccc cacgccccac cgcggcgaga ccgtgttcat cgtcgacgac    60

```
gatgaagcca tgcgcgactc gctgacctgg ctgctggagg gcaatggcta ccaggtgcgc      120
agcttcacca cgcgccgagca gttcctcgcc gcctacgatg ccagccaggt gtcgtgcctg     180
atcctcgacg tgcgcatgcc cggcatgagc ggcccggaac tgcaggagcg catgctggcc     240
gagcagatcg acattcccat cgtctttatc accggccacg gcgacgtgcc gatggcggta     300
tcgacgatga agcgcggcgc catcgacttc atcgaaaagc ccttcgatga gtccgagctg     360
cgcgcactgg tcgagcgcat gctgaccaag gcccgcaccg accattccgc cgcacgcgag     420
cagcgcgccg ccaaggacct gctgggcaag ctgaccacgc gcgagcagca ggtgctcgag     480
cgcatcgttg ccggccgcct gaacaagcag atcgccgacg acctgggcat ttccatcaag     540
accgtggagg cgcaccgcgc caacatcatg gaaaagctca acgtcaacac cgtcgccgac     600
ctgctgcgcc tggcgctgtc acgcaacagc tga                                  633
```

<210> SEQ ID NO 34
<211> LENGTH: 210
<212> TYPE: PRT
<213> ORGANISM: C. necator

<400> SEQUENCE: 34

```
Met Thr Ala Thr Pro Asn Pro Thr Pro His Arg Gly Glu Thr Val Phe
1               5                   10                  15

Ile Val Asp Asp Glu Ala Met Arg Asp Ser Leu Thr Trp Leu Leu
            20                  25                  30

Glu Gly Asn Gly Tyr Gln Val Arg Ser Phe Thr Ser Ala Glu Gln Phe
        35                  40                  45

Leu Ala Ala Tyr Asp Ala Ser Gln Val Ser Cys Leu Ile Leu Asp Val
    50                  55                  60

Arg Met Pro Gly Met Ser Gly Pro Glu Leu Gln Glu Arg Met Leu Ala
65                  70                  75                  80

Glu Gln Ile Asp Ile Pro Ile Val Phe Ile Thr Gly His Gly Asp Val
                85                  90                  95

Pro Met Ala Val Ser Thr Met Lys Arg Gly Ala Ile Asp Phe Ile Glu
            100                 105                 110

Lys Pro Phe Asp Glu Ser Glu Leu Arg Ala Leu Val Glu Arg Met Leu
        115                 120                 125

Thr Lys Ala Arg Thr Asp His Ser Ala Ala Arg Glu Gln Arg Ala Ala
    130                 135                 140

Lys Asp Leu Leu Gly Lys Leu Thr Thr Arg Glu Gln Gln Val Leu Glu
145                 150                 155                 160

Arg Ile Val Ala Gly Arg Leu Asn Lys Gln Ile Ala Asp Asp Leu Gly
                165                 170                 175

Ile Ser Ile Lys Thr Val Glu Ala His Arg Ala Asn Ile Met Glu Lys
            180                 185                 190

Leu Asn Val Asn Thr Val Ala Asp Leu Leu Arg Leu Ala Leu Ser Arg
        195                 200                 205

Asn Ser
    210
```

<210> SEQ ID NO 35
<211> LENGTH: 2586
<212> TYPE: DNA
<213> ORGANISM: C. necator

<400> SEQUENCE: 35

-continued

| | |
|---|---|
| atgccgtttt tcgaccgact cctttccagc ctgcgtgcag ccatgcttcc tcccgacgcg | 60 |
| tcggggtcag ccaaggcggc cggaggcgat cccgcgcacg cccttcgcc ggctgccgga | 120 |
| ctggggccga tcgaggcgct gggccccgac gacggcgccc ccgtggccgc accgcgcggg | 180 |
| ctgtggtggc tgcgctggcg caacctggtg gccaccagct ggttcatgtt catcccgctg | 240 |
| gttgccatcg tgctgttcac ggtggccatg ggcgtgatcc tgtggtccct gcacgagacc | 300 |
| gagcgccagc agcagcgcga cgccctgtac cgcgacgccg cctgggcgca gcagcgcgtg | 360 |
| cgcctgtccc tgctgagcaa ccaggaccag ctggcctcgc tggcgcgcga catcgccgcc | 420 |
| gcgcagcttg agcaaggcgc ctaccgcacc gcggcgcagg aaatcctgcg cgaaaacccc | 480 |
| gagatcgttt tcatcaactg gctcgatgcc accaagcgcg gccgctggtc gttgccatcg | 540 |
| acctcggaat cgccagccg cctgcgcgag aaccaggacc agccgctcga accggaagtg | 600 |
| ctcgacacct tcgacgccgc gcgcgagacc cagcgagtgg tctattcgcg cccgctggtc | 660 |
| aacgagcgcg cgacagctt catgctgatg aagtgccga tcgtgcgcga caacgagttc | 720 |
| ctcggcacgc tcggcgcgct gtactcgatc aacggcatcc tgacgcacct gctgccgcct | 780 |
| gagctgaccg agcgctaccg cttctcgctg atcgacaaga caaccagac ccgcgccagc | 840 |
| acctcgttgc ggccggtgcc gggcaacgcg ctgtcgtacg aggtgctgct ggatccgccg | 900 |
| ggtcactccc tgtcgctgcg cgccgatgcc tacccgccgg cgtcgaacct gcccaacaac | 960 |
| atgctgctgt ggctggtggt ggggctgtcg tgcttcctgc tgtggagcct gtggagcatg | 1020 |
| tggcgccaca ccagccgccg ctccgaggcg cagcgcgcgc tgctggccga gacctcgttc | 1080 |
| cggcgcgcga tggaaaactc gatgctgatc ggcctgcgcg cgctcgacct gaacggccgc | 1140 |
| atcacctatg tcaacccggc cttctgccgc atgactggct ggcaggagaa cgacctggtc | 1200 |
| gggcgcctgc cgcccttccc ctactggccg cccaacgacc agcaggagat gcagaagcag | 1260 |
| atcgacctga cgctgcaggg caagtcgccc gccggcggct acgagatgcg cgtgatgcgc | 1320 |
| cgcgacggca gcagcttcta cgcgcgcatg tacgtgtcgc cgctggtgga cagccgcggc | 1380 |
| cgccatactg gctggatgag ctcgatgacg gacatcaccg agcccaagcg cgcgcgcgag | 1440 |
| gaactggccg cggcgcatga ccgcttcacc acggtgctgg aaagcctgga tgccgcggtg | 1500 |
| tcggtgctgg ccaccgacaa ggcggagctg ctctttgcca accgctatta ccgccagctg | 1560 |
| ttcggctggg aggccagggg ccacctcaag ctggccggcg acgacctcga caaggaccag | 1620 |
| gtctccagcg acaacaccga ctatgtcgac gcctatgccg gctgccggc gtccgagctg | 1680 |
| atgccgtacg catcggacgc gcgcgaagtg ttcgtgccgg acatgcagaa atggttcgaa | 1740 |
| gtgcgccgcc gctatatcca gtgggtcgac ggccacctgg cgcagatgca gatcgccacc | 1800 |
| gatatcacgt gcgcaaggc cgccgaggaa atggcgcgcc agcatgaaga gcgcctgcag | 1860 |
| ttcaccagcc gcctgaccac catgggcgag atggcctcgt cgctggcgca tgaactgaac | 1920 |
| cagccgctgg cggccatcaa caactactgc atgggcgcgg tggcgcggct gcactcgggc | 1980 |
| cgcagcacgc cggaggacct gatcccggtg ctggagaaga cctcggccca ggcggtcgcg | 2040 |
| gccggcacca tcatcagccg catccgcggc ttcgtgaagc gcagccagcc gcagcggcgc | 2100 |
| gaggccgcgc tgcacgacat cgtcgccgac gcggtaggcc tggccgacct ggaggccacg | 2160 |
| cgccgccgcg tcaccatcct gacccgcctg ccgaccccgc cgctgacggt ctatgtcgac | 2220 |
| ccggtgctga tcgagcaggt gctggtgaac ctgctcaaga acgcggtcga ggccatggcc | 2280 |
| ggcctgcccg cctgcacgc cggcggcgtg gtgcgcctgc acgcgcgggt ggagccgggc | 2340 |
| gagattggcg acagcgtcca tatcgacgtg atcgaccagg gcccgggcgt ggacgaagcc | 2400 |

```
accaaggagc gcctgttcga gcccttcttc agcaccaagt ccgacggcat gggcatgggg    2460
ctgaacatct gccgctcgat catcgagtcg caccagggcc gcctgtgggt ggagaacaat    2520
gccgacggca tcggctgtac atttaaaatc atgctgccgc tgcaatcggc gctggccgag    2580
cattaa                                                                2586
```

<210> SEQ ID NO 36
<211> LENGTH: 861
<212> TYPE: PRT
<213> ORGANISM: C. necator

<400> SEQUENCE: 36

```
Met Pro Phe Phe Asp Arg Leu Leu Ser Ser Leu Arg Ala Ala Met Leu
1               5                   10                  15

Pro Pro Asp Ala Ser Gly Ser Ala Lys Ala Ala Gly Gly Asp Pro Ala
            20                  25                  30

His Ala Pro Ser Pro Ala Ala Gly Leu Gly Pro Ile Glu Ala Leu Gly
        35                  40                  45

Pro Asp Asp Gly Ala Pro Val Ala Ala Pro Arg Gly Leu Trp Trp Leu
    50                  55                  60

Arg Trp Arg Asn Leu Val Ala Thr Ser Trp Phe Met Phe Ile Pro Leu
65                  70                  75                  80

Val Ala Ile Val Leu Phe Thr Val Ala Met Gly Val Ile Leu Trp Ser
                85                  90                  95

Leu His Glu Thr Glu Arg Gln Gln Gln Arg Asp Ala Leu Tyr Arg Asp
            100                 105                 110

Ala Ala Trp Ala Gln Gln Arg Val Arg Leu Ser Leu Leu Ser Asn Gln
        115                 120                 125

Asp Gln Leu Ala Ser Leu Ala Arg Asp Ile Ala Ala Gln Leu Glu
    130                 135                 140

Gln Gly Ala Tyr Arg Thr Ala Ala Gln Glu Ile Leu Arg Glu Asn Pro
145                 150                 155                 160

Glu Ile Val Phe Ile Asn Trp Leu Asp Ala Thr Lys Arg Gly Arg Trp
                165                 170                 175

Ser Leu Pro Ser Thr Ser Glu Phe Ala Ser Arg Leu Arg Glu Asn Gln
            180                 185                 190

Asp Gln Pro Leu Glu Pro Glu Val Leu Asp Thr Phe Asp Ala Ala Arg
        195                 200                 205

Glu Thr Gln Arg Val Val Tyr Ser Arg Pro Leu Val Asn Glu Arg Gly
    210                 215                 220

Asp Ser Phe Met Leu Met Glu Val Pro Ile Val Arg Asp Asn Glu Phe
225                 230                 235                 240

Leu Gly Thr Leu Gly Ala Leu Tyr Ser Ile Asn Gly Ile Leu Thr His
                245                 250                 255

Leu Leu Pro Pro Glu Leu Thr Glu Arg Tyr Arg Phe Ser Leu Ile Asp
            260                 265                 270

Lys Asn Asn Gln Thr Arg Ala Ser Thr Ser Leu Arg Pro Val Pro Gly
        275                 280                 285

Asn Ala Leu Ser Tyr Glu Val Leu Leu Asp Pro Gly His Ser Leu
    290                 295                 300

Ser Leu Arg Ala Asp Ala Tyr Pro Pro Ala Ser Asn Leu Pro Asn Asn
305                 310                 315                 320

Met Leu Leu Trp Leu Val Val Gly Leu Ser Cys Phe Leu Leu Trp Ser
                325                 330                 335
```

-continued

Leu Trp Ser Met Trp Arg His Thr Ser Arg Arg Ser Glu Ala Gln Arg
            340                 345                 350

Ala Leu Leu Ala Glu Thr Ser Phe Arg Arg Ala Met Glu Asn Ser Met
            355                 360                 365

Leu Ile Gly Leu Arg Ala Leu Asp Leu Asn Gly Arg Ile Thr Tyr Val
            370                 375                 380

Asn Pro Ala Phe Cys Arg Met Thr Gly Trp Gln Glu Asn Asp Leu Val
385                 390                 395                 400

Gly Arg Leu Pro Pro Phe Pro Tyr Trp Pro Asn Asp Gln Gln Glu
                    405                 410                 415

Met Gln Lys Gln Ile Asp Leu Thr Leu Gln Gly Lys Ser Pro Ala Gly
            420                 425                 430

Gly Tyr Glu Met Arg Val Met Arg Arg Asp Gly Ser Ser Phe Tyr Ala
            435                 440                 445

Arg Met Tyr Val Ser Pro Leu Val Asp Ser Arg Gly Arg His Thr Gly
            450                 455                 460

Trp Met Ser Ser Met Thr Asp Ile Thr Glu Pro Lys Arg Ala Arg Glu
465                 470                 475                 480

Glu Leu Ala Ala Ala His Asp Arg Phe Thr Thr Val Leu Glu Ser Leu
                    485                 490                 495

Asp Ala Ala Val Ser Val Leu Ala Thr Asp Lys Ala Glu Leu Leu Phe
                500                 505                 510

Ala Asn Arg Tyr Tyr Arg Gln Leu Phe Gly Trp Glu Ala Glu Gly His
            515                 520                 525

Leu Lys Leu Ala Gly Asp Asp Leu Asp Lys Asp Gln Val Ser Ser Asp
            530                 535                 540

Asn Thr Asp Tyr Val Asp Ala Tyr Ala Gly Leu Pro Ala Ser Glu Leu
545                 550                 555                 560

Met Pro Tyr Ala Ser Asp Ala Arg Glu Val Phe Val Pro Asp Met Gln
                    565                 570                 575

Lys Trp Phe Glu Val Arg Arg Arg Tyr Ile Gln Trp Val Asp Gly His
            580                 585                 590

Leu Ala Gln Met Gln Ile Ala Thr Asp Ile Thr Val Arg Lys Ala Ala
            595                 600                 605

Glu Glu Met Ala Arg Gln His Glu Glu Arg Leu Gln Phe Thr Ser Arg
            610                 615                 620

Leu Thr Thr Met Gly Glu Met Ala Ser Ser Leu Ala His Glu Leu Asn
625                 630                 635                 640

Gln Pro Leu Ala Ala Ile Asn Asn Tyr Cys Met Gly Ala Val Ala Arg
                    645                 650                 655

Leu His Ser Gly Arg Ser Thr Pro Glu Asp Leu Ile Pro Val Leu Glu
                    660                 665                 670

Lys Thr Ser Ala Gln Ala Val Arg Ala Gly Thr Ile Ile Ser Arg Ile
            675                 680                 685

Arg Gly Phe Val Lys Arg Ser Gln Pro Gln Arg Arg Glu Ala Ala Leu
            690                 695                 700

His Asp Ile Val Ala Asp Ala Val Gly Leu Ala Asp Leu Glu Ala Thr
705                 710                 715                 720

Arg Arg Arg Val Thr Ile Leu Thr Arg Leu Pro Thr Pro Leu Thr
                    725                 730                 735

Val Tyr Val Asp Pro Val Leu Ile Glu Gln Val Leu Val Asn Leu Leu
            740                 745                 750

| Lys | Asn | Ala | Val | Glu | Ala | Met | Ala | Gly | Leu | Pro | Ala | Leu | His | Ala | Gly |
|---|---|---|---|---|---|---|---|---|---|---|---|---|---|---|---|
| | | | 755 | | | | 760 | | | | 765 | | | | |

| Gly | Val | Val | Arg | Leu | His | Ala | Arg | Val | Glu | Pro | Gly | Glu | Ile | Gly | Asp |
|---|---|---|---|---|---|---|---|---|---|---|---|---|---|---|---|
| | 770 | | | | 775 | | | | 780 | | | | | | |

| Ser | Val | His | Ile | Asp | Val | Ile | Asp | Gln | Gly | Pro | Gly | Val | Asp | Glu | Ala |
|---|---|---|---|---|---|---|---|---|---|---|---|---|---|---|---|
| 785 | | | | | 790 | | | | 795 | | | | | | 800 |

| Thr | Lys | Glu | Arg | Leu | Phe | Glu | Pro | Phe | Phe | Ser | Thr | Lys | Ser | Asp | Gly |
|---|---|---|---|---|---|---|---|---|---|---|---|---|---|---|---|
| | | | | 805 | | | | 810 | | | | | 815 | | |

| Met | Gly | Met | Gly | Leu | Asn | Ile | Cys | Arg | Ser | Ile | Ile | Glu | Ser | His | Gln |
|---|---|---|---|---|---|---|---|---|---|---|---|---|---|---|---|
| | | | 820 | | | | 825 | | | | | 830 | | | |

| Gly | Arg | Leu | Trp | Val | Glu | Asn | Asn | Ala | Asp | Gly | Ile | Gly | Cys | Thr | Phe |
|---|---|---|---|---|---|---|---|---|---|---|---|---|---|---|---|
| | | 835 | | | | 840 | | | | 845 | | | | | |

| Lys | Ile | Met | Leu | Pro | Leu | Gln | Ser | Ala | Leu | Ala | Glu | His |
|---|---|---|---|---|---|---|---|---|---|---|---|---|
| 850 | | | | | 855 | | | | 860 | | | |

<210> SEQ ID NO 37
<211> LENGTH: 2583
<212> TYPE: DNA
<213> ORGANISM: C. necator

<400> SEQUENCE: 37

```
atggacacca cgccggaact gctgcttgcc gcgcgcgtgc gcgaccagct caaagccgac      60
aagcaggcac tgtttgccga cttcaacatc agcgccaatg tcggcacgct gatcacgcgg     120
ctgcgccgcg ccgtcgacgc cgggctggtg aagcctggcg cggcctgggg gatgcccgcg     180
ggcgcggcgc tggtggcggt gggcggctat ggccgcggcg agctgctgcc ttactccgac     240
gtcgacgtgc tgctgttgct gcccgccgag ccagaccagg acaccaccgg cgcctggag      300
cgctttatcg gcctgtgctg ggacctcggg ctggagatcg gctcttcggt gcgcaccgtg     360
gacgattgca tccgcgagtc gcgccaggac gtcaccatcc agacctcgct gctggaagcg     420
cggctgctga ccggcagccg caagctgttc gagtcgatgc gtacgcgcta cctcgccgac     480
ctggacccgg ccgcgttctt ccaggccaag ctgctggaaa tgcgccagcg ccacgccaag     540
taccaggaca cgccctactc gctcgagccc aactgcaagg aaagccccgg cggcctgcgc     600
gatctgcagg tgatcctgtg gatgaccaag gcggcgggcc tgggcgacag ctggaaagaa     660
ctttcgagc gcggcctgct gacgcagcgc gaagcgcagg agctcgcgcg caacgagcgc     720
ctgctcaaga ccatccgcgc gcgcctgcac ctggtggccg gccggcgcca ggacgtgctg     780
gtattcgacc tgcagaccgc gctggcggag tccttcggct atcgccagac caccagcaag     840
cgcgccagcg aacaactgat gccgctac tactgggcgg ccaaggcagt cacgcagctc     900
aacagcgtgc tgctgctgaa catcgaggcg atgctgttcc gagcgagtc tcaggtgacg     960
cgcgtgctca cgagcgctt tgtcgagcgc cagggcatgc tggaaatcac cagcgacgac    1020
atctatgaac gcgacccgca cgcgatcctg aaaccttcc tgctgtacca gcgcacgccc    1080
ggcgtgaaag gctgtcgcc gcgcacgctg gcgggctgt acaacgcgcg caccgtgatg    1140
aatgcgggct ggcgcaacga tccggaaaac cgccgcctgt cctggccat catgcaggag    1200
ccgcagggca tcacccacgc gctgcgcctg atgaaccaga ccagcgtgct gggccgctac    1260
ctgatcaact tccggcgcat cgtcggccag atgcagcacg acctgttcca cgtctacacc    1320
gtggaccagc acatcctgat ggtggtgcgc aacatgcgcc gcttcgccat cgtcgagcac    1380
acccacgagt tcccgttctg cagccagctg atggccagct cgacaagcc gtgggtgctg    1440
tgggtggcag cgctgttcca cgacatcgcc aagggccgcg gcggcgacca ctcgaagctt    1500
```

-continued

```
ggcaccgtgg atgcgcgccg cttctgcaag cagcacggca ttgcgcgcga agacgccgac    1560
ctggtctgct ggctggtcga gcaccacctg accatgagcc acgtggcgca gaagcaggac    1620
ctgaccgatc ccgatgtgat ccacgccttt gcccgcgtgg tcggcagcga acgctacctg    1680
accgcgctct acctgctgac cgtggccgac atccgcggca ccagtcccaa ggtatggaac    1740
gcgtggaagg gcaagctgct ggaagacctg taccacatca cgctgcgcgt gctcggcggc    1800
gcgcgcgtgg attcgcattc gctgtggtcg cagcgcaagg aagacaccat ctccgagctg    1860
cgcctgaagg ccttcgaccc ggcgctgggc aagtccctgt gggcgcagct cgacgtggct    1920
ttcttcctgc gccacgattc gcacgatatc gcctggctca cgcgccacct gtacaacaag    1980
gtggacagcc ccacgccggt ggtcaaggca cgcgtctccc ccgccggcga aggcctgcag    2040
gtggcggtct acgtcaagga ccagcccgac ctgttcgcgc gcatctgcgg ctacttcgag    2100
cgcaaggcat tctcgatcca ggacgccaag atccacacca cgcgccacgg ctacgcgctg    2160
gacacgttcc aggtcaccga ccccggcatg gccggcgacg cggcagcta ccgcgacatc    2220 atcgcgctgg tcgagcacga actgtgcgag cggctgcgcc tgcaaggcgc actgcccgaa    2280
cccacgcagg ggcggctgtc gcgccagtcg cgcagcttcc cgatcaagcc gcgcgtggac    2340
ctgcgccccg acgagcgcgg ccagtattac ctgctgtcgc tgtccgccaa cgaccgcacc    2400
ggcctgctgt acgccatcgc ccgcgtactg gcacggcatc gcgtatccgt ccacacggca    2460
cgcatcaaca ccctgggcga acgcgtcgaa gacgtgttcc tggtcgacgg cagccgcctg    2520
gctgccgaca accgattgca gattcagctt gaacaggact tgctcgccgc cctcgccatc    2580
tga                                                                  2583
```

<210> SEQ ID NO 38
<211> LENGTH: 860
<212> TYPE: PRT
<213> ORGANISM: C. necator

<400> SEQUENCE: 38

```
Met Asp Thr Thr Pro Glu Leu Leu Leu Ala Ala Arg Val Arg Asp Gln
1               5                   10                  15

Leu Lys Ala Asp Lys Gln Ala Leu Phe Ala Asp Phe Asn Ile Ser Ala
            20                  25                  30

Asn Val Gly Thr Leu Ile Thr Arg Leu Arg Arg Ala Val Asp Ala Gly
        35                  40                  45

Leu Val Glu Ala Trp Arg Gly Leu Gly Met Pro Ala Gly Ala Ala Leu
    50                  55                  60

Val Ala Val Gly Gly Tyr Gly Arg Gly Glu Leu Leu Pro Tyr Ser Asp
65                  70                  75                  80

Val Asp Val Leu Leu Leu Pro Ala Glu Pro Asp Gln Asp Thr Thr
                85                  90                  95

Gly Arg Leu Glu Arg Phe Ile Gly Leu Cys Trp Asp Leu Gly Leu Glu
            100                 105                 110

Ile Gly Ser Ser Val Arg Thr Val Asp Asp Cys Ile Arg Glu Ser Arg
        115                 120                 125

Gln Asp Val Thr Ile Gln Thr Ser Leu Leu Glu Ala Arg Leu Leu Thr
    130                 135                 140

Gly Ser Arg Lys Leu Phe Glu Ser Met Arg Thr Arg Tyr Leu Ala Asp
145                 150                 155                 160

Leu Asp Pro Ala Ala Phe Phe Gln Ala Lys Leu Leu Glu Met Arg Gln
                165                 170                 175
```

-continued

Arg His Ala Lys Tyr Gln Asp Thr Pro Tyr Ser Leu Glu Pro Asn Cys
            180                 185                 190

Lys Glu Ser Pro Gly Gly Leu Arg Asp Leu Gln Val Ile Leu Trp Met
        195                 200                 205

Thr Lys Ala Ala Gly Leu Gly Asp Ser Trp Lys Glu Leu Phe Glu Arg
        210                 215                 220

Gly Leu Leu Thr Gln Arg Glu Ala Gln Glu Leu Ala Arg Asn Glu Arg
225                 230                 235                 240

Leu Leu Lys Thr Ile Arg Ala Arg Leu His Leu Val Ala Gly Arg Arg
                245                 250                 255

Gln Asp Val Leu Val Phe Asp Leu Gln Thr Ala Leu Ala Glu Ser Phe
            260                 265                 270

Gly Tyr Arg Gln Thr Thr Ser Lys Arg Ala Ser Glu Gln Leu Met Arg
        275                 280                 285

Arg Tyr Tyr Trp Ala Ala Lys Ala Val Thr Gln Leu Asn Ser Val Leu
        290                 295                 300

Leu Leu Asn Ile Glu Ala Met Leu Phe Pro Ser Glu Ser Gln Val Thr
305                 310                 315                 320

Arg Val Leu Asn Glu Arg Phe Val Arg Gln Gly Met Leu Glu Ile
                325                 330                 335

Thr Ser Asp Asp Ile Tyr Glu Arg Asp Pro His Ala Ile Leu Glu Thr
                340                 345                 350

Phe Leu Leu Tyr Gln Arg Thr Pro Gly Val Lys Gly Leu Ser Pro Arg
            355                 360                 365

Thr Leu Arg Gly Leu Tyr Asn Ala Arg Thr Val Met Asn Ala Gly Trp
370                 375                 380

Arg Asn Asp Pro Glu Asn Arg Arg Leu Phe Leu Ala Ile Met Gln Glu
385                 390                 395                 400

Pro Gln Gly Ile Thr His Ala Leu Arg Leu Met Asn Gln Thr Ser Val
                405                 410                 415

Leu Gly Arg Tyr Leu Ile Asn Phe Arg Arg Ile Val Gly Gln Met Gln
            420                 425                 430

His Asp Leu Phe His Val Tyr Thr Val Asp Gln His Ile Leu Met Val
        435                 440                 445

Val Arg Asn Met Arg Arg Phe Ala Ile Val Glu His Thr His Glu Phe
450                 455                 460

Pro Phe Cys Ser Gln Leu Met Ala Ser Phe Asp Lys Pro Trp Val Leu
465                 470                 475                 480

Trp Val Ala Ala Leu Phe His Asp Ile Ala Lys Gly Arg Gly Gly Asp
                485                 490                 495

His Ser Lys Leu Gly Thr Val Asp Ala Arg Arg Phe Cys Lys Gln His
            500                 505                 510

Gly Ile Ala Arg Glu Asp Ala Asp Leu Val Cys Trp Leu Val Glu His
        515                 520                 525

His Leu Thr Met Ser His Val Ala Gln Lys Gln Asp Leu Thr Asp Pro
        530                 535                 540

Asp Val Ile His Ala Phe Ala Arg Val Val Gly Ser Glu Arg Tyr Leu
545                 550                 555                 560

Thr Ala Leu Tyr Leu Leu Thr Val Ala Asp Ile Arg Gly Thr Ser Pro
                565                 570                 575

Lys Val Trp Asn Ala Trp Lys Gly Lys Leu Leu Glu Asp Leu Tyr His
            580                 585                 590

Ile Thr Leu Arg Val Leu Gly Gly Ala Arg Val Asp Ser His Ser Leu

```
                                595                     600                     605
        Trp Ser Gln Arg Lys Glu Asp Thr Ile Ser Glu Leu Arg Leu Lys Ala
            610                     615                     620

Phe Asp Pro Ala Leu Gly Lys Ser Leu Trp Ala Gln Leu Asp Val Ala
        625                     630                     635                     640

Phe Phe Leu Arg His Asp Ser His Asp Ile Ala Trp Leu Thr Arg His
                            645                     650                     655

Leu Tyr Asn Lys Val Asp Ser Pro Thr Pro Val Val Lys Ala Arg Val
                        660                     665                     670

Ser Pro Ala Gly Glu Gly Leu Gln Val Ala Val Tyr Val Lys Asp Gln
                    675                     680                     685

Pro Asp Leu Phe Ala Arg Ile Cys Gly Tyr Phe Glu Arg Lys Ala Phe
                690                     695                     700

Ser Ile Gln Asp Ala Lys Ile His Thr Thr Arg His Gly Tyr Ala Leu
        705                     710                     715                     720

Asp Thr Phe Gln Val Thr Asp Pro Gly Met Ala Gly Asp Gly Gly Ser
                            725                     730                     735

Tyr Arg Asp Ile Ile Ala Leu Val Glu His Glu Leu Cys Glu Arg Leu
                        740                     745                     750

Arg Leu Gln Gly Ala Leu Pro Glu Pro Thr Gln Gly Arg Leu Ser Arg
                    755                     760                     765

Gln Ser Arg Ser Phe Pro Ile Lys Pro Arg Val Asp Leu Arg Pro Asp
                770                     775                     780

Glu Arg Gly Gln Tyr Tyr Leu Leu Ser Leu Ser Ala Asn Asp Arg Thr
        785                     790                     795                     800

Gly Leu Leu Tyr Ala Ile Ala Arg Val Leu Ala Arg His Arg Val Ser
                            805                     810                     815

Val His Thr Ala Arg Ile Asn Thr Leu Gly Glu Arg Val Glu Asp Val
                        820                     825                     830

Phe Leu Val Asp Gly Ser Arg Leu Ala Ala Asp Asn Arg Leu Gln Ile
                    835                     840                     845

Gln Leu Glu Gln Asp Leu Leu Ala Ala Leu Ala Ile
                850                     855                     860

<210> SEQ ID NO 39
<211> LENGTH: 1548
<212> TYPE: DNA
<213> ORGANISM: C. necator

<400> SEQUENCE: 39
atgaagccga tctggatagt cgacgacgat caatcaatcc gctgggtcct ggaaaaggcc      60
ctggcccgtg aaagcctgct ctcgcgcagc ttcaccaatg tgcgggatgc gctggccgcg     120
ctggaagaag accagcccca ggtgctgata tcggatatcc gcatgcccgg cggatcgggc     180
ctggacctgc tgcaggccat caaggcgcgg catccgggcc tgccggtcat cgtgatgacg     240
gcctactctg acctggacag cgccgtggcc gcgttccagg gcggtgcctt cgaataccta     300
gccaagccct tcgatgtcga caaggcggtt gagctgatcc gccgcgcgct ggaagaaagc     360
ctgcgcgagg aagaactgga cgaccgcctc gtcgatgcgc ccgagatcct cggccaggcg     420
ccggcgatgc aggacgtgtt ccgcgccatc ggccggctct cgcagtccaa cgtgacggtg     480
atgatcaccg gcgagtctgg caccggcaag gagctggtcg cacgcgcgct gcacaagcac     540
agcccgcgtg ccaacggtcc ctttatcgcg ctcaataccg cggccatccc caaggacctg     600
ctcgaatccg aactgttcgg ccatgagcgc ggcgccttca ccggtgcgca gaccatgcgg     660
```

```
cgcggccgct tcgagcaggc cgagggcggc acgctgttcc tcgacgaaat cggcgatatg    720
ccgttcgacc tgcagacgcg cctgctgcgc gtgctgtccg atggcaactt ctatcgtgtc    780
ggcggccaca accccttgcg cgccaatgtg cgcgtgattg ccgccaccca ccagaacctg    840
gagctgcgcg tcaaggaagg gctgttccgc gaggacttgt tccaccgcct gaacgtgatc    900
cggttgcgcc tgccgccgct gcgcgaacgc ccggaggaca tcacgctgct ggcgcgtcat    960
ttcctgcaga gagcgccaa ggaactgggc gtcgagccca gcgcatgtc cgacgaagcg    1020 ctggcctatg tcagcacgct gccattcccc ggcaacgtgc gccagctgga gaacctgtgc    1080
aactggctga ccgtgatggc gccggcccag accatcgagg tcaaggacct gccgcgcgag    1140
atgctggaag ccggcaccag cgagccggtc aatgcgccgc ggcccgagcg cgttgccgaa    1200
gcgcgcgcgc ccgagtatga aagcgcgcct gacctggccg actacggcgg ctacgcgacg    1260
acggtggcag aggccgacac ggccaccgca gtccggcccg cgtccgtggc gacggtggtc    1320
ccggccctgg cctcggccgg ctgggaaagc ctgctcgccg gcgaagcacg ggcaatgctc    1380
gaagccggcc agccggaggt catggatgtg ctgacgcgcc gcttcgagaa ggccgtgctg    1440
gaggccgcgc tgggtgtcac gcgcgggcgc gcgtcgagg cggcgacccg gctcgggatc    1500
gggcgcaata ccatcacgcg caagctgcag gagcttgggt tcgactga              1548
```

<210> SEQ ID NO 40
<211> LENGTH: 515
<212> TYPE: PRT
<213> ORGANISM: C. necator

<400> SEQUENCE: 40

```
Met Lys Pro Ile Trp Ile Val Asp Asp Gln Ser Ile Arg Trp Val
1               5                   10                  15

Leu Glu Lys Ala Leu Ala Arg Glu Ser Leu Leu Ser Arg Ser Phe Thr
            20                  25                  30

Asn Val Arg Asp Ala Leu Ala Ala Leu Glu Glu Asp Gln Pro Gln Val
        35                  40                  45

Leu Ile Ser Asp Ile Arg Met Pro Gly Gly Ser Gly Leu Asp Leu Leu
    50                  55                  60

Gln Ala Ile Lys Ala Arg His Pro Gly Leu Pro Val Ile Val Met Thr
65                  70                  75                  80

Ala Tyr Ser Asp Leu Asp Ser Ala Val Ala Ala Phe Gln Gly Gly Ala
                85                  90                  95

Phe Glu Tyr Leu Ala Lys Pro Phe Asp Val Asp Lys Ala Val Glu Leu
            100                 105                 110

Ile Arg Arg Ala Leu Glu Glu Ser Leu Arg Glu Glu Leu Asp Asp
        115                 120                 125

Arg Leu Val Asp Ala Pro Glu Ile Leu Gly Gln Ala Pro Ala Met Gln
130                 135                 140

Asp Val Phe Arg Ala Ile Gly Arg Leu Ser Gln Ser Asn Val Thr Val
145                 150                 155                 160

Met Ile Thr Gly Glu Ser Gly Thr Gly Lys Glu Leu Val Ala Arg Ala
                165                 170                 175

Leu His Lys His Ser Pro Arg Ala Asn Gly Pro Phe Ile Ala Leu Asn
            180                 185                 190

Thr Ala Ala Ile Pro Lys Asp Leu Leu Glu Ser Glu Leu Phe Gly His
        195                 200                 205

Glu Arg Gly Ala Phe Thr Gly Ala Gln Thr Met Arg Arg Gly Arg Phe
```

```
            210                 215                 220
Glu Gln Ala Glu Gly Gly Thr Leu Phe Leu Asp Glu Ile Gly Asp Met
225                 230                 235                 240

Pro Phe Asp Leu Gln Thr Arg Leu Leu Arg Val Leu Ser Asp Gly Asn
            245                 250                 255

Phe Tyr Arg Val Gly Gly His Asn Pro Leu Arg Ala Asn Val Arg Val
                260                 265                 270

Ile Ala Ala Thr His Gln Asn Leu Glu Leu Arg Val Lys Glu Gly Leu
            275                 280                 285

Phe Arg Glu Asp Leu Phe His Arg Leu Asn Val Ile Arg Leu Arg Leu
        290                 295                 300

Pro Pro Leu Arg Glu Arg Pro Glu Asp Ile Thr Leu Leu Ala Arg His
305                 310                 315                 320

Phe Leu Gln Lys Ser Ala Lys Glu Leu Gly Val Glu Pro Lys Arg Met
                325                 330                 335

Ser Asp Glu Ala Leu Ala Tyr Val Ser Thr Leu Pro Phe Pro Gly Asn
            340                 345                 350

Val Arg Gln Leu Glu Asn Leu Cys Asn Trp Leu Thr Val Met Ala Pro
        355                 360                 365

Ala Gln Thr Ile Glu Val Lys Asp Leu Pro Arg Glu Met Leu Glu Ala
370                 375                 380

Gly Thr Ser Glu Pro Val Asn Ala Pro Arg Pro Glu Arg Val Ala Glu
385                 390                 395                 400

Ala Arg Ala Pro Glu Tyr Glu Ser Ala Pro Asp Leu Ala Asp Tyr Gly
                405                 410                 415

Gly Tyr Ala Thr Thr Val Ala Glu Ala Asp Thr Ala Thr Ala Val Arg
            420                 425                 430

Pro Ala Ser Val Ala Thr Val Val Pro Ala Leu Ala Ser Ala Gly Trp
        435                 440                 445

Glu Ser Leu Leu Ala Gly Glu Ala Arg Ala Met Leu Glu Ala Gly Gln
450                 455                 460

Pro Glu Val Met Asp Val Leu Thr Arg Arg Phe Glu Lys Ala Val Leu
465                 470                 475                 480

Glu Ala Ala Leu Gly Val Thr Arg Gly Arg Val Glu Ala Ala Thr
                485                 490                 495

Arg Leu Gly Ile Gly Arg Asn Thr Ile Thr Arg Lys Leu Gln Glu Leu
            500                 505                 510

Gly Phe Asp
        515

<210> SEQ ID NO 41
<211> LENGTH: 1179
<212> TYPE: DNA
<213> ORGANISM: C. necator

<400> SEQUENCE: 41
atgcgtcgcc tgattcgcgg agtgtcgcgc aaggccagcg gtgccgacgg cgcccgtggc    60
gaatcgccgg cggctgatgc ggcgccggcc gaaggcagcg cccaggtgct gaccatgggc   120
gccgtggcgt tccatgccgg cctggacgta gtggccaacc cggtgctgct ggtgcagcag   180
ccggggctgc gcgtcgtctt tgcgaacccg gccgctgaag ccaccttcgg cgtgtcgcgc   240
aagggcatgg tggagctgac gctgcctgac ctgttcgggc gttccgatga gctgcacagc   300
atgatcgaca ccgtggtcac gcggcagttc gacgtgcgcc ggcaggacct gatcctgcac   360
```

```
ccgccgctgc aggagccggc ccatgtgcac gtggtgatct ccgcgctgga agcggtcggc    420
gacaccgtgg tggtggaaat cctgcccaat gaacagaagg tgcgcagcga acgcgaagaa    480
cgcatcctgg acctgacctc ggccaacaag gaactgatcc gcaacctggc ccacgaaatc    540
aagaacccgc tgggcggcat tcgcggcgcg gcgcagctgc tggagttcga gctgccggag    600
cgctcgctgc gcgaatacac gcaggtcatc atcaaggaat cggaccggct gcagacgctg    660
gtggaccggc tgctggagcc gcaccggcat ccgcatatcg tgtccagcct gaatatccac    720
gaagtgctgg agcgcgtgcg ctcggtggtg ctggcggagt tccccaacgg gctggagatc    780
gtgcgcgact acgacgccag cctgcccgag ctgcagggcg acatggagca actgatccag    840
gccgtgctca acatcgtgca acgccgcg caggcgctgg ccgaccgcat ggcgcgcggc    900
gatgcacaga tcgtgctgcg cacgcgcgtg gcgcgccagg tcacgattgc caagcgcttg    960
ttcaagctgg cattggactt gcatgtcatc gacaacggcc cgggaatttc cgaagacatc   1020
cgcgaacgca tcttctatcc gctggtatcg ggcagggatg gcggcagcgg actcggtctc   1080
acactcgctc aaaccttcgt gcagcagcac gagggcttga tcgaatgcga gagcaggccg   1140
ggctgtaccg acttccgcat cctgctgccg ctgcactag                          1179
```

<210> SEQ ID NO 42
<211> LENGTH: 392
<212> TYPE: PRT
<213> ORGANISM: C. necator

<400> SEQUENCE: 42

```
Met Arg Arg Leu Ile Arg Gly Val Ser Arg Lys Ala Ser Gly Ala Asp
1               5                   10                  15

Gly Ala Arg Gly Glu Ser Pro Ala Ala Asp Ala Ala Pro Ala Glu Gly
            20                  25                  30

Ser Ala Gln Val Leu Thr Met Gly Ala Val Ala Phe His Ala Gly Leu
        35                  40                  45

Asp Val Val Ala Asn Pro Val Leu Leu Val Gln Gln Pro Gly Leu Arg
    50                  55                  60

Val Val Phe Ala Asn Pro Ala Ala Glu Ala Thr Phe Gly Val Ser Arg
65                  70                  75                  80

Lys Gly Met Val Glu Leu Thr Leu Pro Asp Leu Phe Gly Arg Ser Asp
                85                  90                  95

Glu Leu His Ser Met Ile Asp Thr Val Val Thr Arg Gln Phe Asp Val
            100                 105                 110

Arg Arg Gln Asp Leu Ile Leu His Pro Pro Leu Gln Glu Pro Ala His
        115                 120                 125

Val His Val Val Ile Ser Ala Leu Glu Ala Val Gly Asp Thr Val Val
    130                 135                 140

Val Glu Ile Leu Pro Asn Glu Gln Lys Val Arg Ser Glu Arg Glu Glu
145                 150                 155                 160

Arg Ile Leu Asp Leu Thr Ser Ala Asn Lys Glu Leu Ile Arg Asn Leu
                165                 170                 175

Ala His Glu Ile Lys Asn Pro Leu Gly Gly Ile Arg Gly Ala Ala Gln
            180                 185                 190

Leu Leu Glu Phe Glu Leu Pro Glu Arg Ser Leu Arg Glu Tyr Thr Gln
        195                 200                 205

Val Ile Ile Lys Glu Ser Asp Arg Leu Gln Thr Leu Val Asp Arg Leu
    210                 215                 220

Leu Glu Pro His Arg His Pro His Ile Val Ser Ser Leu Asn Ile His
```

```
            225                 230                 235                 240
Glu Val Leu Glu Arg Val Arg Ser Val Val Leu Ala Glu Phe Pro Asn
                    245                 250                 255

Gly Leu Glu Ile Val Arg Asp Tyr Asp Ala Ser Leu Pro Glu Leu Gln
                260                 265                 270

Gly Asp Met Glu Gln Leu Ile Gln Ala Val Leu Asn Ile Val His Asn
            275                 280                 285

Ala Ala Gln Ala Leu Ala Asp Arg Met Ala Arg Gly Asp Ala Gln Ile
        290                 295                 300

Val Leu Arg Thr Arg Val Ala Arg Gln Val Thr Ile Ala Lys Arg Leu
305                 310                 315                 320

Phe Lys Leu Ala Leu Asp Leu His Val Ile Asp Asn Gly Pro Gly Ile
                325                 330                 335

Ser Glu Asp Ile Arg Glu Arg Ile Phe Tyr Pro Leu Val Ser Gly Arg
            340                 345                 350

Asp Gly Gly Ser Gly Leu Gly Leu Thr Leu Ala Gln Thr Phe Val Gln
        355                 360                 365

Gln His Glu Gly Leu Ile Glu Cys Glu Ser Arg Pro Gly Cys Thr Asp
    370                 375                 380

Phe Arg Ile Leu Leu Pro Leu His
385                 390

<210> SEQ ID NO 43
<211> LENGTH: 1416
<212> TYPE: DNA
<213> ORGANISM: C. necator

<400> SEQUENCE: 43
atggcccaca gcgttgcaga cgtgatgaag ctggtgaagg aaaacgacgt caagttcgtc    60
gatttccgtt tcaccgatac caaaggcaag gagcaacacg tgtccgtgcc cgtgtcgcac   120
ttcgatgaag acaagttcga aagcggccac gccttcgacg ttcgtcgat cgccggctgg    180 aagggtatcg aagcttcaga catgctgctg atgccggatt cgaacaccgc ccacatcgac   240
ccgttctacg aagagccgac gctggtgctg tcctgcgacg tggtcgagcc gtcggacggc   300
aagggctatg accgcgaccc gcgttccatc gccaagcgcg ccgaagccta cctgaagagc   360
accggcctgg cgacaccgc tttctttggt ccggagcccg agttcttcat cttcgacggc    420
gtgacctgga acgtcgacat gcaaggctgc ttcgtgaaga tccattccga agaagccccg   480
tggtcgtcgg ccaaggaatt cgagcacggc aacagcggcc accgtccggg caagaagggc   540
ggctacttcc cggtcgcccc gatcgacacc ttccaggaca tgcgttcgga atgtgcctg    600 atcctggaat cgctgggcat ccccgttgaa gtccaccacc acgaagtggc tgccagggc    660 cagaacgaaa tcggcacccg cttcagcacg ctggtgcagc gcgccgactg gacccagatg   720
cagaagtacg tgatccagaa cgtcgcccac acctacggca agaccgccac cttcatgccg   780
aagccgatcg ttggcgacaa cggttcgggc atgcacgtgc accagtccgt gtggaaggac   840
ggccagaacc tgttcgcggg caacggctac gccggcctgt cggaattcgc gctgtactac   900
atcggcggca tcatcaagca cgcccgtgcc ctgaatgcca tcaccaaccc gggcacgaac   960
tcgtacaagc gcctggtgcc gggcttcgaa gctccggtga agctggccta tcggcccgc   1020 aaccgctcgg cttcgatccg catcccgtat gtggccaacc gaagggccg ccgcatcgag   1080 acccgcttcc cggatccgct gatgaacccg tacctgggct tctcggcgct gctgatggcc   1140
ggcctggatg gcgtgatgaa caagatccac ccgggcgaag ctgccgacaa gaacctgtac   1200
```

```
gacctgccgc cggaagagga tgcaaagatc ccgaccgtgt gctcgagcct ggaccaggcg    1260
ctggagtacc tggacaacga ccgcgagttc ctgacccgcg gcggcgtgtt ctcgaactcg    1320
atgatcgatg cctacatcga actgaagatg gaagaagtca cgcgtttccg catgaccacg    1380
cacccggtcg agttcgaaat gtactactcg ctgtaa                              1416
```

<210> SEQ ID NO 44
<211> LENGTH: 471
<212> TYPE: PRT
<213> ORGANISM: C. necator

<400> SEQUENCE: 44

```
Met Ala His Ser Val Ala Asp Val Met Lys Leu Val Lys Glu Asn Asp
1               5                   10                  15

Val Lys Phe Val Asp Phe Arg Phe Thr Asp Thr Lys Gly Lys Glu Gln
            20                  25                  30

His Val Ser Val Pro Val Ser His Phe Asp Glu Asp Lys Phe Glu Ser
        35                  40                  45

Gly His Ala Phe Asp Gly Ser Ser Ile Ala Gly Trp Lys Gly Ile Glu
    50                  55                  60

Ala Ser Asp Met Leu Leu Met Pro Asp Ser Asn Thr Ala His Ile Asp
65                  70                  75                  80

Pro Phe Tyr Glu Glu Pro Thr Leu Val Leu Ser Cys Asp Val Val Glu
                85                  90                  95

Pro Ser Asp Gly Lys Gly Tyr Asp Arg Asp Pro Arg Ser Ile Ala Lys
            100                 105                 110

Arg Ala Glu Ala Tyr Leu Lys Ser Thr Gly Leu Gly Asp Thr Ala Phe
        115                 120                 125

Phe Gly Pro Glu Pro Glu Phe Phe Ile Phe Asp Gly Val Thr Trp Asn
    130                 135                 140

Val Asp Met Gln Gly Cys Phe Val Lys Ile His Ser Glu Glu Ala Pro
145                 150                 155                 160

Trp Ser Ser Ala Lys Glu Phe Glu His Gly Asn Ser Gly His Arg Pro
                165                 170                 175

Gly Lys Lys Gly Gly Tyr Phe Pro Val Ala Pro Ile Asp Thr Phe Gln
            180                 185                 190

Asp Met Arg Ser Glu Met Cys Leu Ile Leu Glu Ser Leu Gly Ile Pro
        195                 200                 205

Val Glu Val His His His Glu Val Ala Gly Gln Gly Gln Asn Glu Ile
    210                 215                 220

Gly Thr Arg Phe Ser Thr Leu Val Gln Arg Ala Asp Trp Thr Gln Met
225                 230                 235                 240

Gln Lys Tyr Val Ile Gln Asn Val Ala His Thr Tyr Gly Lys Thr Ala
                245                 250                 255

Thr Phe Met Pro Lys Pro Ile Val Gly Asp Asn Gly Ser Gly Met His
            260                 265                 270

Val His Gln Ser Val Trp Lys Asp Gly Gln Asn Leu Phe Ala Gly Asn
        275                 280                 285

Gly Tyr Ala Gly Leu Ser Glu Phe Ala Leu Tyr Ile Gly Gly Ile
    290                 295                 300

Ile Lys His Ala Arg Ala Leu Asn Ala Ile Thr Asn Pro Gly Thr Asn
305                 310                 315                 320

Ser Tyr Lys Arg Leu Val Pro Gly Phe Glu Ala Pro Val Lys Leu Ala
                325                 330                 335
```

Tyr Ser Ala Arg Asn Arg Ser Ala Ser Ile Arg Ile Pro Tyr Val Ala
            340                 345                 350

Asn Pro Lys Gly Arg Arg Ile Glu Thr Arg Phe Pro Asp Pro Leu Met
        355                 360                 365

Asn Pro Tyr Leu Gly Phe Ser Ala Leu Leu Met Ala Gly Leu Asp Gly
370                 375                 380

Val Met Asn Lys Ile His Pro Gly Glu Ala Ala Asp Lys Asn Leu Tyr
385                 390                 395                 400

Asp Leu Pro Pro Glu Glu Asp Ala Lys Ile Pro Thr Val Cys Ser Ser
            405                 410                 415

Leu Asp Gln Ala Leu Glu Tyr Leu Asp Asn Asp Arg Glu Phe Leu Thr
            420                 425                 430

Arg Gly Gly Val Phe Ser Asn Ser Met Ile Asp Ala Tyr Ile Glu Leu
            435                 440                 445

Lys Met Glu Glu Val Thr Arg Phe Arg Met Thr Thr His Pro Val Glu
        450                 455                 460

Phe Glu Met Tyr Tyr Ser Leu
465                 470

<210> SEQ ID NO 45
<211> LENGTH: 771
<212> TYPE: DNA
<213> ORGANISM: C. necator

<400> SEQUENCE: 45
atgaccctga atcccgcca gacggccctg ctcgaagaag tccgcaccca gggctttgcc      60
tccatcgacg aacttgcgcg caaattcggc gtcacgctcc agacggtgcg ccgcgatgtc     120
aacctgctgg ccgggaacgg catgctggcg cgcttccatg gcggggtgcg ggtggagggc     180
tccaccaccg agaacatcgc ctaccggcag cggcaggtgc tcaacgccga gggcaaggcg     240
cgcatcgcgc gcgcggtggc cgctgcggtg cccgagggct gctcgctgat cctgaacatc     300
ggcaccacgg tggaagagat agcgcgcgaa ctgatgcacc accgcgggct gcgcgtgatc     360
accaacaacc tgaatgtggc caatatcctt gccgacaacc ccgattgcga ggtcatcgtc     420
gccggcggcg tgctgcgctc acgcgaccgc ggcatcgtgg gcgaggccac ggtggagttc     480
atccgccagt tcaaggtgga tatcgggctg atcggcatct cgggcatcga accgacggc     540
acgctgcgcg actacgattt ccgcgaggtc aaggtggcgc ggaccatcat cgagcattca     600
cgcgaggtgt ggctggcggc ggacgccagc aagttcaatc gccaggcgat ggtggagctg     660
gcgcatgtgt cgcaggtcga ccggctcttt accgacgagc cgctggcagc gccgttcgac     720
cagatcgtgg ccgacagtgg ggtgaagtgt gtggtggcgg agcgggagtg a            771

<210> SEQ ID NO 46
<211> LENGTH: 256
<212> TYPE: PRT
<213> ORGANISM: C. necator

<400> SEQUENCE: 46

Met Thr Leu Asn Pro Arg Gln Thr Ala Leu Leu Glu Glu Val Arg Thr
1               5                   10                  15

Gln Gly Phe Ala Ser Ile Asp Glu Leu Ala Arg Lys Phe Gly Val Thr
            20                  25                  30

Leu Gln Thr Val Arg Arg Asp Val Asn Leu Leu Ala Gly Asn Gly Met
        35                  40                  45

```
Leu Ala Arg Phe His Gly Gly Val Arg Val Glu Gly Ser Thr Thr Glu
 50                  55                  60
Asn Ile Ala Tyr Arg Gln Arg Gln Val Leu Asn Ala Glu Gly Lys Ala
 65                  70                  75                  80
Arg Ile Ala Arg Ala Val Ala Ala Val Pro Glu Gly Cys Ser Leu
                 85                  90                  95
Ile Leu Asn Ile Gly Thr Thr Val Glu Glu Ile Ala Arg Glu Leu Met
                100                 105                 110
His His Arg Gly Leu Arg Val Ile Thr Asn Asn Leu Asn Val Ala Asn
                115                 120                 125
Ile Leu Ala Asp Asn Pro Asp Cys Glu Val Ile Val Ala Gly Gly Val
130                 135                 140
Leu Arg Ser Arg Asp Arg Gly Ile Val Gly Glu Ala Thr Val Glu Phe
145                 150                 155                 160
Ile Arg Gln Phe Lys Val Asp Ile Gly Leu Ile Gly Ile Ser Gly Ile
                165                 170                 175
Glu Thr Asp Gly Thr Leu Arg Asp Tyr Asp Phe Arg Gly Val Lys Val
                180                 185                 190
Ala Arg Thr Ile Ile Glu His Ser Arg Glu Val Trp Leu Ala Ala Asp
                195                 200                 205
Ala Ser Lys Phe Asn Arg Gln Ala Met Val Glu Leu Ala His Val Ser
210                 215                 220
Gln Val Asp Arg Leu Phe Thr Asp Glu Pro Leu Ala Ala Pro Phe Asp
225                 230                 235                 240
Gln Ile Val Ala Asp Ser Gly Val Lys Cys Val Val Ala Glu Arg Glu
                245                 250                 255

<210> SEQ ID NO 47
<211> LENGTH: 1464
<212> TYPE: DNA
<213> ORGANISM: C. necator

<400> SEQUENCE: 47
atgggtaagg cgactggctt tctcgaattt ccgcgccaga cgaaggcta cgaaccggta      60 gtcaagcgcg tgaagcacta caaggaattc gtgttcgcgc tgtccgacag cgaagcgaag     120
atccagggtg cgcgctgcat ggactgcggc atcccgttct gcaacaacgg ctgcccggtc     180
aacaacatca tccccgactt caacgacctg gtgtaccgcc aggactggaa gtcggcgatc     240
gaggtgctgc accagaccaa caacttcccc gagttcaccg ccgcatctg ccccgcaccg      300 tgcgaggccg cctgcacgct gggcatcaat gaactgccgg tgggcatcaa gtcgatcgag     360
cacgccatca tcgacaaggc ctgggaagag gctgggtca ggccgcagct gccgcgccac      420
aagaccggca gaccgtggc cgtggtcggc tccggtcccg ccggcatggc tgccgcgcag     480
cagctggcac gcgccggcca tgacgtgacc gtgttcgaga agaacgaccg catcggcggc     540
ctgctgcgct acggcatccc cgacttcaag atggagaaga cgctgatcga ccgccgcatc     600
gagcagatgc aggccgaagg cgtgaccttc cgtccgggcg tgatggtgac cgacggcgaa     660
ctgccggccg gcatcaagaa ctacgcccgt gaaaccatct cggcccaggc cctgatggac     720
cagttcgacg ccgtggtgct ggcggcggc tcggaagtgc cgcgcgacct gccggtgccg     780
ggccgcgacc tggccggcat ccacttcgcg ctggaattcc tgatcccgca gaacaaggaa     840
gtggcaggcg acggcgaaaa cgagatccgc gccgaaggca agaacgtgat tgtgatcggt     900
ggcggcgata ccggctccga ctgcgtgggt acgtccaacc gccatggcgc cacctcggtg     960
```

```
acgcagtttg aactgctgcc gcagccgccg gaagaagagg acaagccgct ggtgtggccg    1020
tactggccga tcaagctgcg cacctcgtcg tcgcacgatg aaggctgcga gcgagactgg    1080
tcggtcgcca ccaaggaatt catcggcgag aacggcaagg tcaccgcact gaaggcctgc    1140
cgtgtcgaat ggaaggatgg ccgcatgcag gaagtcgaag cagcgagtt catcctgccg     1200 gccgacctgg tgctgctggc gatgggcttt accaacccgg tgggttcgat gctggaagcg    1260
tttggcgtgg ataccgatgc gcgcaagaac gccaaggcct cgaccgaggg cgagcgtgcc    1320
taccacacca acgtgcccaa ggtgttcgcc gctggcgacg tgcgccgtgg ccagtcgctg    1380
gtggtgtggg cgatccgcga aggccgccag gccgcgcgtt cggtcgatgc cttcctgatg    1440
ggtcacaccg aactgccgcg ctga                                            1464
```

<210> SEQ ID NO 48
<211> LENGTH: 487
<212> TYPE: PRT
<213> ORGANISM: C. necator

<400> SEQUENCE: 48

```
Met Gly Lys Ala Thr Gly Phe Leu Glu Phe Pro Arg Gln Asn Glu Gly
1               5                   10                  15

Tyr Glu Pro Val Val Lys Arg Val Lys His Tyr Lys Glu Phe Val Phe
                20                  25                  30

Ala Leu Ser Asp Ser Glu Ala Lys Ile Gln Gly Ala Arg Cys Met Asp
            35                  40                  45

Cys Gly Ile Pro Phe Cys Asn Asn Gly Cys Pro Val Asn Asn Ile Ile
        50                  55                  60

Pro Asp Phe Asn Asp Leu Val Tyr Arg Gln Asp Trp Lys Ser Ala Ile
65                  70                  75                  80

Glu Val Leu His Gln Thr Asn Asn Phe Pro Glu Phe Thr Gly Arg Ile
                85                  90                  95

Cys Pro Ala Pro Cys Glu Ala Ala Cys Thr Leu Gly Ile Asn Glu Leu
            100                 105                 110

Pro Val Gly Ile Lys Ser Ile Glu His Ala Ile Ile Asp Lys Ala Trp
        115                 120                 125

Glu Glu Gly Trp Val Arg Pro Gln Leu Pro Arg His Lys Thr Gly Lys
    130                 135                 140

Thr Val Ala Val Val Gly Ser Gly Pro Ala Gly Met Ala Ala Ala Gln
145                 150                 155                 160

Gln Leu Ala Arg Ala Gly His Asp Val Thr Val Phe Glu Lys Asn Asp
                165                 170                 175

Arg Ile Gly Gly Leu Leu Arg Tyr Gly Ile Pro Asp Phe Lys Met Glu
            180                 185                 190

Lys Thr Leu Ile Asp Arg Arg Ile Glu Gln Met Gln Ala Glu Gly Val
        195                 200                 205

Thr Phe Arg Pro Gly Val Met Val Thr Asp Gly Glu Leu Pro Ala Gly
    210                 215                 220

Ile Lys Asn Tyr Ala Arg Glu Thr Ile Ser Ala Gln Ala Leu Met Asp
225                 230                 235                 240

Gln Phe Asp Ala Val Leu Ala Gly Gly Ser Glu Val Pro Arg Asp
                245                 250                 255

Leu Pro Val Pro Gly Arg Asp Leu Ala Gly Ile His Phe Ala Leu Glu
            260                 265                 270

Phe Leu Ile Pro Gln Asn Lys Glu Val Ala Gly Asp Gly Glu Asn Glu
        275                 280                 285
```

```
Ile Arg Ala Glu Gly Lys Asn Val Ile Val Ile Gly Gly Asp Thr
    290                 295                 300
Gly Ser Asp Cys Val Gly Thr Ser Asn Arg His Gly Ala Thr Ser Val
305                 310                 315                 320
Thr Gln Phe Glu Leu Leu Pro Gln Pro Pro Glu Glu Asp Lys Pro
                325                 330                 335
Leu Val Trp Pro Tyr Trp Pro Ile Lys Leu Arg Thr Ser Ser His
                340                 345                 350
Asp Glu Gly Cys Glu Arg Asp Trp Ser Val Ala Thr Lys Glu Phe Ile
                355                 360                 365
Gly Glu Asn Gly Lys Val Thr Ala Leu Lys Ala Cys Arg Val Glu Trp
    370                 375                 380
Lys Asp Gly Arg Met Gln Glu Val Glu Gly Ser Glu Phe Ile Leu Pro
385                 390                 395                 400
Ala Asp Leu Val Leu Leu Ala Met Gly Phe Thr Asn Pro Val Gly Ser
                405                 410                 415
Met Leu Glu Ala Phe Gly Val Asp Thr Asp Ala Arg Lys Asn Ala Lys
                420                 425                 430
Ala Ser Thr Glu Gly Glu Arg Ala Tyr His Thr Asn Val Pro Lys Val
                435                 440                 445
Phe Ala Ala Gly Asp Val Arg Arg Gly Gln Ser Leu Val Val Trp Ala
    450                 455                 460
Ile Arg Glu Gly Arg Gln Ala Ala Arg Ser Val Asp Ala Phe Leu Met
465                 470                 475                 480
Gly His Thr Glu Leu Pro Arg
                485

<210> SEQ ID NO 49
<211> LENGTH: 4806
<212> TYPE: DNA
<213> ORGANISM: C. necator

<400> SEQUENCE: 49
gtggaccaaa cgaaaaatct ttcggcccaa gctcaggcac aagcgcagac cagcgagtct     60
tcccacgcca ttgacctgcg cccgcaagcg cagggcatgt acgatcccag caacgagcat    120
gacgcctgcg cgtcggcat ggtcgcgcat atcaagggca agaagtccca cgagatcatc    180
tcgcagggcc tgaagatcct ggagaacctg gaccaccggg gtgcggtcgg cgccgatgcg    240
ctgatgggcg acggtgccgg catcctgatc cagatcccgg accagttcta ccgcgaggaa    300
atggccgcgc agggcgtgag cctgccgccc gccggcgaat acgcgtgggg catgatcttc    360
ctgccgaagg aacacgcctc gcgcctggcc tgcgagcagg aactggagcg cacggtccgc    420
ctggaaggcc aggtcgtgct gggctggcgc gacgtgccgg tcgacgccaa gatgccgatg    480
tcgccgacgg tgcgcaccac cgagccggtg atccgccaga tcttcatcgg cgcgcggccgc    540 gacatcatga ccacggacgc gctggaacgt aagctctacg tcatccgcaa gaccgccagc    600
catgccatcc aggcgctcaa gctcaagcac ggcaaggaat acttcgtgcc gtcaatgtcg    660
gcccgtaccg tggtgtacaa gggcctgctg ctggccaacc aggttggcga gtactacctg    720
gacctgctgg accagcgcgc cgtctcggcc ctggccctgg tgcaccagcg cttctcgacc    780
aacaccttcc cggcctggga actggccac ccgtaccgca tggtcgccca acggcgaa    840 atcaacacgt caagggcaa tgtcaactgg atcaacgcgc gcaccggcgc gatctcgtcg    900
ccggtgctcg gcgacgacct gcccaagctg tggccgctga tctacccggg ccagtccgac    960
```

```
accgcatcgt tcgacaactg cctcgaactg ctgacgatgg ccggctaccc gctcgtccac    1020
gcgatgatga tgatgatccc ggaagcctgg aacagcaca cgctgatgga cgacaaccgc    1080
cgcgccttct acgagtacca cgccgccatg atggagccgt gggacggccc ggccgcgatc    1140
tgcttcaccg atggccgcca gatcggcgcc acgctggacc gcaacggcct cgcccggca    1200 cgtttctacg tgaccgagga cgacatcgtg gtgctggctt cggaagccgg cgtgctgccg    1260
ttccccgagt cgcgcatcgt tgagaagtgg cgcctgcagc cgggcaagat gttcctgatc    1320
gacatggaac agggccgcat catcgacgac aaggaactca aggacaacct ggccaacgcc    1380
aagccgtaca gagctggat cgacgccgtg cgcatcaagc tcgacgagct cgacgccaag    1440
cctgaagacg ttgccgccga agaagcccc gtggccaagc tgctggaccg ccagcaggcc    1500
tttggctaca cccaggaaga cgtcaagttc ctgatggcgc cgatggcgct ggccggcgag    1560
gaagccaccg gctcgatggg caacgattcg ccgctggcca tcctgtcgtc caagaacaag    1620
acgctgtacc actacttcaa gcagctgttc gcccaggtca ccaacccgcc gatcgacccg    1680
atccgcgaga acatggtgat gtcgctggtg tcgttcatcg gcccgaagcc gaacctgctc    1740
gagctgaaca acatcaaccc gccgatgcgc ctcgaagtgt cccagccggt gctggacttc    1800
aaggacatcg ccaagatccg caatatcgag cactacaccg gcggcaagtt ccgttcgtac    1860
gagctgaaca tctgctaccc gaaggcctgg ggcaaggagg catcgaagc gcgcctggcc    1920 tcgctgtgcg ccgaagccgt ggatgcggtg cgttcgggct tcaacatcct gatcgtgtcg    1980
gaccgccgcg tggatgccga gcatgttgcg attcccgcgc tgctggccac gtccgccatc    2040
caccaccacc tggtggagaa gggcctgcgc acgtccaccg gctggtggt cgagaccggc    2100 accgccgtg aagtgcacca cttcgcgctg ctggccggct atggcgccga agccgtgcat    2160
ccgtacctgg cgatggaaac gctggccgaa atggcccagg gctgtccgg cgacctgtcg    2220 cccgagaagg cggtcaagaa cttcgtcaag gcgatcggca agggcctgtt caaagtgatg    2280
tccaagatgg gcatctccac ctacatgtcg tacaccggcg cgcagatctt cgaagccatc    2340
ggcctgtcgc gcgaactggt gcagaagtac ttccatggca ccccgtcgaa tgtcgagggc    2400
atcggcatct tcgaagtggc cgaggaagcc ctgcgcctgc accgcgacgc ctttggcgac    2460
aacccggtgc tggaaagcat gctggacgcc ggcggcgaat acgccttccg catccgcggc    2520
gaagagcata tgtggacccc ggactcggtc gccaagctgc agcactcggt gcgcgccgac    2580
gacggcaagg gcgcctacca gacgtacaag gaatacgcca acatcatcaa cgaccagagc    2640
aagcgccaca tgacgctgcg tggcctgttc gagttcaagg tcgatccggc caaggcgatt    2700
ccgctggaag aggtggagtc ggccaaggag atcgtcaagc gcttcgccac cggtgcgatg    2760
tcgctcggct cgatctcgac cgaagcccac accacgctgg cgctggcgat gaccgcatc    2820 ggcggcaagt ccaacaccgg cgaaggcggc gaggacgaga agcgctaccg caacgagctg    2880
cgcggcattc ccatcaagca gggcgatacc ctcaagggcc tgctgggcga acgtgatc    2940 gaacgcgacc tggaactgca ggaaggcgat tcgctgcgct cgaagatcaa gcaggtggcg    3000
tcgggccgtt tcggcgtgac cgccgaatac ctggcttcgg ccgaccagat ccagatcaag    3060
atggcgcagg gtgccaagcc cggcgaaggc ggccagctgc ccggcacaa ggtctcggac    3120 tacatcggca agctgcgtta ctcggtgccg ggcgtgggcc tgatctcgcc gccccgcac    3180 catgacatct attcgatcga ggatctggca cagctgatcc acgacctgaa gaacgtcaac    3240
ccggtgtcgg acatctcggt caagctggtg tccgaagtcg gcgtcggcac ggtggccgcg    3300
```

```
ggcgtggcca aggccaaggc cgaccacgtc gtgatcgccg ccatgatgg cggcaccggc      3360 gcttcgccgt ggtcgtcgat caagcatgcc ggcacgccgt gggagctggg cctggccgaa      3420
acgcagcaga cgctgctgct caacggcctg cgcaaccgca tccgcgtgca ggccgacggc      3480
cagatgaaga ccggccgcga cgtcgtcatc ggcgcgctgc tgggcgccga tgaattcggc      3540
ttcgccaccg cgccgctggt tgcggaaggc tgcatcatga tgcgcaagtg ccacctgaac      3600
acctgcccgg tgggcgtggc cacgcaggat ccgcagctgc gcaggaagtt ccagggcaag      3660
cctgagcacg tggtcaactt cttcttcttc gttgcggaag aagcccgcga atcatggcc      3720 cagctgggca tccgcaagtt cgacgagctg atcggccgcg ccgacctgct cgacaccaag      3780
cccggcatcg agcactggaa ggcgcgcggc ctggacttcg ccgcatctt ccaccaggtc      3840 tcgctgggcg cggacgtgcc gctgtaccac accgacgtgc aggaccacgg cctgtcggcc      3900
gaggccggca aggcgctgga ccacgtgctg atcgccaagg cccgaccggc gatcgagaag      3960
ggcgagcggg tctcgttcat ccagccggtg aagaacgtca accgtaccgt cggcgcgatg      4020
ctgtcgggcg tggtggcgcg ccagcatggc cacgaaggcc tgcctgacga taccatccac      4080
atccagctgc aaggcaccgc cggccagtcg ttcgcgcgt cctggcgca cggcatcacg      4140 ctggacctgg tgggcgacgg caacgactat gtcggcaagg gcctgtcggg cggccgcgtg      4200
atcgtgcgcg ctccgcatga gttccgcggc gacccgaccc gcaacatcat cgtcggcaac      4260
accgtgctgt acggtgctat cgccggggaa gcgttcttca acggcgtggc cggcgagcgc      4320
ttcgcggtgc gcaactcggg tgcggtggca gtggtggaag gcaccggcga ccacggttgc      4380
gagtacatga ccggcggcac ggtggtggtg ctgggcggca ccggacgcaa cttcgcggcc      4440
ggcatgtcgg gcggcgtggc ctacgtctac gacgaggacg gcctgttcga caagcgctgc      4500
aacacctcga tggtggcgct ggaagcagtg ctggcttcgg ccgaccagga gaagggccag      4560
cccgaggctt cgtggcacaa ggtcgacggc aagcgccagc tggatgaggt catcctgcgc      4620
aacctgatcg agcagcattt ccgctacacc ggttccgagc gcgccaaggc gctgctggcc      4680
gactggacca cggcacgccg caagttcgtc aaggtcttcc cgaccgagta caagcgcgcg      4740
ctgggcgaga tgtacgccaa ggaacaggcc gcccgcgaca cgaccgcga agccatcgcg      4800 gcctga                                                                4806
```

<210> SEQ ID NO 50
<211> LENGTH: 1601
<212> TYPE: PRT
<213> ORGANISM: C. necator

<400> SEQUENCE: 50

```
Met Asp Gln Thr Lys Asn Leu Ser Ala Gln Ala Gln Ala Gln Ala Gln
1               5                   10                  15

Thr Ser Glu Ser Ser His Ala Ile Asp Leu Arg Pro Gln Ala Gln Gly
                20                  25                  30

Met Tyr Asp Pro Ser Asn Glu His Asp Ala Cys Gly Val Gly Met Val
            35                  40                  45

Ala His Ile Lys Gly Lys Lys Ser His Glu Ile Ile Ser Gln Gly Leu
        50                  55                  60

Lys Ile Leu Glu Asn Leu Asp His Arg Gly Ala Val Gly Ala Asp Ala
65                  70                  75                  80

Leu Met Gly Asp Gly Ala Gly Ile Leu Ile Gln Ile Pro Asp Gln Phe
                85                  90                  95

Tyr Arg Glu Glu Met Ala Ala Gln Gly Val Ser Leu Pro Pro Ala Gly
```

```
            100                 105                 110
Glu Tyr Gly Val Gly Met Ile Phe Leu Pro Lys Glu His Ala Ser Arg
            115                 120                 125

Leu Ala Cys Glu Gln Glu Leu Glu Arg Thr Val Arg Leu Glu Gly Gln
            130                 135             140

Val Val Leu Gly Trp Arg Asp Val Pro Val Asp Ala Lys Met Pro Met
145             150                 155                 160

Ser Pro Thr Val Arg Thr Thr Glu Pro Val Ile Arg Gln Ile Phe Ile
                165                 170                 175

Gly Arg Gly Arg Asp Ile Met Thr Thr Asp Ala Leu Glu Arg Lys Leu
            180                 185             190

Tyr Val Ile Arg Lys Thr Ala Ser His Ala Ile Gln Ala Leu Lys Leu
            195                 200             205

Lys His Gly Lys Glu Tyr Phe Val Pro Ser Met Ser Ala Arg Thr Val
        210                 215                 220

Val Tyr Lys Gly Leu Leu Leu Ala Asn Gln Val Gly Glu Tyr Tyr Leu
225                 230                 235                 240

Asp Leu Leu Asp Gln Arg Ala Val Ser Ala Leu Ala Leu Val His Gln
                245                 250                 255

Arg Phe Ser Thr Asn Thr Phe Pro Ala Trp Glu Leu Ala His Pro Tyr
            260                 265                 270

Arg Met Val Ala His Asn Gly Glu Ile Asn Thr Val Lys Gly Asn Val
            275                 280                 285

Asn Trp Ile Asn Ala Arg Thr Gly Ala Ile Ser Ser Pro Val Leu Gly
        290                 295                 300

Asp Asp Leu Pro Lys Leu Trp Pro Leu Ile Tyr Pro Gly Gln Ser Asp
305                 310                 315                 320

Thr Ala Ser Phe Asp Asn Cys Leu Glu Leu Leu Thr Met Ala Gly Tyr
                325                 330                 335

Pro Leu Val His Ala Met Met Met Met Ile Pro Glu Ala Trp Glu Gln
            340                 345                 350

His Thr Leu Met Asp Asp Asn Arg Arg Ala Phe Tyr Glu Tyr His Ala
            355                 360                 365

Ala Met Met Glu Pro Trp Asp Gly Pro Ala Ala Ile Cys Phe Thr Asp
        370                 375                 380

Gly Arg Gln Ile Gly Ala Thr Leu Asp Arg Asn Gly Leu Arg Pro Ala
385                 390                 395                 400

Arg Phe Tyr Val Thr Glu Asp Asp Ile Val Val Leu Ala Ser Glu Ala
                405                 410                 415

Gly Val Leu Pro Phe Pro Glu Ser Arg Ile Val Glu Lys Trp Arg Leu
            420                 425                 430

Gln Pro Gly Lys Met Phe Leu Ile Asp Met Glu Gln Gly Arg Ile Ile
            435                 440                 445

Asp Asp Lys Glu Leu Lys Asp Asn Leu Ala Asn Ala Lys Pro Tyr Lys
        450                 455                 460

Ser Trp Ile Asp Ala Val Arg Ile Lys Leu Asp Glu Leu Asp Ala Lys
465                 470                 475                 480

Pro Glu Asp Val Ala Ala Glu Lys Lys Pro Val Ala Lys Leu Leu Asp
                485                 490                 495

Arg Gln Gln Ala Phe Gly Tyr Thr Gln Glu Asp Val Lys Phe Leu Met
            500                 505                 510

Ala Pro Met Ala Leu Ala Gly Glu Glu Ala Thr Gly Ser Met Gly Asn
            515                 520                 525
```

```
Asp Ser Pro Leu Ala Ile Leu Ser Ser Lys Asn Lys Thr Leu Tyr His
    530                 535                 540

Tyr Phe Lys Gln Leu Phe Ala Gln Val Thr Asn Pro Pro Ile Asp Pro
545                 550                 555                 560

Ile Arg Glu Asn Met Val Met Ser Leu Val Ser Phe Ile Gly Pro Lys
                565                 570                 575

Pro Asn Leu Leu Glu Leu Asn Asn Ile Asn Pro Pro Met Arg Leu Glu
                580                 585                 590

Val Ser Gln Pro Val Leu Asp Phe Lys Asp Ile Ala Lys Ile Arg Asn
                595                 600                 605

Ile Glu His Tyr Thr Gly Gly Lys Phe Arg Ser Tyr Glu Leu Asn Ile
    610                 615                 620

Cys Tyr Pro Lys Ala Trp Gly Lys Glu Gly Ile Glu Ala Arg Leu Ala
625                 630                 635                 640

Ser Leu Cys Ala Glu Ala Val Asp Ala Val Arg Ser Gly Phe Asn Ile
                645                 650                 655

Leu Ile Val Ser Asp Arg Arg Val Asp Ala Glu His Val Ala Ile Pro
                660                 665                 670

Ala Leu Leu Ala Thr Ser Ala Ile His His Leu Val Glu Lys Gly
                675                 680                 685

Leu Arg Thr Ser Thr Gly Leu Val Val Glu Thr Gly Thr Ala Arg Glu
    690                 695                 700

Val His His Phe Ala Leu Leu Ala Gly Tyr Gly Ala Glu Ala Val His
705                 710                 715                 720

Pro Tyr Leu Ala Met Glu Thr Leu Ala Glu Met Ala Gln Gly Leu Ser
                725                 730                 735

Gly Asp Leu Ser Pro Glu Lys Ala Val Lys Asn Phe Val Lys Ala Ile
                740                 745                 750

Gly Lys Gly Leu Phe Lys Val Met Ser Lys Met Gly Ile Ser Thr Tyr
    755                 760                 765

Met Ser Tyr Thr Gly Ala Gln Ile Phe Glu Ala Ile Gly Leu Ser Arg
770                 775                 780

Glu Leu Val Gln Lys Tyr Phe His Gly Thr Pro Ser Asn Val Glu Gly
785                 790                 795                 800

Ile Gly Ile Phe Glu Val Ala Glu Glu Ala Leu Arg Leu His Arg Asp
                805                 810                 815

Ala Phe Gly Asp Asn Pro Val Leu Glu Ser Met Leu Asp Ala Gly Gly
                820                 825                 830

Glu Tyr Ala Phe Arg Ile Arg Gly Glu His Met Trp Thr Pro Asp
    835                 840                 845

Ser Val Ala Lys Leu Gln His Ser Val Arg Ala Asp Asp Gly Lys Gly
    850                 855                 860

Ala Tyr Gln Thr Tyr Lys Glu Tyr Ala Asn Ile Ile Asn Asp Gln Ser
865                 870                 875                 880

Lys Arg His Met Thr Leu Arg Gly Leu Phe Glu Phe Lys Val Asp Pro
                885                 890                 895

Ala Lys Ala Ile Pro Leu Glu Glu Val Glu Ser Ala Lys Glu Ile Val
                900                 905                 910

Lys Arg Phe Ala Thr Gly Ala Met Ser Leu Gly Ser Ile Ser Thr Glu
    915                 920                 925

Ala His Thr Thr Leu Ala Leu Ala Met Asn Arg Ile Gly Gly Lys Ser
    930                 935                 940
```

```
Asn Thr Gly Glu Gly Gly Glu Asp Glu Lys Arg Tyr Arg Asn Glu Leu
945                 950                 955                 960

Arg Gly Ile Pro Ile Lys Gln Gly Asp Thr Leu Lys Gly Leu Leu Gly
            965                 970                 975

Asp Asn Val Ile Glu Arg Asp Leu Glu Leu Gln Glu Gly Asp Ser Leu
            980                 985                 990

Arg Ser Lys Ile Lys Gln Val Ala Ser Gly Arg Phe Gly Val Thr Ala
        995                 1000                1005

Glu Tyr Leu Ala Ser Ala Asp Gln Ile Gln Ile Lys Met Ala Gln
    1010                1015                1020

Gly Ala Lys Pro Gly Glu Gly Gly Gln Leu Pro Gly His Lys Val
    1025                1030                1035

Ser Asp Tyr Ile Gly Lys Leu Arg Tyr Ser Val Pro Gly Val Gly
    1040                1045                1050

Leu Ile Ser Pro Pro His His Asp Ile Tyr Ser Ile Glu Asp
    1055                1060                1065

Leu Ala Gln Leu Ile His Asp Leu Lys Asn Val Asn Pro Val Ser
    1070                1075                1080

Asp Ile Ser Val Lys Leu Val Ser Glu Val Gly Val Gly Thr Val
    1085                1090                1095

Ala Ala Gly Val Ala Lys Ala Lys Ala Asp His Val Val Ile Ala
    1100                1105                1110

Gly His Asp Gly Gly Thr Gly Ala Ser Pro Trp Ser Ser Ile Lys
    1115                1120                1125

His Ala Gly Thr Pro Trp Glu Leu Gly Leu Ala Glu Thr Gln Gln
    1130                1135                1140

Thr Leu Leu Leu Asn Gly Leu Arg Asn Arg Ile Arg Val Gln Ala
    1145                1150                1155

Asp Gly Gln Met Lys Thr Gly Arg Asp Val Val Ile Gly Ala Leu
    1160                1165                1170

Leu Gly Ala Asp Glu Phe Gly Phe Ala Thr Ala Pro Leu Val Ala
    1175                1180                1185

Glu Gly Cys Ile Met Met Arg Lys Cys His Leu Asn Thr Cys Pro
    1190                1195                1200

Val Gly Val Ala Thr Gln Asp Pro Gln Leu Arg Arg Lys Phe Gln
    1205                1210                1215

Gly Lys Pro Glu His Val Val Asn Phe Phe Phe Val Ala Glu
    1220                1225                1230

Glu Ala Arg Glu Ile Met Ala Gln Leu Gly Ile Arg Lys Phe Asp
    1235                1240                1245

Glu Leu Ile Gly Arg Ala Asp Leu Leu Asp Thr Lys Pro Gly Ile
    1250                1255                1260

Glu His Trp Lys Ala Arg Gly Leu Asp Phe Gly Arg Ile Phe His
    1265                1270                1275

Gln Val Ser Leu Gly Ala Asp Val Pro Leu Tyr His Thr Asp Val
    1280                1285                1290

Gln Asp His Gly Leu Ser Ala Glu Ala Gly Lys Ala Leu Asp His
    1295                1300                1305

Val Leu Ile Ala Lys Ala Arg Pro Ala Ile Glu Lys Gly Glu Arg
    1310                1315                1320

Val Ser Phe Ile Gln Pro Val Lys Asn Val Asn Arg Thr Val Gly
    1325                1330                1335

Ala Met Leu Ser Gly Val Val Ala Arg Gln His Gly His Glu Gly
```

| Leu | Pro | Asp | Asp | Thr | Ile | His | Ile | Gln | Leu | Gln | Gly | Thr | Ala | Gly |
| | 1355 | | | | 1360 | | | | | 1365 | | | | |

Gln Ser Phe Gly Ala Phe Leu Ala His Gly Ile Thr Leu Asp Leu
    1370            1375                    1380

Val Gly Asp Gly Asn Asp Tyr Val Gly Lys Gly Leu Ser Gly Gly
    1385            1390                    1395

Arg Val Ile Val Arg Ala Pro His Glu Phe Arg Gly Asp Pro Thr
1400                1405                    1410

Arg Asn Ile Ile Val Gly Asn Thr Val Leu Tyr Gly Ala Ile Ala
1415                1420                    1425

Gly Glu Ala Phe Phe Asn Gly Val Ala Gly Glu Arg Phe Ala Val
1430                1435                    1440

Arg Asn Ser Gly Ala Val Ala Val Val Glu Gly Thr Gly Asp His
1445                1450                    1455

Gly Cys Glu Tyr Met Thr Gly Gly Thr Val Val Leu Gly Gly
1460                1465                    1470

Thr Gly Arg Asn Phe Ala Ala Gly Met Ser Gly Val Ala Tyr
1475                1480                    1485

Val Tyr Asp Glu Asp Gly Leu Phe Asp Lys Arg Cys Asn Thr Ser
1490                1495                    1500

Met Val Ala Leu Glu Ala Val Leu Ala Ser Ala Asp Gln Glu Lys
1505                1510                    1515

Gly Gln Pro Glu Ala Ser Trp His Lys Val Asp Gly Lys Arg Gln
1520                1525                    1530

Leu Asp Glu Val Ile Leu Arg Asn Leu Ile Glu Gln His Phe Arg
1535                1540                    1545

Tyr Thr Gly Ser Glu Arg Ala Lys Ala Leu Leu Ala Asp Trp Thr
1550                1555                    1560

Thr Ala Arg Arg Lys Phe Val Lys Val Phe Pro Thr Glu Tyr Lys
1565                1570                    1575

Arg Ala Leu Gly Glu Met Tyr Ala Lys Glu Gln Ala Ala Arg Asp
1580                1585                    1590

Ser Asp Arg Glu Ala Ile Ala Ala
1595                1600

<210> SEQ ID NO 51
<211> LENGTH: 975
<212> TYPE: DNA
<213> ORGANISM: C. necator

<400> SEQUENCE: 51

```
atgaagaccg gcaaaagctc ggcaggagac accaaggccc ggattctcga cgccacggaa      60
aagttgttta ccgaggtcgg ctatgaagcc acctcgctca ggcaggtcac gtcgcgcgcc     120
atcgtcaacc tggccgccgt gaactaccac ttccgcagca agatatcat gatgcacgcc      180 gtgctgagcc ggcggctgga tccgctcaac gcgcggcgcc tggcgctgct cgatgcgtgc     240
gaagcgcgct ggcccggcaa cagcatccgc tgcgagcacg tgatgggtgc gctgttcgtg     300
cccgcgctgc aaatggcacg cgacccgtcg gtgggcgggc gtcgttcct gcggctgctc      360 gggcgcgtgt attcggatac ctcgcccttt atccagcaat acctgctgga gcactacgcc     420
ccggtgtacg gcgcttctt cgacgccttc tcgcgcgcca ttccggcgct gccgcggcat      480
gagctcggct ggcgcctgca gtttgcgctc aaggcgctgg ccggcgtgct ggccggcgaa     540
```

```
gagctcacca acctgctgcc cgcgttcacg cagggccggc agatgagcga tgcgcacgtg    600
ctggcccagc tcaccgccat ggtggaagcc gtgctgaacg tggcgcaacc cagtgcggac    660
gacttctcgg ccctgcagtc ggtgttcgag cttggcgagc agcagcaggc cagggagcgc    720
gccagcaggg tggccgcggc gcggtctgcc gatgaactga gtgccagttg cgccgcgatg    780
gcggcaacca tgggcgatgc ggccagccag accgccgccg ccctcggcaa ggcccgcatc    840
agcgcacgca ccgtgcgcaa tgagggcacc aaacgctcag ccgtgaccag catgccggtc    900
cgcgcgcgcg agcaaaccgt gagcttcccc agcaacccgc tggatgactg gatgcgaatg    960
cgcaccagga catag                                                     975
```

<210> SEQ ID NO 52
<211> LENGTH: 324
<212> TYPE: PRT
<213> ORGANISM: C. necator

<400> SEQUENCE: 52

```
Met Lys Thr Gly Lys Ser Ser Ala Gly Asp Thr Lys Ala Arg Ile Leu
1               5                   10                  15

Asp Ala Thr Glu Lys Leu Phe Thr Glu Val Gly Tyr Glu Ala Thr Ser
            20                  25                  30

Leu Arg Gln Val Thr Ser Arg Ala Ile Val Asn Leu Ala Ala Val Asn
        35                  40                  45

Tyr His Phe Arg Ser Lys Asp Ile Met Met His Ala Val Leu Ser Arg
    50                  55                  60

Arg Leu Asp Pro Leu Asn Ala Arg Arg Leu Ala Leu Leu Asp Ala Cys
65                  70                  75                  80

Glu Ala Arg Trp Pro Gly Asn Ser Ile Arg Cys Glu His Val Met Gly
                85                  90                  95

Ala Leu Phe Val Pro Ala Leu Gln Met Ala Arg Asp Pro Ser Val Gly
            100                 105                 110

Gly Pro Ser Phe Leu Arg Leu Leu Gly Arg Val Tyr Ser Asp Thr Ser
        115                 120                 125

Pro Phe Ile Gln Gln Tyr Leu Leu Glu His Tyr Ala Pro Val Tyr Gly
    130                 135                 140

Arg Phe Phe Asp Ala Phe Ser Arg Ala Ile Pro Ala Leu Pro Arg His
145                 150                 155                 160

Glu Leu Gly Trp Arg Leu Gln Phe Ala Leu Lys Ala Leu Ala Gly Val
                165                 170                 175

Leu Ala Gly Glu Glu Leu Thr Asn Leu Leu Pro Ala Phe Thr Gln Gly
            180                 185                 190

Arg Gln Met Ser Asp Ala His Val Leu Ala Gln Leu Thr Ala Met Val
        195                 200                 205

Glu Ala Val Leu Asn Val Ala Gln Pro Ser Ala Asp Asp Phe Ser Ala
    210                 215                 220

Leu Gln Ser Val Phe Glu Leu Gly Glu Gln Gln Ala Arg Glu Arg
225                 230                 235                 240

Ala Ser Arg Leu Ala Ala Ala Arg Ser Ala Asp Glu Leu Ser Ala Ser
                245                 250                 255

Cys Ala Ala Met Ala Ala Thr Met Gly Asp Ala Ala Ser Gln Thr Ala
            260                 265                 270

Ala Ala Leu Gly Lys Ala Arg Ile Ser Ala Arg Thr Val Arg Asn Glu
        275                 280                 285

Gly Thr Lys Arg Ser Ala Val Thr Ser Met Pro Val Arg Ala Arg Glu
```

```
                290                 295                 300
Gln Thr Val Ser Phe Pro Ser Asn Pro Leu Asp Asp Trp Met Arg Met
305                 310                 315                 320

Arg Thr Arg Thr

<210> SEQ ID NO 53
<211> LENGTH: 672
<212> TYPE: DNA
<213> ORGANISM: C. necator

<400> SEQUENCE: 53
atgcgccgga tcgagaccgc gctgctcgac ggcacctggc cgcccggcac gcggctgccg      60
gccgagcggg tgctggccgg gcaatacgag gtggcgcgca acaccgtgcg cgaggcgatc     120
cagcgcctgg ccgcgcgcgg cctgctgcag agccggcgcg gtgccggggt ctacgccacc     180
gaccagctgc gcgccggcat tgcctcgccc tggggccagc tggtggccga ccaccccgcg     240
ctgcgcgacg acatcctgga gttccgccgc gtgctggagg gcgcgaccgc gtattttgcg     300
gcgctgcgcg cggatgccgc tgacgtgaag cggatccgcg ccctgatggc cgagctggaa     360
cgcgcgcgcg ccgccgacga caagcaggca gaggccgatg ccgatgcgca gctgcacgac     420
gccattgccc aggcctcgca caacaccatg ttcctgcacc tgcataccag cgtgatcggc     480
atgctgcgcg agcacatcac catcaatggc accggcctgc gcaacagga cgacggcgcg     540 tcagacctgt tgctgctgca gcatcgcacg ctgtgcgatg cgatttgcgc gcgccgcccg     600
gaagaggcgc gcaccgccat gcagacccat atcgacttcg tgcgcagccg ggtggagcag     660
gacggcgcct ga                                                         672

<210> SEQ ID NO 54
<211> LENGTH: 223
<212> TYPE: PRT
<213> ORGANISM: C. necator

<400> SEQUENCE: 54

Met Arg Arg Ile Glu Thr Ala Leu Leu Asp Gly Thr Trp Pro Pro Gly
1               5                   10                  15

Thr Arg Leu Pro Ala Glu Arg Val Leu Ala Gly Gln Tyr Glu Val Ala
                20                  25                  30

Arg Asn Thr Val Arg Glu Ala Ile Gln Arg Leu Ala Ala Arg Gly Leu
            35                  40                  45

Leu Gln Ser Arg Arg Gly Ala Gly Val Tyr Ala Thr Asp Gln Leu Arg
        50                  55                  60

Ala Gly Ile Ala Ser Pro Trp Gly Gln Leu Val Ala Asp His Pro Ala
65                  70                  75                  80

Leu Arg Asp Asp Ile Leu Glu Phe Arg Arg Val Leu Glu Gly Ala Thr
                85                  90                  95

Ala Tyr Phe Ala Ala Leu Arg Ala Asp Ala Ala Asp Val Lys Arg Ile
                100                 105                 110

Arg Ala Leu Met Ala Glu Leu Glu Arg Ala Arg Ala Ala Asp Asp Lys
            115                 120                 125

Gln Ala Glu Ala Asp Ala Asp Ala Gln Leu His Asp Ala Ile Ala Gln
        130                 135                 140

Ala Ser His Asn Thr Met Phe Leu His Leu His Thr Ser Val Ile Gly
145                 150                 155                 160

Met Leu Arg Glu His Ile Thr Ile Asn Gly Thr Gly Leu Arg Glu Gln
                165                 170                 175
```

```
Asp Asp Gly Ala Ser Asp Leu Leu Leu Gln His Arg Thr Leu Cys
            180                 185                 190

Asp Ala Ile Cys Ala Arg Arg Pro Glu Glu Ala Arg Thr Ala Met Gln
        195                 200                 205

Thr His Ile Asp Phe Val Arg Ser Arg Val Glu Gln Asp Gly Ala
        210                 215                 220
```

<210> SEQ ID NO 55
<211> LENGTH: 1476
<212> TYPE: DNA
<213> ORGANISM: C. necator

<400> SEQUENCE: 55

```
atgggcatgg tctcaataga acccggcagc tatcacgttg taccgccgca aaacccggc       60
gaggtcatcg atctgatccg gacgcacgcg atccaggtgg ttgacctcag gttcaccgac     120
ttgcccggcg tgtggcagca cttctcgatc acgctgccgg aagtcaacga cgacttattc     180
tctgtcggca tcggcttcga cgggtcttcc attcgcgggt tccaggaaat ccacgagtcc     240
gacatgctgg tcaggcctga cccggccacg gcgttcatcg atccgtattg cgcagcacca     300
acgctggcgc tgatctgcga cgtgctggac cctgtcctgc accagccgta ctcgcgcgat     360
ccgcgccata tcgcacgcaa ggccgagctg tacctccggc aaaccggtct tgccacggtt     420
tgctaccttg cccccgaact ggaattcttt atttttcgact ccatacgctt cgggcaggac    480
cagcactctg gctactacca tgtcgaatcc gccgaaggcg aatggacctc gggccgtgac    540
gaaggcgcct atggcggggg caatctcggc tacaaacagc gctacaaggg cgggtacttt     600
cccgtgccgc caagcgacac gctgcaggac atccgctccg aaatcgtgct cgcgctgatg    660
caggccggca tccaggtcga agtgcatcac catgaggtcg ccacggccgg ccagaatgaa    720
atcgacatgc gctttgcgcc actgatgcgc atggcagaca cgtgatgat gtacaagtac      780
atctgcaaga acgttgcgcg ccgccacggc aaggtcgcca ccttcatgcc caagccgctg    840
tttgccgaca cgcgagcgg catgcattgc caccagagcc tctggcgcga cgccgagaac     900
ctcttctatg acaagaacgg ttgggcgcag acgtcccaga tgtgccgttg gtatataggc     960
ggcttgctca gccacgcccc cgcgctgatg gcattctgcg caccgagcac gaactcctac    1020
aagcggctgg tgcccggata cgaggcgcct gtcaatctgg ccatgtcgca gcgcaaccgg   1080
tccgccgcgg cccggattcc aatggtttcg gattccccga gcgccaggcg cgttgaattt     1140
cgctgtcctg atccgtcggc caatgcctac ctcgccttct cggcaatgct gctcgccggc    1200
ctggacggca ttgaaaacca gacggacccc ggcgacccgc tcgacaagaa catctatgat    1260
ctgccaccgg aggaagccgc cgcatccgg caggtaccag gctccctgga agagtcgctt      1320
tgcgcgctgg aagccgattc agcgttcctg cgcaaggggg atgtcttcac tgaagacctg   1380
atcacgacct ggattgatta caagcgcacg cgcgagatcg atacattgaa ggtgcggcca   1440
cacccgtggg aattccagct ctacttcgac atctga                              1476
```

<210> SEQ ID NO 56
<211> LENGTH: 491
<212> TYPE: PRT
<213> ORGANISM: C. necator

<400> SEQUENCE: 56

```
Met Gly Met Val Ser Ile Glu Pro Gly Ser Tyr His Val Val Pro Pro
1               5                   10                  15
```

Gln Asn Pro Gly Glu Val Ile Asp Leu Ile Arg Thr His Ala Ile Gln
            20                  25                  30

Val Val Asp Leu Arg Phe Thr Asp Leu Pro Gly Val Trp Gln His Phe
        35                  40                  45

Ser Ile Thr Leu Pro Glu Val Asn Asp Asp Leu Phe Ser Val Gly Ile
    50                  55                  60

Gly Phe Asp Gly Ser Ser Ile Arg Gly Phe Gln Glu Ile His Glu Ser
65                  70                  75                  80

Asp Met Leu Val Arg Pro Asp Pro Ala Thr Ala Phe Ile Asp Pro Tyr
                85                  90                  95

Cys Ala Ala Pro Thr Leu Ala Leu Ile Cys Asp Val Leu Asp Pro Val
            100                 105                 110

Leu His Gln Pro Tyr Ser Arg Asp Pro Arg His Ile Ala Arg Lys Ala
        115                 120                 125

Glu Leu Tyr Leu Arg Gln Thr Gly Leu Ala Thr Val Cys Tyr Leu Gly
    130                 135                 140

Pro Glu Leu Glu Phe Phe Ile Phe Asp Ser Ile Arg Phe Gly Gln Asp
145                 150                 155                 160

Gln His Ser Gly Tyr Tyr His Val Glu Ser Ala Glu Gly Glu Trp Thr
                165                 170                 175

Ser Gly Arg Asp Glu Gly Ala Tyr Gly Gly Asn Leu Gly Tyr Lys
            180                 185                 190

Gln Arg Tyr Lys Gly Gly Tyr Phe Pro Val Pro Ser Asp Thr Leu
        195                 200                 205

Gln Asp Ile Arg Ser Glu Ile Val Leu Ala Leu Met Gln Ala Gly Ile
    210                 215                 220

Gln Val Glu Val His His His Glu Val Ala Thr Ala Gly Gln Asn Glu
225                 230                 235                 240

Ile Asp Met Arg Phe Ala Pro Leu Met Arg Met Ala Asp Asn Val Met
                245                 250                 255

Met Tyr Lys Tyr Ile Cys Lys Asn Val Ala Arg Arg His Gly Lys Val
            260                 265                 270

Ala Thr Phe Met Pro Lys Pro Leu Phe Ala Asp Asn Ala Ser Gly Met
        275                 280                 285

His Cys His Gln Ser Leu Trp Arg Asp Ala Glu Asn Leu Phe Tyr Asp
    290                 295                 300

Lys Asn Gly Trp Ala Gln Thr Ser Gln Met Cys Arg Trp Tyr Ile Gly
305                 310                 315                 320

Gly Leu Leu Ser His Ala Pro Ala Leu Met Ala Phe Cys Ala Pro Ser
                325                 330                 335

Thr Asn Ser Tyr Lys Arg Leu Val Pro Gly Tyr Glu Ala Pro Val Asn
            340                 345                 350

Leu Ala Met Ser Gln Arg Asn Arg Ser Ala Ala Arg Ile Pro Met
        355                 360                 365

Val Ser Asp Ser Pro Ser Ala Arg Arg Val Glu Phe Arg Cys Pro Asp
    370                 375                 380

Pro Ser Ala Asn Ala Tyr Leu Ala Phe Ser Ala Met Leu Leu Ala Gly
385                 390                 395                 400

Leu Asp Gly Ile Glu Asn Gln Thr Asp Pro Gly Asp Pro Leu Asp Lys
                405                 410                 415

Asn Ile Tyr Asp Leu Pro Pro Glu Glu Ala Ala Arg Ile Arg Gln Val
            420                 425                 430

Pro Gly Ser Leu Glu Glu Ser Leu Cys Ala Leu Glu Ala Asp Ser Ala

```
                435                 440                 445
Phe Leu Arg Lys Gly Asp Val Phe Thr Glu Asp Leu Ile Thr Thr Trp
    450                 455                 460

Ile Asp Tyr Lys Arg Thr Arg Glu Ile Asp Thr Leu Lys Val Arg Pro
465                 470                 475                 480

His Pro Trp Glu Phe Gln Leu Tyr Phe Asp Ile
                485                 490
```

<210> SEQ ID NO 57
<211> LENGTH: 906
<212> TYPE: DNA
<213> ORGANISM: C. necator

<400> SEQUENCE: 57

```
atgactgcgc ccttcgacat cctgacccgc atcgccgagc gcggccccgc gctgcgcctg      60
gccgagcaga aggtggcgca ggtggtactg gaagacctgg ccggcgcggc cgccgccagc     120
atcaatgagc tggcgcgcaa ggccggcgtc agcgaggcca gcgtgacgcg ctttgccaag     180
gccatcggct gcgcgacgt gcgcgacctg aagctgcgcc tggcgcaggc caccgcggtg     240
ggtgcgcgct tcctgcagcc cggcagcgtt cccgccggtg aagccacccc ggccacactc     300
gctgacagca tccacgccga catcctcacc gcgctcgaag tcaaccgcgg catgatggat     360
gcgcagcgca tcgaacaggc cgcgcgcctg ttgctcggcg cacgcatggt ctacgctttt     420
ggcatgggcg gcggctcgtc gttcatggcc gacgaggccc gccatcgcct ggcgcgcctg     480
ggccagccgg tggcgagcta ccaggacgcg ctgctacaga agatggtggc ggccacgctg     540
ggccgcgacg acgtggtgct ggccttctcg gccagcggcc gcgtgccgga gatgctggcc     600
agctgcgata tcgcgcgcga gtacggtgcc cgcctggtgg ccgtgaccgc gctgggctcg     660
ccactggccg cgcgcgccga cgtgctgctg ccggtgcgca cgctggagac ggatttcatt     720
ttcaaaccgt cggcatcgcg ctacgccatg ctgatggtgc tggacgtgct cgccacgcaa     780
tgcgcgctgt tgcagccgga ccagagcaaa gagcgcctgc ccggctcaa gtacgtgctg     840
gacagccacc gcggcgaaag cggccccgcc cggggccctg acagccgcca gccgctcgga     900
gactga                                                               906
```

<210> SEQ ID NO 58
<211> LENGTH: 301
<212> TYPE: PRT
<213> ORGANISM: C. necator

<400> SEQUENCE: 58

```
Met Thr Ala Pro Phe Asp Ile Leu Thr Arg Ile Ala Glu Arg Gly Pro
1               5                   10                  15

Ala Leu Arg Leu Ala Glu Gln Lys Val Ala Gln Val Val Leu Glu Asp
            20                  25                  30

Leu Ala Gly Ala Ala Ala Ala Ser Ile Asn Glu Leu Ala Arg Lys Ala
        35                  40                  45

Gly Val Ser Glu Ala Ser Val Thr Arg Phe Ala Lys Ala Ile Gly Cys
    50                  55                  60

Arg Asp Val Arg Asp Leu Lys Leu Arg Leu Ala Gln Ala Thr Ala Val
65                  70                  75                  80

Gly Ala Arg Phe Leu Gln Pro Gly Ser Val Pro Ala Gly Glu Ala Thr
                85                  90                  95

Pro Ala Thr Leu Ala Asp Ser Ile His Ala Asp Ile Leu Thr Ala Leu
            100                 105                 110
```

Glu Val Asn Arg Gly Met Met Asp Ala Gln Arg Ile Glu Gln Ala Ala
            115                 120                 125

Arg Leu Leu Leu Gly Ala Arg Met Val Tyr Ala Phe Gly Met Gly Gly
    130                 135                 140

Gly Ser Ser Phe Met Ala Asp Glu Ala Arg His Arg Leu Ala Arg Leu
145                 150                 155                 160

Gly Gln Pro Val Ala Ser Tyr Gln Asp Ala Leu Leu Gln Lys Met Val
                165                 170                 175

Ala Ala Thr Leu Gly Arg Asp Asp Val Val Leu Ala Phe Ser Ala Ser
            180                 185                 190

Gly Arg Val Pro Glu Met Leu Ala Ser Cys Asp Ile Ala Arg Glu Tyr
    195                 200                 205

Gly Ala Arg Leu Val Ala Val Thr Ala Leu Gly Ser Pro Leu Ala Ala
    210                 215                 220

Arg Ala Asp Val Leu Leu Pro Val Arg Thr Leu Glu Thr Asp Phe Ile
225                 230                 235                 240

Phe Lys Pro Ser Ala Ser Arg Tyr Ala Met Leu Met Val Leu Asp Val
                245                 250                 255

Leu Ala Thr Gln Cys Ala Leu Leu Gln Pro Asp Gln Ser Lys Glu Arg
            260                 265                 270

Leu Arg Arg Leu Lys Tyr Val Leu Asp Ser His Arg Gly Glu Ser Gly
    275                 280                 285

Pro Ala Arg Gly Pro Asp Ser Arg Gln Pro Leu Gly Asp
    290                 295                 300

<210> SEQ ID NO 59
<211> LENGTH: 1344
<212> TYPE: DNA
<213> ORGANISM: C. necator

<400> SEQUENCE: 59

```
gtgaattctc cctcccttga cgcattcctg cgggggttg cccgccgcga ccccaatcaa      60
cctgaattcc tccaggccgt gaaggaagtg atgatgacgc tctggccctt tgtcgagcgc     120
aatccgcgct acgccgacca ggccctgctc gagcggctgg tggagcccga gcgcgtgatc     180
cagttccgcg tggcctggac cgacgaccag aacgggtgc aggtcaaccg cgccttccgc      240
gtgcagcaca gctcggccat cggcccgttc aagggcggca tgcgcttcca cccgactgtg     300
aacctgtcgg tgctgaagtt cctgggcttc gagcagacct tcaagaacgc gctgaccacg     360
ctgcccatgg gcgcggcaa gggcggctcg actttgatc caagggcaa gtccgatggc       420 gaagtgatgc gtttctgcca ggcgctggtg accgagctgt ccgccaccct gggcccggat     480
accgacatcc cggccggcga catcggcgtg gcgcacgtg aagtcggctt tatgccggc       540 atgatgaaga agctttccaa ccagtccgcc tgcgtcttca ccggcaaggg cctggcctac     600
ggcggcagcc tgatgcgccc ggaagcgacc ggctacggca cggtctactt tgcgcaggag     660
atgctgcacc ggcgcgggcg cgctttcgac ggcctgcgcg tgctgatctc gggctcgggc     720
aacgtggccc agtacgcggc cgagaaggcg atcgagctgg cgccacggt gctgacgctg     780 tccgattcag gcggcgtgct gcactacccg caggcatga ctaccgagca gctggccgaa     840
gtgatggcct tcaagaatga agagcgcggc cgcctgtctg actttgccgc ccgccacggc     900
atggccttcg aagccggccg caccccgtgg cacgtgcccg ccgacgtggc gctgccgtgc     960
gccacccaga acgagctgga cggcaacgac gccgagaccc tgctcggcaa tggcgtgatc    1020
```

-continued

```
tgcgtggccg aaggcgccaa catgccgtcg acgctggaag ccgtggaccg ctttgtcgat    1080
gcgaagatcc tctacgcccc gggcaaggcc agcaatgccg gcggcgttgc cacttccggc    1140
ctggaaatgt cgcagaacgc catgcgcctg tcctggcacc atgccgaggt cgacgagaag    1200
ctgcacgcga tcatgaagga catccaccag aactgcatcc accacgggca gaaggcggat    1260
ggctatatca actacgtgga aggcgcgaac atcgccggct tcgtcaaggt agccgacgcc    1320
atgctggcgc aaggcgtgat ctga                                          1344
```

<210> SEQ ID NO 60
<211> LENGTH: 447
<212> TYPE: PRT
<213> ORGANISM: C. necator

<400> SEQUENCE: 60

```
Met Asn Ser Pro Ser Leu Asp Ala Phe Leu Ala Gly Val Ala Arg Arg
1               5                   10                  15

Asp Pro Asn Gln Pro Glu Phe Leu Gln Ala Val Lys Glu Val Met Met
            20                  25                  30

Thr Leu Trp Pro Phe Val Glu Arg Asn Pro Arg Tyr Ala Asp Gln Ala
        35                  40                  45

Leu Leu Glu Arg Leu Val Gly Pro Glu Arg Val Ile Gln Phe Arg Val
    50                  55                  60

Ala Trp Thr Asp Asp Gln Asn Arg Val Gln Val Asn Arg Ala Phe Arg
65                  70                  75                  80

Val Gln His Ser Ser Ala Ile Gly Pro Phe Lys Gly Gly Met Arg Phe
                85                  90                  95

His Pro Thr Val Asn Leu Ser Val Leu Lys Phe Leu Gly Phe Glu Gln
            100                 105                 110

Thr Phe Lys Asn Ala Leu Thr Thr Leu Pro Met Gly Gly Gly Lys Gly
        115                 120                 125

Gly Ser Asp Phe Asp Pro Lys Gly Lys Ser Asp Gly Glu Val Met Arg
    130                 135                 140

Phe Cys Gln Ala Leu Val Thr Glu Leu Phe Arg His Leu Gly Pro Asp
145                 150                 155                 160

Thr Asp Ile Pro Ala Gly Asp Ile Gly Val Gly Ala Arg Glu Val Gly
                165                 170                 175

Phe Met Ala Gly Met Met Lys Lys Leu Ser Asn Gln Ser Ala Cys Val
            180                 185                 190

Phe Thr Gly Lys Gly Leu Ala Tyr Gly Gly Ser Leu Met Arg Pro Glu
        195                 200                 205

Ala Thr Gly Tyr Gly Thr Val Tyr Phe Ala Gln Glu Met Leu His Arg
    210                 215                 220

Arg Gly Arg Ala Phe Asp Gly Leu Arg Val Leu Ile Ser Gly Ser Gly
225                 230                 235                 240

Asn Val Ala Gln Tyr Ala Ala Glu Lys Ala Ile Glu Leu Gly Ala Thr
                245                 250                 255

Val Leu Thr Leu Ser Asp Ser Gly Gly Val Leu His Tyr Pro Gln Gly
            260                 265                 270

Met Thr Thr Glu Gln Leu Ala Glu Val Met Ala Phe Lys Asn Glu Glu
        275                 280                 285

Arg Gly Arg Leu Ser Asp Phe Ala Ala Arg His Gly Met Ala Phe Glu
    290                 295                 300

Ala Gly Arg Thr Pro Trp His Val Pro Ala Asp Val Ala Leu Pro Cys
305                 310                 315                 320
```

```
Ala Thr Gln Asn Glu Leu Asp Gly Asn Asp Ala Glu Thr Leu Leu Gly
            325                 330                 335

Asn Gly Val Ile Cys Val Ala Glu Gly Ala Asn Met Pro Ser Thr Leu
        340                 345                 350

Glu Ala Val Asp Arg Phe Val Asp Ala Lys Ile Leu Tyr Ala Pro Gly
            355                 360                 365

Lys Ala Ser Asn Ala Gly Gly Val Ala Thr Ser Gly Leu Glu Met Ser
    370                 375                 380

Gln Asn Ala Met Arg Leu Ser Trp His His Ala Glu Val Asp Glu Lys
385                 390                 395                 400

Leu His Ala Ile Met Lys Asp Ile His Gln Asn Cys Ile His His Gly
                405                 410                 415

Gln Lys Ala Asp Gly Tyr Ile Asn Tyr Val Glu Gly Ala Asn Ile Ala
            420                 425                 430

Gly Phe Val Lys Val Ala Asp Ala Met Leu Ala Gln Gly Val Ile
        435                 440                 445

<210> SEQ ID NO 61
<211> LENGTH: 1395
<212> TYPE: DNA
<213> ORGANISM: C. necator

<400> SEQUENCE: 61
atgaagtcag agttgagtgc gcatcttgcg gcgccagccg ggcgctgac cccggctccg      60 cggttcaaca ccgtcgaaga cgctcaagac tatctgctgg cgcgcggcgt cagctacgtc    120
ctcgcgcagt tcgtcgatat ccacggcgtc gccaaggcca atcggtgcc agtggcgcat     180 cttggctcgg tcctggcaga gggtgcgggc tttgccggct ttgccatctg gggcgtcggc    240
attgaaccgc atggcccgga cttcatggct cgcggggatc tcgataccat cgggctggtg    300
ccatggcagc cgggcctggc ccggatcgta tgcgaagggc atgtcgatgg tgcgccatgg    360
cagtacgaca gccgggtcgt cctgaagcgg cagatcgcca ggctctcgca aggtggctac    420
acgctttata ccggcctcga gcctgagttt tcgctgctgc ccgtgacga caaaggcggc     480 atcggtccgt gcgacccgag cgatacgctg gccaagcctt gctacgacta caaggggctg    540
tcgcgcacgc gtactttcct ggagcgtctg tccaacggac tgcgcgccgc gggaatcgat    600
gtctaccaga tcgaccatga agacgccaac gggcaattcg aactgaatta caccttcacc    660
gactgcctga cgtcttgcga ccatttcatc ttcttcaaga tggcggcatc ggaaatcgcc    720
aacgagctgg gcctggtgtg ctccttcatg ccgaagccgt ttgcaaaccg ccccggcaac    780
ggcatgcata tgcacatgtc gatcggcgat ggccagcgca acctgtttgc tgacaagagc    840
gacccgcgcg gctggacct gtcccagctg gcctatcact ccttggcgg gctgctggcc     900 catgcgccgg cgctcacggc gctttgcgcg cccaccgtca attcctacaa gcggctcgtg    960
gtgggccgtt ccctcaccgg cgccacctgg gctcccgcgt atatcagcta tggcgacaac   1020
aatcgctcga gcatgatccg catccccaag ggccggctgg aactgcggct gcccgatggc   1080
gccgccaacc cgtatctcgc cacagcggcc gtgattgcgg cggggcttga cggcatcgac   1140
cggaagctcg atcccggcgc accgcgcaac accaatctct atgagtggag cgaggcgcag   1200
ctggccgaag ccggcatcgg cctgctaccc cagaaccttg gcagcgcgct ggatgccctc   1260
gaagccgatg cgctgataac cgaggcactg ggaccgttg cgcaagagtt cctgaagctc    1320
aagcgcatgg agtggctcga atatcaacgg catgtctcgg actgggaagt gaagcagtac   1380
```
ctggaattct tttga 1395

<210> SEQ ID NO 62
<211> LENGTH: 464
<212> TYPE: PRT
<213> ORGANISM: C. necator

<400> SEQUENCE: 62

Met Lys Ser Glu Leu Ser Ala His Leu Ala Ala Pro Ala Gly Ala Leu
1               5                   10                  15

Thr Pro Ala Pro Arg Phe Asn Thr Val Glu Asp Ala Gln Asp Tyr Leu
            20                  25                  30

Leu Ala Arg Gly Val Ser Tyr Val Leu Ala Gln Phe Val Asp Ile His
        35                  40                  45

Gly Val Ala Lys Ala Lys Ser Val Pro Val Ala His Leu Gly Ser Val
    50                  55                  60

Leu Ala Glu Gly Ala Gly Phe Ala Gly Phe Ala Ile Trp Val Gly
65                  70                  75                  80

Ile Glu Pro His Gly Pro Asp Phe Met Ala Arg Gly Asp Leu Asp Thr
            85                  90                  95

Ile Gly Leu Val Pro Trp Gln Pro Gly Leu Ala Arg Ile Val Cys Glu
        100                 105                 110

Gly His Val Asp Gly Ala Pro Trp Gln Tyr Asp Ser Arg Val Val Leu
    115                 120                 125

Lys Arg Gln Ile Ala Arg Leu Ser Gln Gly Gly Tyr Thr Leu Tyr Thr
130                 135                 140

Gly Leu Glu Pro Glu Phe Ser Leu Leu Arg Arg Asp Asp Lys Gly Gly
145                 150                 155                 160

Ile Gly Pro Cys Asp Pro Ser Asp Thr Leu Ala Lys Pro Cys Tyr Asp
            165                 170                 175

Tyr Lys Gly Leu Ser Arg Thr Arg Thr Phe Leu Glu Arg Leu Ser Asn
        180                 185                 190

Gly Leu Arg Ala Ala Gly Ile Asp Val Tyr Gln Ile Asp His Glu Asp
    195                 200                 205

Ala Asn Gly Gln Phe Glu Leu Asn Tyr Thr Phe Thr Asp Cys Leu Thr
210                 215                 220

Ser Cys Asp His Phe Ile Phe Phe Lys Met Ala Ala Ser Glu Ile Ala
225                 230                 235                 240

Asn Glu Leu Gly Leu Val Cys Ser Phe Met Pro Lys Pro Phe Ala Asn
            245                 250                 255

Arg Pro Gly Asn Gly Met His Met His Met Ser Ile Gly Asp Gly Gln
        260                 265                 270

Arg Asn Leu Phe Ala Asp Lys Ser Asp Pro Arg Gly Leu Asp Leu Ser
    275                 280                 285

Gln Leu Ala Tyr His Phe Leu Gly Gly Leu Leu Ala His Ala Pro Ala
290                 295                 300

Leu Thr Ala Leu Cys Ala Pro Thr Val Asn Ser Tyr Lys Arg Leu Val
305                 310                 315                 320

Val Gly Arg Ser Leu Thr Gly Ala Thr Trp Ala Pro Ala Tyr Ile Ser
            325                 330                 335

Tyr Gly Asp Asn Asn Arg Ser Ser Met Ile Arg Ile Pro Lys Gly Arg
        340                 345                 350

Leu Glu Leu Arg Leu Pro Asp Gly Ala Ala Asn Pro Tyr Leu Ala Thr
    355                 360                 365

-continued

```
Ala Ala Val Ile Ala Ala Gly Leu Asp Gly Ile Asp Arg Lys Leu Asp
    370             375             380

Pro Gly Ala Pro Arg Asn Thr Asn Leu Tyr Glu Trp Ser Glu Ala Gln
385             390             395             400

Leu Ala Glu Ala Gly Ile Gly Leu Leu Pro Gln Asn Leu Gly Ser Ala
            405             410             415

Leu Asp Ala Leu Glu Ala Asp Ala Leu Ile Thr Glu Ala Leu Gly Pro
            420             425             430

Val Ala Gln Glu Phe Leu Lys Leu Lys Arg Met Glu Trp Leu Glu Tyr
        435             440             445

Gln Arg His Val Ser Asp Trp Glu Val Lys Gln Tyr Leu Glu Phe Phe
    450             455             460
```